US010837009B1

(12) United States Patent
Ong et al.

(10) Patent No.: US 10,837,009 B1
(45) Date of Patent: Nov. 17, 2020

(54) DNA LIGASE VARIANTS

(71) Applicant: New England Biolabs, Inc., Ipswich, MA (US)

(72) Inventors: Jennifer Ong, Salem, MA (US); Gregory Lohman, Cambridge, MA (US); Aine Quimby, Newton, NH (US); Vladimir Potapov, Auburndale, MA (US); John M. Pryor, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 47 days.

(21) Appl. No.: 16/227,533

(22) Filed: Dec. 20, 2018

Related U.S. Application Data

(60) Provisional application No. 62/609,577, filed on Dec. 22, 2017.

(51) Int. Cl.
*C12N 9/10* (2006.01)
*C12N 9/00* (2006.01)
*C12P 19/34* (2006.01)

(52) U.S. Cl.
CPC ............... *C12N 9/93* (2013.01); *C12P 19/34* (2013.01); *C12Y 605/01001* (2013.01)

(58) Field of Classification Search
CPC combination set(s) only.
See application file for complete search history.

(56) References Cited

U.S. PATENT DOCUMENTS

2018/0320162 A1  11/2018  Miller et al.

FOREIGN PATENT DOCUMENTS

WO  2014145269 A1  9/2014

OTHER PUBLICATIONS

Guo et al., Proceedings of National Academy of Sciences, vol. 101, No. 25, pp. 9205-9210, Jun. 2004.*
Ngo et al. In the Protein Folding Problem and Tertiary Structure Prediction, 1994, Merz et al. (ed.), Birkhauser, Boston, MA, pp. 433 and 492-495.*
Umapathi et al. et al., (2018) MRS Advances, 3(26), 1475-1483. doi:10.1557/adv.2018.331.
Geer, et al. Genome Research 12:1619-1623 (2002).
Jin, P., et al. ACS Synthetic Biology, 5(3), 259-268 (2016).
PURExpress In Vitro Protein Synthesis Instruction Manual.
Greenough, L., et al. (2016). Nucleic Acids Research, 44(2), e15.
Lehman, DNA ligase: structure, mechanism, and function. Science. 1974;186(4166):790-7. pmid:4377758.
Shuman, DNA ligases: progress and prospects. J Biol Chem. 2009;284(26):17365-9. pmid:19329793.
Cherepanov, et al., Kinetics and thermodynamics of nick sealing by T4 DNA ligase. Eur J Biochem. 2003;270 (21):4315-25. pmid:14622296.
Kukshal, et al., Human DNA ligase III bridges two DNA ends to promote specific intermolecular DNA end joining. Nucleic Acids Res. 2015;43(14):7021-31. pmid:26130724.
Pheiffer, et al., Polymer-stimulated ligation: enhanced blunt- or cohesive-end ligation of DNA or deoxyribooligonucleotides by T4 DNA ligase in polymer solutions. Nucleic Acids Res. 1983;11(22):7853-71. pmid:6359064.
Teraoka, et al., Influence of polyethylene glycol on the ligation reaction with calf thymus DNA ligases I and II. J Biochem. 1987;101(1)225-31. pmid:3571204.
Shuman, et al., Mutational analysis of vaccinia DNA ligase defines residues essential for covalent catalysis. Virology. 1995;211(1):73-83. pmid:7645238.
Lohman, et al., DNA ligases. Curr Protoc Mol Biol. 2011;Chapter 3:Unit 3.14. pmid:21472697.
Engler, et al., Golden gate shuffling: a one-pot DNA shuffling method based on type IIs restriction enzymes. PloS one. 2009;4(5):e5553. pmid:19436741.
Werner, et al., Fast track assembly of multigene constructs using Golden Gate cloning and the MoClo system. Bioeng Bugs. 2012;3(1):38-43. pmid:22126803.
Gibson, et al., Enzymatic assembly of DNA molecules up to several hundred kilobases. Nat Methods. 2009;6 (5)343-5. pmid:19363495.
Cai, et al., Characterization of bacteriophage T3 DNA ligase. J Biochem. 2004;135(3):397-403. pmid:15113838.
Lauer, et al., Cloning, nucleotide sequence, and engineered expression of Thermus thermophilus DNA ligase, a homolog of *Escherichia coli* DNA ligase. J Bacteriol. 1991;173(16):5047-53. pmid:1840584.
Tong, et al., Biochemical properties of a high fidelity DNA ligase from *Thermus* species AK16D. Nucleic Acids Res. 1999;27(3):788-94. pmid:9889274.
Doherty, et al., Bacteriophage T7 DNA ligase. Overexpression, purification, crystallization, and characterization. J Biol Chem. 1996;271(19):11083-9. pmid:8626651.
Ho, et al., Characterization of an ATP-dependent DNA ligase encoded by Chlorella virus PBCV-1. J Virol. 1997;71 (3):1931-7. pmid:9032324.
Richardson, et al., Studies on the joining of DNA by polynucleotide ligase of phage T4. Cold Spring Harb Symp Quant Biol. 1968;33:151-64. pmid:4891960.
Weiss, et al., Enzymatic breakage and joining of deoxyribonucleic acid. VI. Further purification and properties of polynucleotide ligase from *Escherichia coli* infected with bacteriophage T4. J Biol Chem. 1968;243(17):4543-55. pmid:4879167.
Fareed, et al., Enzymatic breakage and joining of deoxyribonucleic acid. 8. Hybrids of ribo- and deoxyribonucleotide homopolymers as substrates for polynucleotide ligase of bacteriophage T4. J Biol Chem. 1971;246(4):925-32. pmid:5543691.
Sgaramella, et al., Studies on polynucleotides. CXVI. A further study of the T4 ligase-catalyzed joining of DNA at base-paired ends. J Mol Biol. 1972;72(3):493-502. pmid:4349756.

(Continued)

*Primary Examiner* — Richard G Hutson
(74) *Attorney, Agent, or Firm* — New England Biolabs, Inc; Harriet M. Strimpel

(57) ABSTRACT

Mutant bacteriophage DNA ligases that have increased tolerance to salt and/or heat is provided. Methods, compositions and kits that employ the same are also provided.

22 Claims, 21 Drawing Sheets

Specification includes a Sequence Listing.

(56) References Cited

OTHER PUBLICATIONS

Raae, et al., Kinetics and effect of salts and polyamines on T4 polynucleotide ligase. Eur J Biochem. 1975;60 (2):437-43. pmid:173544.
Sgaramella, et al., Use of the T4 polynucleotide ligase in the joining of flush-ended DNA segments generated by restriction endonucleases. Eur J Biochem. 1978;86(2):531-7. pmid:350585.
Ferretti, et al., Temperature dependence of the joining by T4 DNA ligase of termini produced by type II restriction endonucleases. Nucleic Acids Res. 1981;9(1):85-93. pmid:6259621.
Wilson, et al., Engineered DNA ligases with improved activities in vitro, Protein Engineering, Design & Selection. 26(7): 471-8 (2013).
Hayashi, et al., Influence of monovalent cations on the activity of T4 DNA ligase in the presence of polyethylene glycol. Nucleic Acids Res. 1985;13(9):3261-71. pmid:2987879.
Wu, et al., Specificity of the nick-closing activity of bacteriophage T4 DNA ligase. Gene. 1989;76(2):245-54. pmid:2753355.
Sugino, et al., Interaction of bacteriophage T4 RNA and DNA ligases in joining of duplex DNA at base-paired ends. J Biol Chem. 1977;252(11):3987-94. pmid:863910.
GenBank accession No. AAA32562.1.
GenBank accession No. YP_803139.1.
GenBank accession No. YP_004010059.1.
GenBank accession No. YP_003934836.1.
GenBank accession No. YP_009289585.1.
Database UniProt assession No. AOA173GAK3 (Sep. 7, 2016).
Database UniProt accession No. AOA1L7DQW0 (Mar. 15, 2017).
Database UniProt accession No. AOA249XVV13 (Nov. 22, 2017).
Rossi, et al., Functional Characterization of the DNA Ligase: A New Insight into the Mechanism of Action, Nucleic Acids Research, 25, 11, 1997.
Johnson, et al., DNA ligase: getting a grip to seal the deal. Curr Biol. 2005 15: R90-2.
Kletzin, et al., Molecular characterisation of a DNA ligase gene of the extremely thermophilic archaeon Desulfurolobus ambivalens shows close phylogenetic relationship to eukaryotic ligases Nucleic Acids Research 1992 20 5389-5396.
Pascal, et al., DNA and RNA ligases: structural variations and shared mechanisms. Curr Opin Struct Biol. 2008 18: 96-105.
Rossi, et al, Functional characterization of the T4 DNA ligase: a new insight into the mechanism of action Nucleic Acids Research 1997, 25: 2106-2113.
Shi, et al., T4 DNA ligase structure reveals a prototypical ATP-dependent ligase with a unique mode of sliding clamp interaction. Nucleic Acids Res. 2018 46: 10474-10488.
Shuman (Closing the gap on DNA ligase. Structure 1996 4: 653-6.

\* cited by examiner

FIG. 10 (SEQ ID NO:1)

|  | 10 | 20 | 30 | 40 |
| --- | --- | --- | --- | --- |

```
                            10          20          30          40
SEQ_ID_No._1_T4     M I L K I L N E I A S I G S T K Q K Q A I L E K N K D N E L L K R V Y R L T Y S R G L Q Y Y I K K W
YP_009277571.1      M I L K I L N E I A S I G S T K Q K Q A I L E K N K D N E L L K R V Y R L T Y S R G L Q Y Y I K K W
AXC33998.1          M I L K I L N E I A S I G S T K Q K Q A I L E K N K D N E L L K R V Y R L T Y S R G L Q Y Y I K K W
YP_009098583.1      M I L K I L N E I A S I G S T K Q K Q A I L E K N K D N E L L K R V Y R L T Y S R G L Q Y Y I K K W
WP_080181510.1      M I L K I L N E I A S I G S T K Q K Q A I L E K N K D N E L L K R V Y R L T Y S R G L Q Y Y I K K W
YP_009288563.1      M I L K I L N E I A S I G S T K Q K Q A I L E K N K D N E L L K R V Y R L T Y S R G L Q Y Y I K K W
AUV59569.1          M I L K I L N E I A S I G S T K Q K Q A I L E K N K D N E L L K R V Y R L T Y S R G L Q Y Y I K K W
YP_009180698.1      M I L K I L N E I A S I G S T K Q K Q A I L E K N K D N E L L K R V Y R L T Y S R G L Q Y Y I K K W
AWD91483.1          M I L K I L N E I A S I G S T K Q K Q A I L E K N K D N E L L K R V Y R L T Y S R G L Q Y Y I K K W
WP_074146536.1      M I L K I L N E I A S I G S T K Q K Q A I L E K N K D N E L L K R V Y R L T Y S R G L Q Y Y I K K W
YP_009030807.1      M I L K I L N E I A S I G S T K Q K Q A I L E K N K D N E L L K R V Y R L T Y S R G L Q Y Y I K K W
AXF42508.1          M I L K I L N E I A S I G S T K Q K Q A I L E K N K D N E L L K R V Y R L T Y S R G L Q Y Y I K K W
AUV61060.1          M I L K I L N K I A S I G S T K Q K Q A I L E K N K D N E L L K R V Y R L T Y S R G L Q Y Y I K K W
WP_088209698.1      M I L K I L N E I A S I G S T K Q K Q A I L E K N K D N E L L K R V Y R L T Y S R G L Q Y Y I K K W
ATI16790.1          M I L K I L N E I A S I G S T K Q K Q A I L E K N K D N E L L K R V Y R L T Y S R G L Q Y Y I K K W
P19088.1            M I L K I L N E I A S I G S T K Q K Q A I L E K N K D N E L L K R V Y R L T Y S R G L Q Y Y I K K W
YP_009284262.1      M I L K I L N E I A S I G S T K Q K Q A I L E K N K D N E L L K R V Y R L T Y S R G L Q Y Y I K K W
YP_009102401.1      M I L K I L N E I A S I G S T K Q K Q A I L E K N K D N E L L K R V Y R L T Y S R G L Q Y Y I K K W
YP_004415092.1      M I L K I L N E I A S I G S T K Q K Q A I L E K N K D N E L L K R V Y R L T Y S R G L Q Y Y I K K W
AUV63060.1          M I L K I L N E I A S I G S T K Q K Q A I L E K N K D N E L L K R V Y R L T Y S R G L Q Y Y I K K W
YP_006986754.1      M I L K I L N E I A S I G S T K Q K Q A I L E K N K D N E L L K R V Y R L T Y S R G L Q Y Y I K K W
YP_009102671.1      M I L K I L N E I A S I G S T K Q K Q A I L E K N K D N E L L K R V Y R L T Y S R G L Q Y Y I K K W
BBC14820.1          M I L K I L N E I A S I G S T K Q K Q A I L E K N K D N E L L K R V Y R L T Y S R G L Q Y Y I K K W
APU02553.1          M I L K I L N E I A S I G S T K Q K Q A I L E K N K D N E L L K R V Y R L T Y S R G L Q Y Y I K K W
YP_009149442.1      M I L K I L N E I A S I G S T K Q K Q A I L E K N K D N E L L K R V Y R L T Y S R G L Q Y Y I K K W
YP_002854154.1      M I L K I L N E I A S I G S T K Q K Q A I L E K N K D N E L L K R V Y R L T Y S R G L Q Y Y I K K W
YP_009210118.1      M I L K I L N E I A S I G S T K Q K Q A I L E K N K D N E L L K R V Y R L T Y S R G L Q Y Y I K K W
YP_009168015.1      M I L K I L N E I A S I G S T K Q K Q A I L E K N K D N E L L K R V Y R L T Y S R G L Q Y Y I K K W
ASZ77030.1          M I L K I L N E I A S I G S T K Q K Q A I L E K N K D N E L L K R V Y R L T Y S R G L Q Y Y I K K W
ASZ76112.1          M I L K I L N E I A S I G S T K Q K Q A I L E K N K D N E L L K R V Y R L T Y S R G L Q Y Y I K K W
YP_009153798.1      M I L K I L N E I A S I G S T K Q K Q A I L E K N K D N E L L K R V Y R L T Y S R G L Q Y Y I K K W
YP_009278924.1      M I L K I L N E I A S I G S T K Q K Q A I L E K N K D N E L L K R V Y R L T Y S R G L Q Y Y I K K W
YP_007004939.1      M I L K I L N E I A S I G S T K Q K Q A I L E K N K D N E L L K R V Y R L T Y S R G L Q Y Y I K K W
YP_009197257.1      M I L K I L N E I A S I G S T K Q K Q A I L E K N K D N E L L K R V Y R L T Y S R G L Q Y Y I K K W
YP_002854533.1      M I L K I L N E I A S I G S T K Q K Q A I L E K N K D N E L L K R V Y R L T Y S R G L Q Y Y I K K W
YP_007004575.1      M I L K I L N E I A S I G S T K Q K Q A I L E K N K D N E L L K R V Y R L T Y S R G L Q Y Y I K K W
YP_009281531.1      M I L K I L N E I A S I G S T K Q K Q A I L E K N K D N E L L K R V Y R L T Y S R G L Q Y Y I K K W
ATE86456.1          M I L K I L N E I A S I G S T K Q K Q A I L E K N K D N E L L K R V Y R L T Y S R G L Q Y Y I K K W
ANH49669.1          M I L K I L N E I A S I G S T K Q K Q A I L E K N K D N E L L K R V Y R L T Y S R G L Q Y Y I K K W
YP_009111017.1      M I L K I L N E I A S I G S T K Q K Q A I L E K N K D N E L L K R V Y R L T Y S R G L Q Y Y I K K W
AUV63745.1          M I L K I L N E I A S I G S T K Q K Q A I L E K N K D N E L L K R V Y R L T Y S R G L Q Y Y I K K W
YP_009148639.1      M I L K I L N E I A S I G S T K Q K Q A I L E R N K D N E L L K R V Y R L T Y S R G L Q Y Y I K K W
AWM11982.1          M I L K I L N E I A S I G S T K Q K Q A I L E K N K D N E L L K R V Y R L T Y S R G L Q Y Y I K K W
BBC14541.1          M I L K I L N E I A S I G S T K Q K Q A I L E K N K D N E L L K R V Y R L T Y S R G L Q Y Y I K K W
YP_803139.1         M I L K I L N E I A S I G S T K Q K Q A I L E K N K D N E L L K R V Y R L T Y S R G L Q Y Y I K K W
AWD91739.1          M I L K I L N E I A S I G S T K Q K Q A I L E K N K D N E L L K R V Y R L T Y S R G L Q Y Y I K K W
WP_100771463.1      M I L K I L N E I A S I G S T K Q K Q A I L E K N K D N E L L K R V Y R L T Y S R G L Q Y Y I K K W
```

FIG. 11

```
                          60         70         80         90
SEQ_ID_No._1_T4     PKPGIATQSFGMLTLTDMLDFIEFTLATRKLTGNAAIEELTGYITDGKKD
YP_009277571.1      PKPGIATQSFGMLTLTDMLDFIEFTLATRKLTGNAAIEELTGYITDGKKD
AXC33998.1          PKPGIATQSFGMLTLTDMLDFIEFTLATRKLTGNAAIEELIGYITDGKKD
YP_009098583.1      PKPGIATQSFGMLTLTDMLDFIEFTLATRKLTGNAAIEELTGYITDGKKD
WP_080181510.1      PKPGIATQSFGMLTLTDMLDFIEFTLATRKLTGNAAIEELTGYITDGKKD
YP_009288563.1      PKPGIATQSFGMLTITDMLDFIEFTLATRKLTGNAAIEELTGYITDGKKD
AUV59569.1          PKPGIATQSFGMLTLTDMLDFIEFTLATRKLTGNAAIEELTGYITDGKKD
YP_009180698.1      PKPGIATQSFGMLTLTDMLDFIEFTLATRKLTGNAAIEELTGYITDGKKD
AWD91483.1          PKPGIATQSFGMLTITDMLDFIEFTLATRKLTGNAAIEELTGYITDGKKD
WP_074146536.1      PKPGIATQSFGMLTLTDMLDFIEFTLATRKLTGNAAIEELTGYITDGKKD
YP_009030807.1      PKPGIATQSFGMLTITDMLDFIEFTLATRKLTGNAAIEELTGYITDGKKD
AXF42508.1          PKPGIATQSFGMLTLTDMLDFIELTLATRKLTGNAAIEELTGYITDGKKD
AUV61060.1          PKPGIATQSFGMLTLTDMLDFIEFTLATRKLTGNAAIEELTGYIADGKKD
WP_088209698.1      PKPGIATQSFGMLTITDMLDFIEFTLATRKLTGNAAIEELTGYITDGKKD
ATI16790.1          PKPGIATQSFGMLTLTDMLDFIELTLATRKLTGNAAIEELTGYIADGKKD
P19088.1            PKPGIATQSFGMLTLTDMLDFIEFTLATRKLTGNAAIEELTGYITDGKKD
YP_009284262.1      PKPGIATQSFGMLTLTDMLDFIEFTLATRKLTGNAAIEELTGYITDGKKD
YP_009102401.1      PKPGIATQSFGMLTLTDMLDFIEFTLATRKLTGNAAIEELTGYITDGKKD
YP_004415092.1      PKPGIATQSFGMLTLTDMLDFIEFTLATRKLTGNAAIEELTGYIADGKKD
AUV63060.1          PKPGIATQSFGMLTITDMLDFIEFTLATRKLTGNAAIEELTGYITDGKKD
YP_006986754.1      PKPGIATQSFGMLTLTDMLDFIEFTLATRKLTGNAAIEELTGYITDGKKD
YP_009102671.1      PKPGIATQSFGMLTLTDMFDFIEFTLATRKLTGNAAIEELTGYITDGKKD
BBC14820.1          PKPGIATQSFGMLTLIDMLDFIEFTLATRKLTGNAAIEELTGYITDGKKD
APU02553.1          PKPGIATQSFGMLTLTDMLDFIEFTLATRKLTGNAAIEELTGYITDGKKD
YP_009149442.1      PKPGIATQSFGMLTLTDMLDFIEFTLATRKLTGNAAIEELTGYIADGKKD
YP_002854154.1      PKPGIATQSFGMLTLTDMLDFIEFTLATRKLTGNAAIEELTGYIADGKKD
YP_009210118.1      PKSGIATQSFGMLTLTDMLDFIEFTLATRKLTGNAAIEELSGYITDGKKD
YP_009168015.1      PKPGIATQSFGMLTLTDMLDFIEFTLATRKLTGNAAIEELTGYIADGKKD
ASZ77030.1          PKPGISTQSFGMLTLTDMLDFIEFTLATRKLTGNAAIEELTGYIADGKKD
ASZ76112.1          PKPGITTQSFGMLTLTDMLDFIEFTLATRKLTGNAAIEELTGYITDGKKD
YP_009153798.1      PKPGIATQSFGMLTIADMLDFIEFTLATRKLTGNAAIEELTGYITDGKKD
YP_009278924.1      PKPGIATQSFGMLTLTDMLDFIEFTLATRKLTGNAAIEELTGYIADGKKD
YP_007004939.1      PKPGIATQSFGMLTLTDMLDFIEFTLATRKLTGNAAIEELTGYIADGKKD
YP_009197257.1      PKPGIATQSFGMLTLTDMLDFIEFTLATRKLTGNAAIEELVGYITDGKKD
YP_002854533.1      PKPGIATQSFGMLTLTDMLDFIEFTLATRKLTGNAAIEELTGYIADGKKD
YP_007004575.1      PKPDIATQSFGMLTITDMLDFIEFTLATRKLTGNAAIEELTGYITDGKKD
YP_009281531.1      PKPGIATQSFGMLTLTDMLDFIEFTLATRKLTGNAAIEELTGYIADGKKD
ATE86456.1          PKPGIATQSFGMLTLTDMLDFIEFTLATRKLTGNAAIEELTGYITDGKKD
ANH49669.1          PKPGIATQSFGMLTITDMLDFIEFTLATRKLTGNAAIEELTGYITDGKKD
YP_009111017.1      PKPGIATQSFGMLTITDMLDFIEFTLATRKLTGNAAIEELTGYITDGKKD
AUV63745.1          PKPGIATQSFGMLTITDMLDFIEFTLATRKLTGNAAIEELTGYITDGKKD
YP_009148639.1      PKPGIATQSFGMLTITDMLDFIEFTLATRKLTGNAAIEELTGYITDGKKD
AWM11982.1          PKPGIATQSFGMLTITDMLDFIEFTLATRKLTGNAAIEELTGYITDGKKD
BBC14541.1          PKPGIATQSFGMLTITDMLDFIEFTLATRKLTGNAAIEELTGYITDGKKD
YP_803139.1         PKPGIATQSFGMLTLTDMLDFIEFTLATRKLTGNAAIEELTGYITDGKKD
AWD91739.1          PKPGIATQSFGMLTITDMLDFIEFTLATRKLTGNAAIEELTGYITDGKKD
WP_100771463.1      PKPGIATQSFGMLTITDMLDFIEFTLATRKLTGNAAIEELTGYITDGKKD
```

FIG. 11 CONT.

```
                         110          120         130         140
SEQ_ID_No._1_T4    DVEVLRRVMMRDLECGASVSIANKVWPGLIPEQPQMLASSYDEKGINKNI
YP_009277571.1     DVEVLRRVMMRDLECGASVSIANKVWPGLIPEQPQMLASSYDEKGINKNI
AXC33998.1         DVEVLRRVMMRDLECGASVSIANKVWPGLIPEQPQMLASSYDEKGINKNI
YP_009098583.1     DVEVLRRVMMRDLECGASVSIANKVWPGLIPEQPQMLASSYDEKGINKNI
WP_080181510.1     DVEVLRRVMMRDLECGASVSIANKVWPGLIPEQPQMLASSYDEKGINKNI
YP_009288563.1     DVEVLRRVMMRDLECGASVSIANKVWPGLIPEQPQMLASSYDEKGISKNI
AUV59569.1         DVEVLRRVMMRDLECGASVSIANKVWPGLIPEQPQMLASSYDEKGINKNI
YP_009180698.1     DVEVLRRVMMRDLECGASVSIANKVWPGLIPEQPQMLASSYDEKGINKNI
AWD91483.1         DVEVLRRVMMRDLECGASVSIANKVWPGLIPEQPQMLASSYDEKGINKNI
WP_074146536.1     DVEVLRRVMMRDLECGASVSIANKVWPGLIPEQPQMLASSYDEKGINKNI
YP_009030807.1     DVEVLRRVMMRDLECGASVSIANKVWPGLIPEQPQMLASSYDEKGINKNI
AXF42508.1         DVEVLRRVMMRDLECGASVSIANKVWPGLIPEQPQMLASSYDEKGINKNI
AUV61060.1         DVEVLRRVMMRDLECGASVSIANKVWPGLIPEQPQMLASSYDEKGISKNI
WP_088209698.1     DVEVLRRVMMRDLECGASVSIANKVWPGLIPEQPQMLASSYDEKGISKNI
ATI16790.1         DVEVLRRVMMRDLECGASVSIANKVWPGLIPEQPQMLASSYDEKGINKNI
P19088.1           DVEVLRRVMMRDLECGASVSIANKVWPGLIPEQPQMLASSYDEKGINKNI
YP_009284262.1     DVEVLRRVMMRDLECGASVSIANKVWPGLIPEQPQMLASSYDEKGINKNI
YP_009102401.1     DVEVLRRVMMRDLECGASVSIANKVWPGLIPEQPQMLASSYDEKGINKNI
YP_004415092.1     DVEVLRRVMMRDLECGASVSIANKVWPGLIPEQPQMLASSYDEKGINKNI
AUV63060.1         DVEVLRRVMMRDLECGASVSIANKVWPGLIPEQPQMLASSYDEKGISKNI
YP_006986754.1     DVEVLRRVMMRDLECGASVSIANKVWPGLIPEQPQMLASSYDEKGINKNI
YP_009102671.1     DVEVLRRVMMRDLECGASVSIANKVWPGLIPEQPQMLASSYDEKGINKNI
BBC14820.1         DVEVLRRVMMRDLECGASVSIANKVWPGLIPEQPQMLASSYDEKGINKNI
APU02553.1         DVEVLRRVMMRDLECGASVSIANKVWPGLIPEQPQMLASSYDEKGINKNI
YP_009149442.1     DVEVLRRVMMRDLECGASVSIANKVWPGLIPEQPQMLASSYDEKGINKNI
YP_002854154.1     DVEVLRRVMMRDLECGASVSIANKVWPGLIPEQPQMLASSYDEKGINKNI
YP_009210118.1     DVEVLRRVMMRDLECGASVSIANKVWPGLIPEQPQMLASSYDEKGINKNI
YP_009168015.1     DVEVLRRVMMRDLECGASVSIANKVWPGLIPEQPQMLASSYDEKGINKNI
ASZ77030.1         DVEVLRRVMMRDLECGASVSIANKVWPGLIPEQPQMLASSYDEKGINKNI
ASZ76112.1         DVEVLRRVMMRDLECGASVSIANKVWPGLIPEQPQMLASSYDEKGINKNI
YP_009153798.1     DVEVLRRVMMRDLECGASVSIANKVWPGLIPEQPQMLASSYDEKGINKNI
YP_009278924.1     DVEVLRRVMMRDLECGASVSIANKVWPGLIPEQPQMLASSYDEKGINKNI
YP_007004939.1     DVEVLRRVMMRDLECGASVSIANKVWPGLIPEQPQMLASSYDEKGISKNI
YP_009197257.1     DVEVLRRVMMRDLECGASVSIANKVWPGLIPEQPQMLASSYDEKGISKNI
YP_002854533.1     DVEVLRRVMMRDLECGASVSIANKVWPGLIPEQPQMLASSYDEKGISKNI
YP_007004575.1     DVEVLRRVMMRDLECGASVSIANKVWPGLIPEQPQMLASSYDEKGISKNI
YP_009281531.1     DVEVLRRVMMRDLECGASVSIANKVWPGLIPEQPQMLASSYDEKGINKNI
ATE86456.1         DVEVLRRVMMRDLECGASVSIANKVWPGLIPEQPQMLASSYDEKGINKNI
ANH49669.1         DVEVLRRVMMRDLECGASVSIANKVWPGLIPEQPQMLASSYDEKGISKNI
YP_009111017.1     DVEVLRRVMMRDLECGASVSIANKVWPGLIPEQPQMLASSYDEKGISKNI
AUV63745.1         DVEVLRRVMMRDLECGASVSIANKVWPGLIPEQPQMLASSYDEKGISKNI
YP_009148639.1     DVEVLRRVMMRDLECGASVSIANKVWPGLIPEQPQMLASSYDEKGISKNI
AWM11982.1         DVEVLRRVMMRDLECGASVSIANKVWPGLIPEQPQMLASSYDEKGISKNI
BBC14541.1         DVEVLRRVMMRDLECGASVSIANKVWPGLIPEQPQMLASSYDEKGISKNI
YP_803139.1        DVEVLRRVMMRDLECGASVSIANKVWPGLIPEQPQMLASSYDEKGINKNI
AWD91739.1         DVEVLRRVMMRDLECGASVSIANKVWPGLIPEQPQMLASSYDEKGISKNI
WP_100771463.1     DVEVLRRVMMRDLECGASVSIANKVWPGLIPEQPQMLASSYDEKGISKNI
```

FIG. 11 CONT.

```
                             160         170         180         190
                             |    |    |    |    |    |    |    |    |
SEQ_ID_No._1_T4      K F P A F A Q L K A D G A R C F A E V R G D E L D D V R L L S R A G N E Y L G L D L L K E E L I K M
YP_009277571.1       K F P A F A Q L K A D G A R C F A E V R G D E L D D V R L L S R A G N E Y L G L D L L K E E L I K M
AXC33998.1           K F P A F A Q L K A D G A R C F A E V R G D E L D D V R L L S R A G N E Y L G L D L L K E E L I K M
YP_009098583.1       K F P A F A Q L K A D G A R C F A E V R G D E L D D V R L L S R A G N E Y L G L D L L K E E L I K M
WP_080181510.1       K F P A F A Q L K A D G A R C F A E V R G D E L D D V R L L S R A G N E Y L G L D L L K E E L I K M
YP_009288563.1       K F P A F A Q L K A D G A R C F A E V R G D E L D D V R L L S R A G N E Y L G L D L L K E E L I K M
AUV59569.1           K F P A F A Q L K A D G A R C F A E V R G D E L D D V R L L S R A G N E Y L G L D L L K E E L I K M
YP_009180698.1       K F P A F A Q L K A D G A R C F A E V R G D E L D D V R L L S R A G N E Y L G L D L L K E E L I K M
AWD91483.1           K F P A F A Q L K A D G A R C F A E V R G D E L D D V R L L S R A G N E Y L G L D L L K E E L I K M
WP_074146536.1       K F P A F A Q L K A D G A R C F A E V R G D E L D D V R L L S R A G N E Y L G L D L L K E E L I K M
YP_009030807.1       K F P A F A Q L K A D G A R C F A E V R G D E L D D V R L L S R A G N E Y L G L D L L K E E L I K M
AXF42508.1           K F P A F A Q L K A D G A R C F A E V R G D E L D D V R L L S R A G N E Y L G L D L L K E E L I K M
AUV61060.1           K F P A F A Q L K A D G A R C F A E V R G D E L D D V R L L S R A G N E Y L G L D L L K E E L I K M
WP_088209698.1       K F P A F A Q L K A D G A R C F A E V R G D E L D D V R L L S R A G N E Y L G L D L L K E E L I K M
ATI16790.1           K F P A F A Q L K A D G A R C F A E V R G D E L D D V R L L S R A G N E Y L G L D L L K E E L I K M
P19088.1             K F P A F A Q L K A D G A R C F A E V R G D E L D D V R L L S R A G N E Y L G L D L L K E E L I K M
YP_009284262.1       K F P A F A Q L K A D G A R C F A E V R G D E L D D V R L L S R A G N E Y L G L D L L K E E L I K M
YP_009102401.1       K F P A F A Q L K A D G A R C F A E V R G D E L D D V R L L S R A G N E Y L G L D L L K E E L I K M
YP_004415092.1       K F P A F A Q L K A D G A R C F A E V R G D E L D D V R L L S R A G N E Y L G L D L L K E E L I K M
AUV63060.1           K F P A F A Q L K A D G A R C F A E V R G D E L D D V R L L S R A G N E Y L G L D L L K E E L I K M
YP_006986754.1       K F P A F A Q L K A D G A R C F A E V R G D E L D D V R L L S R A G N E Y L G L D L L K E E L I K M
YP_009102671.1       K F P A F A Q L K A D G A R C F A E V R G D E L D D V R L L S R A G N E Y L G L D L L K E E L I K M
BBC14820.1           K F P A F A Q L K A D G A R C F A E V R G D E L D D V R L L S R A G N E Y L G L D L L K E E L I K M
APU02553.1           K F P A F A Q L K A D G A R C F A E V R G D E L D D V R L L S R A G N E Y L G L D L L K E E L I K M
YP_009149442.1       K F P A F A Q L K A D G A R C F A E V R G D E L D D V R L L S R A G N E Y L G L D L L K E E L I K M
YP_002854154.1       K F P A F A Q L K A D G A R C F A E V R G D E L D D V R L L S R A G N E Y L G L D L L K E E L I K M
YP_009210118.1       K F P A F A Q L K A D G A R C F A E V R G D E L D D V R L L S R A G N E Y L G L D L L K E E L I K M
YP_009168015.1       K F P A F A Q L K A D G A R C F A E V R G D E L D D V R L L S R A G N E Y L G L D L L K E E L I K M
ASZ77030.1           K F P A F A Q L K A D G A R C F A E V R G D E L D D V R L L S R A G N E Y L G L D L L K E E L I K M
ASZ76112.1           K F P A F A Q L K A D G A R C F A E V R G D E L D D V R L L S R A G N E Y L G L D L L K E E L I K M
YP_009153798.1       K F P A F A Q L K A D G A R C F A E V R G D E L D D V R L L S R A G N E Y L G L D L L K E E L I K M
YP_009278924.1       K F P A F A Q L K A D G A R C F A E V R G D E L D D V R L L S R A G N E Y L G L D L L K E E L I K M
YP_007004939.1       K F P A F A Q L K A D G A R C F A E V R G D E L D D V R L L S R A G N E Y L G L D L L K E E L I K M
YP_009197257.1       K F P A F A Q L K A D G A R C F A E V R G D E L D D V R L L S R A G N E Y L G L D L L K E E L I K M
YP_002854533.1       K F P A F A Q L K A D G A R C F A E V R G D E L D D V R L L S R A G N E Y L G L D L L K E E L I K M
YP_007004575.1       K F P A F A Q L K A D G A R C F A E V R G D E L D D V R L L S R A G N E Y L G L D L L K E E L I K M
YP_009281531.1       K F P A F A Q L K A D G A R C F A E V R G D E L D D V R L L S R A G N E Y L G L D L L K E E L I K M
ATE86456.1           K F P A F A Q L K A D G A R C F A E V R G D E L D D V R L L S R A G N E Y L G L D L L K E E L I K M
ANH49669.1           K F P A F A Q L K A D G A R C F A E V R G D E L D D V R L L S R A G N E Y L G L N L L K E E L I K M
YP_009111017.1       K F P A F A Q L K A D G A R C F A E V R G D E L D D V R L L S R A G N E Y L G L D L L K E E L I K M
AUV63745.1           K F P A F A Q L K A D G A R C F A E V R G D E L D D V R L L S R A G N E Y L G L D L L K E E L I K M
YP_009148639.1       K F P A F A Q L K A D G A R C F A E V R G D E L D D V R L L S R A G N E Y L G L D L L K E E L I K M
AWM11982.1           K F P A F A Q L K A D G A R C F A E V R G D E L D D V R L L S R A G N E Y L G L D L L K E E L I K M
BBC14541.1           K F P A F A Q L K A D G A R C F A E V R G D E L D D V R L L S R A G N E Y L G L D L L K E E L I K M
YP_803139.1          K F P A F A Q L K A D G A R C F A E V R G D E L D D V R L L S R A G N E Y L G L D L L K E E L I K M
AWD91739.1           K F P A F A Q L K A D G A R C F A E V R G D E L D D V R L L S R A G N E Y L G L D L L K E E L I K M
WP_100771463.1       K F P A F A Q L K A D G A R C F A E V R G D E L D D V R L L S R A G N E Y L G L D L L K E E L I K M
```

FIG. 11 CONT.

|                  | 210                                               | 219              | 229                | 239                  |
|------------------|---------------------------------------------------|------------------|--------------------|----------------------|
| SEQ_ID_No._1_T4  | T A E A R Q I H P E G V L I D G E L - V Y H E Q V K K E P E G L D F L F D A Y P E N S K A K E F A E |
| YP_009277571.1   | T A E A R Q I H P E G V L I D G E L - V Y H E Q V K K E P E G L D F L F D A Y P E N S K A K E F A E |
| AXC33998.1       | T A E A R Q I H P E G V L I D G E L - V Y H E Q V E K E P E G L D F L F D A Y P E N S K A K E F A E |
| YP_009098583.1   | T A E A R Q I H P E G V L I D G E L - V Y H E Q V K K E P E G L D F L F D A Y P E I S K A K E F A E |
| WP_080181510.1   | T A E A R Q I H P E G V L I D G E L - V Y H E Q V K K E P K G L D F L F D A Y P E I S K A K E F A E |
| YP_009288563.1   | T A E A R Q I H P E G V L I D G E L - V Y H E Q V K K E P E G L D F L F D A Y P E I S K A K E F A E |
| AUV59569.1       | T A E A R Q I H P E G V L I D G E L - V Y H E Q V K K D P E G L D F L F D A Y P E I S K S K E F A E |
| YP_009180698.1   | T A E A R Q I H P E G V L I D G E L - V Y H E Q V K K E P E G L D F L F D A Y P E I S K A K E F A E |
| AWD91483.1       | T A E A R Q I H P E G V L I D G E L - V Y H E Q V K K E P E G L D F L F D A Y P E I S K A K E F A E |
| WP_074146536.1   | T A E A R Q I H P E G V L I D G E L - V Y H E Q V K K E P E G L D F L F D A Y P E I S K A K E F A E |
| YP_009030807.1   | T A E A R Q I H P E G V L I D G E L - V Y H E Q V K K E P E G L D F L F D A Y P E I S K A K E F A E |
| AXF42508.1       | T A E A R Q I H P E G V L I D G E L - V Y H E Q V K K E P E G L D F L F D A Y P E I S K A K E F A E |
| AUV61060.1       | T A E A R Q I H P E G V L I D G E L - V Y H E Q V E K E P E G L D F L F D A Y P E N S K A K E F A E |
| WP_088209698.1   | T A E A R Q I H P E G V L I D G E L - V Y H E Q V K K E P E G L D F L F D A Y P E I S K A K E F A E |
| ATI16790.1       | T A E A R Q I H P E G V L I D G E L - V Y H E Q V K K E P E G L D F L F D A Y P E I S K A K E F A E |
| P19088.1         | T A E A R Q I H P E G V L I D G E L - V Y H E Q V K K E P E G L D F L F D A H P E N S K V K D F T E |
| YP_009284262.1   | T A E A R Q I H P E G V L I D G E L - V Y H E Q V K K E P E G L D F L F D A Y P E I S K A K E F A E |
| YP_009102401.1   | T A E A R Q I H P E G V L I D G E L - V Y H E Q V E K E P E G L D F L F D A Y P E I S K A K E F A E |
| YP_004415092.1   | T A E A R Q I H P E G V L I D G E L - V Y H E Q V K K E P E G L D F L F D A Y P E I S K A K E F A E |
| AUV63060.1       | T A E A R Q I H P E G V L I D G E L - V Y H E Q V K K E P E G L D F L F D A Y P E I S K A K E F A E |
| YP_006986754.1   | T A E A R Q I H P E G V L I D G E L - V Y H E Q V K K E P E G L D F L F D A Y P E I S K A K E F A E |
| YP_009102671.1   | T A E A R Q I H P E G V L I D G E L - V Y H E Q V E K E P E G L D F L F D A Y P E I S K A K E F A E |
| BBC14820.1       | T A E A R Q I H P E G V L I D G E L - V Y H E Q V K K E P E G L D F L F D A H P E N S K V K D F T E |
| APU02553.1       | T A E A R Q I H P E G V L I D G E L - V Y H E Q V E K E P E G L D F L F D A Y P E I S K A K E F A E |
| YP_009149442.1   | T A E A R Q I H P E G V L I D G E L - V Y H E Q V K K E P E G L D F L F D A Y P E I S K A K E F A E |
| YP_002854154.1   | T A E A R Q I H P E G V L I D G E L - V Y H E Q V E K E P E G L D F L F D A Y P E I S K A K E F A E |
| YP_009210118.1   | T A E A R Q I H P E G V L I D G E L - V Y H E Q V K K E P E G L D F L F D A Y P E I S K A K E F A E |
| YP_009168015.1   | T T E A R Q I H P E G V L I D G E L - V Y H E Q V K K E P E G L D F L F D A Y P E I S K A K E F A E |
| ASZ77030.1       | T A E A R Q I H P E G V L I D G E L - V Y H E Q V E K E P E G L D F L F D A Y P E I S K A K E F A E |
| ASZ76112.1       | T A E A R Q I H P E G V L I D G E L - V Y H E Q V E K E P E G L D F L F D A Y P E I S K A K E F A E |
| YP_009153798.1   | T A E A R Q I H P E G V L I D G E L - V Y H E Q V K K E P E G L D F L F D A Y P E I S K A K E F A E |
| YP_009278924.1   | T A E A R Q I H P E G V L I D G E L - V Y H E Q V K K E P E G L D F L F D S H P E N S K V K D F T E |
| YP_007004939.1   | T A E A R Q I H P E G V L I D G E L - V Y H E Q V E K E P E G L D F L F D A Y P E I S K A K E F A E |
| YP_009197257.1   | T A E A R Q I H P E G V L I D G E L - V Y H E Q V K K E P E G L D F L F D A Y P E I S K A K E F A E |
| YP_002854533.1   | T A E A R Q I H P E G V L I D G E L - V Y H E Q V E K E P E G L D F L F D A Y P E I S K A K E F A E |
| YP_007004575.1   | T A E A R Q I H P E G V L I D G E L - V Y H E Q V K K E P E G L D F L F D A Y P E I S K A K E F A E |
| YP_009281531.1   | T A E A R Q I H P E G V L I D G E L - V Y H E Q V K K E P E G L D F L F D A Y P E I S K A K E F A E |
| ATE86456.1       | T T E A R Q I H P E G V L I D G E L - V Y H E Q V E K E P E G L D F L F D A Y P E I S K A K E F A E |
| ANH49669.1       | T A E A R Q I H P E G V L I D G E L V V Y H E Q V E K E P E G L D F L F D A Y P E I S K A K E F A E |
| YP_009111017.1   | T A E A R Q I H P E G V L I D G E L - V Y H E Q V E K E P E G L D F L F D A - P E I S K A K E F A E |
| AUV63745.1       | T A E A R Q I H P E G V L I D G E L - V Y H E Q V E K E P E G L D F L F D A - P E I S K A K E F A E |
| YP_009148639.1   | T A E A R Q I H P E G V L I D G E L - V Y H E Q V K K E P E G L D F L F D A - P E I S K A K E F A E |
| AWM11982.1       | T A E A R Q I H P E G V L I D G E L - V Y H E Q V K K E P E G L D F L F D T - P E I S K A K D F T E |
| BBC14541.1       | T A E A R Q I H P E G V L I D G E L - V Y H E Q V K K E P E G L D F L F D A - P E I S K A K E F A E |
| YP_803139.1      | T A E A R Q I H P E G V L I D G E L - V Y H E Q V K K E S E G L D F L F D T - P E I S K A K D F T E |
| AWD91739.1       | T A E A R Q I H P E G V L I D G E L - V Y H E Q V K K E P E G L D F L F D A - P E I S K A K E V A E |
| WP_100771463.1   | T A E A R Q I H P E G V L I D G E L - V Y H E Q V E K E P E G L D F L F G T - P E I S K A K E F A E |

FIG. 11 CONT.

```
                                          259         269         279         289
SEQ_ID_No._1_T4    V A E S R T A S N G I A N K S L K G T I S E K E A Q C M K F Q V W D Y V P L V E I Y S L P A F R L K
YP_009277571.1     V A E S R T A S N G I A N K S L K G T I S E K E A Q C M K F Q V W D Y V P L V E I Y G L P A F R L K
AXC33998.1         V A E S R T A S N G I A N K S L K G T I S E K E A Q C M K F Q V W D Y V P L V E I Y G L P A F R L K
YP_009098583.1     V A E S R T A S N G I A N K S L K G T I S E K E A Q C M K F Q V W D Y V P L V E I Y G L P A F R L K
WP_080181510.1     V A E S R T A S N G I A N K S L K G T I S E K E A Q C M K F Q V W D Y V P L V E I Y G L P A F R L K
YP_009288563.1     V A E S R T A S N G I A N K S L K G T I S E K E A Q C M K F Q V W D Y V P L V E I Y G L P A F R L K
AUV59569.1         V A E S R T A S N G I A N K S L K G T I S E K E A Q C M K F Q V W D Y V P L V E I Y G L P A F R L K
YP_009180698.1     V A E S R T T S N G I A N K S L K G T I S E K E A Q C M K F Q V W D Y V P L V E I Y G L P A F R L K
AWD91483.1         V A E S R T A S N G I A N K S L K G T I S E K E A Q C M K F Q V W D Y V P L V E I Y G L P A F R L K
WP_074146536.1     V A E S R T A S N G I A N K S L K G T I S E K E A Q C M K F Q V W D Y V P L V E I Y G L P A F R L K
YP_009030807.1     V A E S R T T S N G I A N K S L K G T I S E K E A Q C M K F Q V W D Y V P L V E I Y G L P A F R L K
AXF42508.1         V A E S R T A S N G I A N K S L K G T I S E K E A Q C M K F Q V W D Y V P L V E I Y G L P V F R L K
AUV61060.1         V A E S R T A S N G I A N K S L K G T I S E K E A Q C M K F Q V W D Y V P L V E I Y G L P A F R L K
WP_088209698.1     V A E S R T T S N G I A N K S L K G T I S E K E A Q C M K F Q V W D Y V P L V E I Y G L P A F R L K
ATI16790.1         V A E S R T A S N G I A N K S L K G T I S E K E A Q C M K F Q V W D Y V P L V E I Y G L P A F R L K
P19088.1           V A E S R T A S N G I A N K S L K G T I S E K E A Q C M K F Q V W D Y V P L V E V Y G L P A F R L K
YP_009284262.1     V A E S R T T S N G I A N K S L K G T I S E K E A Q C M K F Q V W D Y V P L V E I Y G L P A F R L K
YP_009102401.1     V A E S R T A S N G I A N K S L K G T I S E K E A Q C M K F Q V W D Y V P L V E I Y G L P A F R L K
YP_004415092.1     V A E S R T A S N G I A N K S L K G T I S E K E A K C M K F Q V W D Y V P L V E I Y G L P A F R L K
AUV63060.1         V A E S R T T S N G I A N K S L K G T I S E K E A Q C M K F Q V W D Y V P L V E I Y G L P A F R L K
YP_006986754.1     V A E S R T A S N G I A N K S L K G T I S E K E A Q C M K F Q V W D Y V P L V E I Y G L P A F R L K
YP_009102671.1     V A E S R T A S N G I A N K S L K G T I S E K E A Q C M K F Q V W D Y V P L V E I Y G L P A F R L K
BBC14820.1         V A E S R T A S N G I A N K S L K G T I S E K E A Q C M K F Q V W D Y V P L V E I Y G L P A F R L K
APU02553.1         V A E S R T A S N G I A N K S L K G T I S E K E A Q C M K F Q V W D Y V P L V E I Y G L P A F R L K
YP_009149442.1     V A E S R T T S N G I A N K S L K G T I S E K E A Q C M K F Q V W D Y V P L V E I Y G L P A F R L K
YP_002854154.1     V A E S R T T S N G I A N K S L K G T I S E K E A Q C M K F Q V W D Y V P L V E I Y G L P A F R L K
YP_009210118.1     V A E S R T T S N G I A N K S L K G T I S E K E A Q C M K F Q V W D Y V P L V E I Y G L P A F R L K
YP_009168015.1     V A E S R T T S N G I A N K S L K G T I S E K E A Q C M K F Q V W D Y V P L V E I Y G L P A F R L K
ASZ77030.1         V A E S R T T S N G I A N K S L K G T I S E K E A Q C M K F Q V W D Y V P L V E I Y G L P A F R L K
ASZ76112.1         V A E S R T T S N G I A N K S L K G T I S E K E A Q C M K F Q V W D Y V P L V E I Y G L P A F R L K
YP_009153798.1     V A E S R T A S N G I A N K S L K G T I S E K E A Q C M K F Q V W D Y V P L V E I Y G L P A F R L K
YP_009278924.1     V A E S R T A S N G I A N K S L K G T I S E K E A Q C M K F Q V W D Y V P L V E V Y G L P A F R L K
YP_007004939.1     V A E S R T T S N G I A N K S L K G T I S E K E A Q C M K F Q V W D Y V P L V E I Y G L P A F R L K
YP_009197257.1     V A E S R T T S N G I A N K S L K G T I S E K E A Q C M K F Q V W D Y V P L V E I Y G L P A F R L K
YP_002854533.1     V A E S R T T S N G I A N K S L K G T I S E K E A Q C M K F Q V W D Y V P L V E I Y G L P A F R L K
YP_007004575.1     V A E S R T T S N G I A N K S L K G T I S E K E A Q C M K F Q V W D Y V P L V E I Y G L P A F R L K
YP_009281531.1     V A E S R T T S N G I A N K S L K G T I S E K E A Q C M K F Q V W D Y V P L V E I Y G L P A F R L K
ATE86456.1         V A E S R T T S N G I A N K S L K G T I S E K E A Q C M K F Q V W D Y V P L V E I Y G L P A F R L K
ANH49669.1         V A E S R T T S N G I A N K S L K G T I S E K E A Q C M K F Q V W D Y V P L V E I Y G L P A F R L K
YP_009111017.1     V A E S R T A S N G I A N K S L K G T I S E K E A Q C M K F Q V W D Y V P L V E I Y G L P A F R L K
AUV63745.1         V A E S R T A S N G I A N K S L K G T I S E K E A Q C M K F Q V W D Y V P L V E I Y G L P A F R L K
YP_009148639.1     V A E S R T T S N G I A N K S L K G T I S E K E A Q C M K F Q V W D Y V P L V E I Y G L P A F R L K
AWM11982.1         V A E S R T A S N G I A N K S L K G T I S E K E A Q C M K F Q V W D Y V P L V E I Y G L P A F R L K
BBC14541.1         V A E S R T A S N G I A N K S L K G T I S E K E A K C M K F Q V W D Y V P L V E I Y G L P A F R L K
YP_803139.1        V A E S R T A S N G I A N K S L K G T I S E K E A Q C M K F Q V W D Y V P L V E V Y G L P A F R L K
AWD91739.1         V A E S R T A S N G I A N K S L K G T I S E K E A K C M K F Q V W D Y V P L V E I Y G L P A F R L K
WP_100771463.1     V A E S R T A S N G I A N K S L K G T I S E K E A K C M K F Q V W D Y V P L V E I Y G L P A F R L K
```

FIG. 11 CONT.

|                  | 309         | 319         | 329         | 339         |
|------------------|-------------|-------------|-------------|-------------|
| SEQ_ID_No._1_T4  | Y DVR F SK L EQMT SGY DKV I L I ENQV VNN L DEAKV I YKKY I DQGLEGI I LK |
| YP_009277571.1   | Y DVR F SK L EQMT SGY DKV I L I ENQV VNN L DEAKV I YKKY I DQGLEGI I LK |
| AXC33998.1       | Y DVR F SK L EQMT SGY DKV I L I ENQV VNN L DEAKV I YKKY I DQGLEGI I LK |
| YP_009098583.1   | Y DVR F SK L EQMT SGY DKV I L I ENQV VNN L DEAKV I YKKY I DQGLEGI I LK |
| WP_080181510.1   | Y DVR F SK L EQMT SGY DKV I L I ENQV VNN L DEAKV I YKKY I DQGLEGI I LK |
| YP_009288563.1   | Y DVR F SK L EQMT SGY DKV I L I ENQV VNN L DEAKV I YKKY I DQGLEGI I LK |
| AUV59569.1       | Y DVR F SK L EQMT SGY DKV I L I ENQV VNN L DEAKV I YKKY I DQGLEGI I LK |
| YP_009180698.1   | Y DVR F SK L EQMT SGY DKV I L I ENQV VNN L DEAKV I YKKY I DQGLEGI I LK |
| AWD91483.1       | Y DVR F SK L EQMT SGY DKV I L I ENQV VNN L DEAKV I YKKY I DQGLEGI I LK |
| WP_074146536.1   | Y DVR F SK L EQMT SGY DKV I L I ENQL VNN L DEAKV I YKKY I DQGLEGI I LK |
| YP_009030807.1   | Y DVR F SK L EQMT SGY DKV I L I ENQV VNN L DEAKV I YKKY I DQGLEGI I LK |
| AXF42508.1       | Y DVR F SK L EQMT SGY DKV I L I ENQV VNN L DEAKV I YKKY I DQGLEGI I LK |
| AUV61060.1       | Y DVR F SK L EQMT SGY DKV I L I ENQV VNN L DEAKV I YKKY I DQGLEGI I LK |
| WP_088209698.1   | Y DVR F SK L EQMT SGY DKV I L I ENQV VNN L DEAKV I YKKY I DQGLEGI I LK |
| ATI16790.1       | Y DVR F SK L EQMT SGY DKV I L I ENQV VNN L DEAKV I YKKY I DQGLEGI I LK |
| P19088.1         | Y DVR F SK L EQMT SGY DKV I L I ENQV VNN L DEAKV I YKKY I DQGLEGI I LK |
| YP_009284262.1   | Y DVR F SK L EQMT SGY DKV I L I ENQV VNN L DEAKV I YKKY I DQGLEGI I LK |
| YP_009102401.1   | Y DVR F SK L EQMT SGY DKV I L I ENQV VNN L DEAKV I YKKY I DQGLEGI I LK |
| YP_004415092.1   | Y DVR F SK L EQMT SGY DKV I L I ENQ I VNN L DEAKV I YKKY I DQGLEGI I LK |
| AUV63060.1       | Y DVR F SK L EQMT SGY DKV I L I ENQV VNN I DEAKV I YKKY I DQGLEGI I LK |
| YP_006986754.1   | Y DVR F SK L EQMT SGC DKV I L I ENQV VNN L DEAKV I YKKY I DQGLEGI I LK |
| YP_009102671.1   | Y DVR F SK L EQMT SGY DKV I L I ENQ I VNN L DEAKV I YKKY I DQGLEGI I LK |
| BBC14820.1       | Y DVR F SK L EQMT SGY DKV I L I ENQV VNN L DEAKV I YKKY I DQGLEGI I LK |
| APU02553.1       | Y DVR F SK L EQMT SGY DKV I L I ENQV VNN L DEAKV I YKKY I DQGLEGI I LK |
| YP_009149442.1   | Y DVR F SK L EQMT SGY DKV I L I ENQV VNN L DEAKV I YKKY I DKGLEGI I LK |
| YP_002854154.1   | Y DVR F SK L EQMT SGY DKV I L I ENQV VNN L DEAKV I YKKY I DQGLEGI I LK |
| YP_009210118.1   | Y DVR F SK L EQMT SGY DKV I L I ENQV VNN L DEAKV I YKKY I DQGLEGI I LK |
| YP_009168015.1   | Y DVR F SK L EQMT SGY DKV I L I ENQV VNN L DEAKV I YKKY I DQGLEGI I LK |
| ASZ77030.1       | Y DVR F SK L EQMT SGY DKV I L I ENQV VNN L DEAKV I YKKY I DQGLEGI I LK |
| ASZ76112.1       | Y DVR F SK L EQMT SGY DKV I L I ENQL VNN L DEAKV I YKKY I DQGLEGI I LK |
| YP_009153798.1   | Y DVR F SK L EQMT SGY DKV I L I ENQL VNN L DEAKV I YKKY I DQGLEGI I LK |
| YP_009278924.1   | Y DVR F SK L EQMT SGY DKV I L I ENQV VNN L DEAKV I YKKY I DQGLEGI I LK |
| YP_007004939.1   | Y DVR F SK L EQMT SGY DKV I L I ENQV VNN L DEAKV I YKKY I DQGLEGI I LK |
| YP_009197257.1   | Y DVR F SK L EQMT SGY DKV I L I ENQV VNN L NEAKV I YKKY I DQGLEGI I LK |
| YP_002854533.1   | Y DVR F SK L EQMT SGY DKV I L I ENQV VNN L DEAKV I YKKY I DQGLEGI I LK |
| YP_007004575.1   | Y DVR F SK L EQMT SGY DKV I L I ENQV VNN L DEAKV I YKKY I DQGLEGI I LK |
| YP_009281531.1   | Y DVR F SK L EQMT SGY DKV I L I ENQV VNN L DEAKV I YKKY I DQGLEGI I LK |
| ATE86456.1       | Y DVR F SK L EQMT SGY DKV I L I ENQ I VNN L DEAKV I YKKY I DQGLEGI I LK |
| ANH49669.1       | Y DVR F SK L EQMT SGY DKV I L I ENQV VNN L DEAKV I YKKY I DQGLEGI I LK |
| YP_009111017.1   | Y DVR F SK L EQMT SGY DKV I L I ENQV VNN L DEAKV I YKKY I DQGLEGI I LK |
| AUV63745.1       | Y DVR F SK L EQMT SGY DKV I L I ENQV VNN L DEAKV I YKKY I DQGLEGI I LK |
| YP_009148639.1   | Y DVR F SK L EQMT SGY DKV I L I ENQV VNN L DEAKV I YKKY I DQGLEGI I LK |
| AWM11982.1       | Y DVR F SK L EQMT SGY DKV I L I ENQV VNN L DEAKV I YKKY I DQGLEGI I LK |
| BBC14541.1       | Y DVR F SK L EQMA SGY DKV I L I ENQV VNN L DEAKV I YKKY I DQGLEGI I LK |
| YP_803139.1      | Y DVR F SK L EQMT SGY DKV I L I ENQV VNN L DEAKV I YKKY I DQGLEGI I LK |
| AWD91739.1       | Y DVR F SK L EQMT SGY DKV I L I ENQV VNN L DEAKV I YKKY I DQGLEGI I LK |
| WP_100771463.1   | Y DVR F SK L EQMT SGY DKV I L I ENQV VNN L DEAKV I YKKY I DQGLEGI I LK |

FIG. 11 CONT.

```
                              359         369         379         389
SEQ_ID_No._1_T4      N I D G LWE N A R S K N L Y K F K E V I D V D L K I V G I Y P H R K D P T K A G G F I L E S E C G
YP_009277571.1       N I D G LWE N A R S K N L Y K F K E V I D V D L K I V G I Y P H R K D P T K A G G F I L E S E C G
AXC33998.1           N I D G LWE N A R S K N L Y K F K E V I D V D L K I V G I Y P H R K D P T K A G G F I L E S E C G
YP_009098583.1       N I D G LWE N A R S K N L Y K F K E V I D V D L K I V G I Y P H R K D P T K A G G F I L E S E C G
WP_080181510.1       N I D G LWE N A R S K N L Y K F K E V I D V D L K I V G I Y P H R K D P T K A G G F I L E S E C G
YP_009288563.1       N I D G LWE N A R S K N L Y K F K E V I D V D L K I V G I Y P H R K D P T K A G G F I L E S E C G
AUV59569.1           N I D G LWE N A R S K N L Y K F K E V I D V D L K I V G I Y P H R K D P T K A G G F I L E S E C G
YP_009180698.1       N I D G LWE N A R S K N L Y K F K E V I D V D L K I V G I Y P H R K D P T K A G G F I L E S E C G
AWD91483.1           N T D G LWE N A R S K N L Y K F K E V I D V D L K I V G I Y P H R K D P T K A G G F I L E S E C G
WP_074146536.1       N T D G LWE N A R S K N L Y K F K E V I D V D L K I V G I Y P H R K D P T K A G G F I L E S E C G
YP_009030807.1       N V D G LWE N A R S K N L Y K F K E V I D V D L K I V G I Y P H R K D P T K A G G F I L E S E C G
AXF42508.1           N I D G LWE N A R S K N L Y K F K E V I D V D L K I V G I Y P H R K D P T K A G G F I L E S E C G
AUV61060.1           N I D G LWE N A R S K N L Y K F K E V I D V D L K I V G I Y P H R K D P T K A G G F I L E S E C G
WP_088209698.1       N I D G LWE N A R S K N L Y K F K E V I D V D L K I V G I Y P H R K D P T K A G G F I L E S E C G
ATI16790.1           N I D G LWE N A R S K N L Y K F K E V I D V D L K I V G I Y P H R K D P T K A G G F I L E S E C G
P19088.1             N I D G LWE N A R S K N L Y K F K E V I D V D L K I V G I Y P H R K D P T K A G G F I L E S E C G
YP_009284262.1       N T D G LWE N A R S K N L Y K F K E V I D V D L K I V G I Y P H R K D P T K A G G F I L E S E C G
YP_009102401.1       N T D G LWE N A R S K N L Y K F K E V I D V D L K I V G I Y P H R K D P T K A G G F I L E S E C G
YP_004415092.1       N I D G LWE N A R S K N L Y K F K E V I D V D L K I V G I Y P H R K D P T K A G G F I L E S E C G
AUV63060.1           N V D G LWE N A R S K N L Y K F K E V I D V D L K I V G I Y P H R K D P T K A G G F I L E S E C G
YP_006986754.1       N I D G LWE N A R S K N L Y K F K E V I D V D L K I V G I Y P H R K D P T K A G G F I L E S E C G
YP_009102671.1       N I D G LWE N A R S K N L Y K F K E V I D V D L K I V G I Y P H R K D P T K A G G F I L E S E C G
BBC14820.1           N T D G LWE N A R S K N L Y K F K E V I D V D L K I V G I Y P H R K D P T K A G G F I L E S E C G
APU02553.1           N I D G LWE N A R S K N L Y K F K E V I D V D L K I V G I Y P H R K D P T K A G G F I L E S E C G
YP_009149442.1       N I D G LWE N A R S K N L Y K F K E V I D V D L K I V G I Y P H R K D P T K A G G F I L E S E C G
YP_002854154.1       N I D G LWE N A R S K N L Y K F K E V I D V D L K I V G I Y P H R K D P T K A G G F I L E S E C G
YP_009210118.1       N I D G LWE N A R S K N L Y K F K E V I D V D L K I V G I Y P H R K D P T K A G G F I L E S E C G
YP_009168015.1       N I D G LWE N A R S K N L Y K F K E V I D V D L K I V G I Y P H R K D P T K A G G F I L E S E C G
ASZ77030.1           N I D G LWE N T R S K N L Y K F K E V I D V D L K I V G I Y P H R K D P T K A G G F I L E S E C G
ASZ76112.1           N T D G LWE N A R S K N L Y K F K E V I D V D L K I V G I Y P H R K D P T K A G G F I L E S E C G
YP_009153798.1       N I D G LWE N A R S K N L Y K F K E V I D V D L K I V G I Y P H R K D P T K A G G F I L E S E C G
YP_009278924.1       N I D G LWE N A R S K N L Y K F K E V I D V D L K I V G I Y P H R K D P T K A G G F I L E S E C G
YP_007004939.1       N I D G LWE N A R S K N L Y K F K E V I D V D L K I V G I Y P H R K D P T K A G G F I L E S E C G
YP_009197257.1       N I D G LWE N A R S K N L Y K F K E V I D V D L K I V G I Y P H R K D P T K A G G F I L E S E C G
YP_002854533.1       N T D G LWE N A R S K N L Y K F K E V I D V D L K I V G I Y P H R K D P T K A G G F I L E S E C G
YP_007004575.1       N I D G LWE N A R S K N L Y K F K E V I D V D L K I V G I Y P H R K D P T K A G G F I L E S E C G
YP_009281531.1       N I D G LWE N A R S K N L Y K F K E V I D V D L K I V G I Y P H R K D P T K A G G F I L E S E C G
ATE86456.1           N I D G LWE N A R S K N L Y K F K E V I D V D L K I V G I Y P H R K D P T K A G G F I L E S E C G
ANH49669.1           N I D G LWE N T R S K N L Y K F K E V I D V D L K I V G I Y P H R K D P T K A G G F I L E S E C G
YP_009111017.1       N T D G LWE N A R S K N L Y K F K E V I D V D L K I V G I Y P H R K D P T K A G G F I L E S E C G
AUV63745.1           N T D G LWE N A R S K N L Y K F K E V I D V D L K I V G I Y P H R K D P T K A G G F I L E S E C G
YP_009148639.1       N T D G LWE N A R S K N L Y K F K E V I D V D L K I V G I Y P H R K D P T K A G G F I L E S E C G
AWM11982.1           N T D G LWE N A R S K N L Y K F K E V I D V D L K I V G I Y P H R K D P T K A G G F I L E S E C G
BBC14541.1           N T D G LWE N A R S K N L Y K F K E V I D V D L K I V G I Y P H R K D P T K A G G F I L E S E C G
YP_803139.1          N T D G LWE N A R S K N L Y K F K E V I D V D L K I V G I Y P H R K D P T K A G G F I L E S E C G
AWD91739.1           N T D G LWE N A R S K N L Y K F K E V I D V D L K I V G I Y P H R K D P T K A G G F I L E S E C G
WP_100771463.1       N T D G LWE N A R S K N L Y K F K E V I D V D L K I V G I Y P H R K D P T K A G G F I L E S E C G
```

FIG. 11 CONT.

|  | 409 | 419 | 429 | 439 |
| --- | --- | --- | --- | --- |
| SEQ_ID_No._1_T4 | K I K V N A G S G L K D K A G V K S H E L D R T R I M E N Q N Y Y I G K I L E C E C N G W L K S D G |
| YP_009277571.1 | K I K V N A G S G L K D K A G V K S H E L D R T R I M E N Q N Y Y I G K I L E C E C N G W L K S D G |
| AXC33998.1 | K I K V N A G S G L K D K A G V K S H E L D R T R I M E N Q N Y Y I G K I L E C E C N G W L K S D G |
| YP_009098583.1 | K I K V N A G S G L K D K A G V K S H E L D R T R I M E N Q N Y Y I G K I L E C E C N G W L K S D G |
| WP_080181510.1 | K I K V N A G S G L K D K A G V K S H E L D R T R I M E N Q N Y Y I G K I L E C E C N G W L K S D G |
| YP_009288563.1 | K I K V N A G S G L K D K A G V K S H E L D R T R I M E N Q N Y Y I G K I L E C E C N G W L K S D G |
| AUV59569.1 | K I K V N A G S G L K D K A G V K S H E L D R T R I M E N Q N Y Y I G K I L E C E C N G W L K S D G |
| YP_009180698.1 | K I K V N A G S G L K D K A G V K S H E L D R T R I M E N Q N Y Y I G K I L E C E C N G W L K S D G |
| AWD91483.1 | K I K V N A G S G L K D K A G V K S H E L D R T R I M E N Q N Y Y I G K I L E C E C N G W L K S D G |
| WP_074146536.1 | K I K V N A G S G L K D K A G V K S H E L D R T R I M E N Q N Y Y I G K I L E C E C N G W L K S D G |
| YP_009030807.1 | K I K V N A G S G L K D K A G V K S H E L D R T R I M E N Q N Y Y I G K I L E C E C N G W L K S D G |
| AXF42508.1 | K I K V N A G S G L K D K A G V K S H E L D R T R I M E N Q N Y Y I G K I L E C E C N G W L K S D G |
| AUV61060.1 | K I K V N A G S G L K D K A G V K S H E L D R T R I M E N Q N Y Y I G K I L E C E C N G W L K S D G |
| WP_088209698.1 | K I K V N A G S G L K D K A G V K S H E L D R T R I M E N Q N Y Y I G K I L E C E C N G W L K S D G |
| ATI16790.1 | K I K V N A G S G L K D K A G V K S H E L D R T R I M E N Q N Y Y I G K I L E C E C N G W L K S D G |
| P19088.1 | K I K V N A G S G L K D K A G V K S H E L D R T R I M E N Q N Y Y I G K I L E C E C N G W L K S D G |
| YP_009284262.1 | K I K V N A G S G L K D K A G V K S H E L D R T R I M E N Q N Y Y I G K I L E C E C N G W L K S D G |
| YP_009102401.1 | K I K V N A G S G L K D K A G V K S H E L D R T R I M E N Q N Y Y I G K I L E C E C N G W L K S D G |
| YP_004415092.1 | K I K V N A G S G L K D K A G V K S H E L D R T R I M E N Q N Y Y I G K I L E C E C N G W L K S D G |
| AUV63060.1 | K I K V N A G S G L K D K A G V K S H E L D R T R I M E N Q N Y Y I G K I L E C E C N G W L K S D G |
| YP_006986754.1 | K I K V N A G S G L K D K A G V K S H E L D R T R I M E N Q N Y Y I G K I L E C E C N G W L K S D G |
| YP_009102671.1 | K I K V N A G S G L K D K A G V K S H E L D R T R I M E N Q N Y Y I G K I L E C E C N G W L K S D G |
| BBC14820.1 | K I K V N A G S G L K D K A G V K S H E L D R T R I M E N Q N Y Y I G K I L E C E C N G W L K S D G |
| APU02553.1 | K I K V N A G S G L K D K A G V K S H E L D R T R I M E N Q N Y Y I G K I L E C E C N G W L K S D G |
| YP_009149442.1 | K I K V N A G S G L K D K A G V K S H E L D R T R I M E N Q N Y Y I G K I L E C E C N G W L K S D G |
| YP_002854154.1 | K I K V N A G S G L K D K A G V K S H E L D R T R I M E N Q N Y Y I G K I L E C E C N G W L K S D G |
| YP_009210118.1 | K I K V N A G S G L K D K A G V K S H E L D R T R I M E N Q N Y Y I G K I L E C E C N G W L K S D G |
| YP_009168015.1 | K I K V N A G S G L K D K A G V K S H E L D R T R I M E N Q N Y Y I G K I L E C E C N G W L K S D G |
| ASZ77030.1 | K I K V N A G S G L K D K A G V K S H E L D R T R I M E N Q N Y Y I G K I L E C E C N G W L K S D G |
| ASZ76112.1 | K I K V N A G S G L K D K A G V K S H E L D R T R I M E N Q N Y Y I G K I L E C E C N G W L K S D G |
| YP_009153798.1 | K I K V N A G S G L K D K A G V K S H E L D R T R I M E N Q N Y Y I G K I L E C E C N G W L K S D G |
| YP_009278924.1 | K I K V N A G S G L K D K A G V K S H E L D R T R I M E N Q N Y Y I G K I L E C E C N G W L K S D G |
| YP_007004939.1 | K I K V N A G S G L K D K A G V K S H E L D R T R I M E N Q N Y Y I G K I L E C E C N G W L K S D G |
| YP_009197257.1 | K I K V N A G S G L K D K A G V K S H E L D R T R I M E N Q N Y Y I G K I L E C E C N G W L K S D G |
| YP_002854533.1 | K I K V N A G S G L K D K A G I K S H E L D R T R I M E N Q N Y Y I G K I L E C E C N G W L K S D G |
| YP_007004575.1 | K I K V N A G S G L K D K A G I K S H E L D R T R I M E N Q N Y Y I G K I L E C E C N G W L K S D G |
| YP_009281531.1 | K I K V N A G S G L K D K A G I K S H E L D R T R I M E N Q N Y Y I G K I L E C E C N G W V K L D G |
| ATE86456.1 | K I K V N A G S G L K D K A G V K S H E L D R T R I M E N Q N Y Y I G K I L E C E C N G W V K L D G |
| ANH49669.1 | K I K V N A G S G L K D K A G V K S H E L D R T R I M E N Q N Y Y I G K I L E C E C N G W L K S D G |
| YP_009111017.1 | K I K V N A G S G L K D K A G V K S H E L D R T R I M E N Q N Y Y I G K I L E C E C N G W L K S D G |
| AUV63745.1 | K I K V N A G S G L K D K A G V K S H E L D R T R I M E N Q N Y Y I G K I L E C E C N G W L K S D G |
| YP_009148639.1 | K I K V N A G S G L K D K A G V K S H E L D R T R I M E N Q N Y Y I G K I L E C E C N G W L K S D G |
| AWM11982.1 | K I K V N A G S G L K D K A G V K S H E L D R T R I M E N Q N Y Y I G K I L E C E C N G W L K S D G |
| BBC14541.1 | K I K V N A G S G L K D K A G V K S H E L D R T R I M E N Q N Y Y I G K I L E C E C N G W L K S D G |
| YP_803139.1 | K I K V N A G S G L K D K A G V K S H E L D R T R I M E N Q N Y Y I G K I L E C E C N G W L K S D G |
| AWD91739.1 | K I K V N A G S G L K D K A G V K S H E L D R T R I M E N Q N Y Y I G K I L E C E C N G W L K S D G |
| WP_100771463.1 | K I K V N A G S G L K D K A G V K S H E L D R T R I M E N Q N Y Y I G K I L E C E C N G W L K S D G |

FIG. 11 CONT.

```
                        459         469         479
SEQ_ID_No._1_T4    RTDYVKLFLPIAIRLREDKTKANTFEDVFGDFHEVTGL    (SEQ ID NO:1)
YP_009277571.1     RTDYVKLFLPIAIRLREDKTKANTFEDVFGDFHEVTGL    (SEQ ID NO:2)
AXC33998.1         RTDYVKLFLPIAIRLREDKTKANTFEDVFGDFHEVTGL    (SEQ ID NO:3)
YP_009098583.1     RTDYVKLFLPIAIRLREDKTKANTFEDVFGDFHEVTGL    (SEQ ID NO:4)
WP_080181510.1     RTDYVKLFLPIAIRLREDKTKANTFEDVFGDFHEVTGL    (SEQ ID NO:5)
YP_009288563.1     RTDYVKLFLPIAIRLREDKTKANTFEDVFGDFHEVTGL    (SEQ ID NO:6)
AUV59569.1         RTDYVKLFLPIAIRLREDKTKANTFEDVFGDFHEVTGL    (SEQ ID NO:7)
YP_009180698.1     RTDYVKLFLPIAIRLREDKTKANTFEDVFGDFHEVTGL    (SEQ ID NO:8)
AWD91483.1         RTDYVKLFLPIAIRLREDKTKANTFEDVFGDFHEVTGL    (SEQ ID NO:9)
WP_074146536.1     RTDYVKLFLPIAIRLREDKTKANTFEDVFGDFHEVTGL    (SEQ ID NO:10)
YP_009030807.1     RTDYVKLFLPIAIRLREDKTKANTFEDVFGDFHEVTGL    (SEQ ID NO:11)
AXF42508.1         RTDYVKLFLPIAIRLREDKTKANTFEDVFGDFHEVTGL    (SEQ ID NO:12)
AUV61060.1         RTDYVKLFLPIAIRLREDKTKANTFEDVFGDFHEVTGL    (SEQ ID NO:13)
WP_088209698.1     RTDYVKLFLPIAIRLREDKTKANTFEDVFGDFHEVTGL    (SEQ ID NO:14)
ATI16790.1         RTDYVKLFLPIAIRLREDKTKANTFEDVFGDFHEVTGL    (SEQ ID NO:15)
P19088.1           RTDYVKLFLPIAIRLREDKTKANTFEDVFGDFHEVTGL    (SEQ ID NO:16)
YP_009284262.1     RTDYVKLFLPIAIRLREDKTKANTFEDVFGDFHEVTGL    (SEQ ID NO:17)
YP_009102401.1     RTDYVKLFLPIAIRLREDKTKANTFEDVFGDFHEVTGL    (SEQ ID NO:18)
YP_004415092.1     RTDYVKLFLPIAIRLREDKTKANTFEDVFGDFHEVTGL    (SEQ ID NO:19)
AUV63060.1         RTDYVKLFLPIAIRLREDKTKANTFEDVFGDFHEVTGL    (SEQ ID NO:20)
YP_006986754.1     RTDYVKLFLPIAIRLREDKTKANTFEDVFGDFHEVTGL    (SEQ ID NO:21)
YP_009102671.1     RTDYVKLFLPIAIRLREDKTKANTFEDVFGNFHEVTGL    (SEQ ID NO:22)
BBC14820.1         RTDYVKLFLPIAIRLREDKTKANTFEDVFGDFHEVTGL    (SEQ ID NO:23)
APU02553.1         RTDYVKLFLPIVIRLREDKTKANTFEDVFGDFHEVTGL    (SEQ ID NO:24)
YP_009149442.1     RTDYVKLFLPIAIRLREDKTKANTFEDVFGDFHEVTGL    (SEQ ID NO:25)
YP_002854154.1     RTDYVKLFLPIAIRLREDKTKANTFEDVFGDFHEVTGL    (SEQ ID NO:26)
YP_009210118.1     RTDYVKLFLPIAIRLREDKTKANTFEDVFGDFHEVTGL    (SEQ ID NO:27)
YP_009168015.1     RTDYVKLFLPIAIRLREDKTKANTFEDVFGDFHEVTGL    (SEQ ID NO:28)
ASZ77030.1         RTDYVKLFLPIAIRLREDKTKANTFEDVFGDFHEVTGL    (SEQ ID NO:29)
ASZ76112.1         RTDYVKLFLPIAIRLREDKTKANTFEDVFGDFHEVTGL    (SEQ ID NO:30)
YP_009153798.1     RTDYVKLFLPIAIRLREDKTKANTFEDVFGDFHEVTGL    (SEQ ID NO:31)
YP_009278924.1     RTDYVKLFLPIAIRLREDKTKANTFEDVFGDFHEVTGL    (SEQ ID NO:32)
YP_007004939.1     RTDYVKLFLPIAIRLREDKTKANTFEDVFGDFHEVTGL    (SEQ ID NO:33)
YP_009197257.1     RTDYVKLFLPIAIRLREDKTKANTFEDVFGDFHEVTGL    (SEQ ID NO:34)
YP_002854533.1     RTDYVKLFLPIAIRLREDKTKANTFEDVFGDFHEVTGL    (SEQ ID NO:35)
YP_007004575.1     RTDYVKLFLPIAIRLREDKTKANTFEDVFGDFHEVTGL    (SEQ ID NO:36)
YP_009281531.1     RTDYVKLFLPIAIRLREDKTKANTFEDVFGDFHEVTGL    (SEQ ID NO:37)
ATE86456.1         RTDYVKLFLPIAIRLREDKTKANTFEDLFGDFHEVTGL    (SEQ ID NO:38)
ANH49669.1         RTDYVKLFLPIAIRLREDKTKANTFEDVFGDFHEVTGL    (SEQ ID NO:39)
YP_009111017.1     RTDYVKLFLPIAIRLREDKTKANTFEDVFGDFHEVTGL    (SEQ ID NO:40)
AUV63745.1         RTDYVKLFLPIAIRLREDKTKANTFEDVFGDFHEVTGL    (SEQ ID NO:41)
YP_009148639.1     RTDYVKLFLPIVIRLREDKTKANTFEDVFGDFHEVTGL    (SEQ ID NO:42)
AWM11982.1         RTDYVKLFLPIAIRLREDKTKANTFEDVFGDFHEVTGL    (SEQ ID NO:43)
BBC14541.1         RTDYVKLFLPIAIRLREDKTKANTFEDVFGDFHEVTGL    (SEQ ID NO:44)
YP_803139.1        RTDYVKLFLPIAIRLREDKTKANTFEDVFGDFHEVTGL    (SEQ ID NO:45)
AWD91739.1         RTDYVKLFLPIAIRLREDKTKANTFEDVFGDFHEVTGL    (SEQ ID NO:46)
WP_100771463.1     RTDYVKLFLPIAIRLREDKTKANTFEDVFGDFHEVTGL    (SEQ ID NO:47)
```

FIG. 11 CONT.

excerpt of patent US 10,837,009 B1

SEQUENCE LISTING

<160> NUMBER OF SEQ ID NOS: 53

<210> SEQ ID NO 1
<211> LENGTH: 487
<212> TYPE: PRT
<213> ORGANISM: Artificial Sequence
<220> FEATURE:
<223> OTHER INFORMATION: Synthetic construct

<400> SEQUENCE: 1

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
```

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 2
<211> LENGTH: 487
<212> TYPE: PRT
<213> ORGANISM: Artificial Sequence
<220> FEATURE:
<223> OTHER INFORMATION: Synthetic construct

<400> SEQUENCE: 2

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65              70                  75                  80

Leu Thr Gly Asn Ala Ala Ile Glu Glu Leu Thr Gly Tyr Ile Thr Asp

```
                        85                  90                  95
Gly Lys Lys Asp Asp Val Glu Val Leu Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
            485

<210> SEQ ID NO 3
```

<211> LENGTH: 487
<212> TYPE: PRT
<213> ORGANISM: Artificial Sequence
<220> FEATURE:
<223> OTHER INFORMATION: Synthetic construct

<400> SEQUENCE: 3

```
Met Ile Leu Lys Ile Leu Asn Glu Ile Ala Ser Ile Gly Ser Thr Lys
  1               5                  10                  15

Gln Lys Gln Ala Ile Leu Glu Lys Asn Lys Asp Asn Glu Leu Leu Lys
             20                  25                  30

Arg Val Tyr Arg Leu Thr Tyr Ser Arg Gly Leu Gln Tyr Tyr Ile Lys
         35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Ile Gly Tyr Ile Thr Asp
                 85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Glu Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380
```

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 4
<211> LENGTH: 487
<212> TYPE: PRT
<213> ORGANISM: Artificial Sequence
<220> FEATURE:
<223> OTHER INFORMATION: Synthetic construct

<400> SEQUENCE: 4

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Asp Ala Tyr Pro Glu
225                 230                 235                 240

Ile Ser Lys Ala Lys Glu Phe Ala Glu Val Ala Glu Ser Arg Thr Ala
                245                 250                 255

```
Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Gly Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 5
<211> LENGTH: 487
<212> TYPE: PRT
<213> ORGANISM: Artificial Sequence
<220> FEATURE:
<223> OTHER INFORMATION: Synthetic construct

<400> SEQUENCE: 5

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
            35                  40                  45

Lys Trp Pro Lys Pro Gly Ile Ala Thr Gln Ser Phe Gly Met Leu Thr
        50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125
```

Leu Ile Pro Glu Gln Pro Gln Met Leu Ala Ser Ser Tyr Asp Glu Lys
130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 6
<211> LENGTH: 487
<212> TYPE: PRT
<213> ORGANISM: Artificial Sequence
<220> FEATURE:
<223> OTHER INFORMATION: Synthetic construct

<400> SEQUENCE: 6

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415
```

-continued

```
Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 7
<211> LENGTH: 487
<212> TYPE: PRT
<213> ORGANISM: Artificial Sequence
<220> FEATURE:
<223> OTHER INFORMATION: Synthetic construct

<400> SEQUENCE: 7

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
        100                 105                 110

Leu Glu Cys Gly Ala Ser Val Ser Ile Ala Asn Lys Val Trp Pro Gly
    115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Asp Pro Glu Gly Leu Asp Phe Leu Phe Asp Ala Tyr Pro Glu
225                 230                 235                 240

Ile Ser Lys Ser Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
        260                 265                 270

Glu Ala Gln Cys Met Lys Phe Gln Val Trp Asp Tyr Val Pro Leu Val
    275                 280                 285
```

Glu Ile Tyr Gly Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 8
<211> LENGTH: 487
<212> TYPE: PRT
<213> ORGANISM: Artificial Sequence
<220> FEATURE:
<223> OTHER INFORMATION: Synthetic construct

<400> SEQUENCE: 8

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 9
<211> LENGTH: 487
<212> TYPE: PRT
<213> ORGANISM: Artificial Sequence
<220> FEATURE:
<223> OTHER INFORMATION: Synthetic construct

<400> SEQUENCE: 9

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

-continued

```
Arg Val Tyr Arg Leu Thr Tyr Ser Arg Gly Leu Gln Tyr Ile Lys
             35                  40                  45
Lys Trp Pro Lys Pro Gly Ile Ala Thr Gln Ser Phe Gly Met Leu Thr
 50                  55                  60
Ile Thr Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Thr Asp
                 85                  90                  95
Gly Lys Lys Asp Asp Val Glu Val Leu Arg Arg Val Met Met Arg Asp
            100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
            130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
            210                 215                 220
Lys Lys Glu Pro Glu Gly Leu Asp Phe Leu Phe Asp Ala Tyr Pro Glu
225                 230                 235                 240
Ile Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
            275                 280                 285
Glu Ile Tyr Gly Leu Pro Ala Phe Arg Leu Lys Tyr Asp Val Arg Phe
            290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Thr Asp
            340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
            370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
```

```
                450             455             460
Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 10
<211> LENGTH: 487
<212> TYPE: PRT
<213> ORGANISM: Artificial Sequence
<220> FEATURE:
<223> OTHER INFORMATION: Synthetic construct

<400> SEQUENCE: 10

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Leu Val Asn Asn Leu Asp Glu Ala Lys Val Ile Tyr Lys
```

```
            325                 330                 335
Lys Tyr Ile Asp Gln Gly Leu Glu Gly Ile Ile Leu Lys Asn Thr Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 11
<211> LENGTH: 487
<212> TYPE: PRT
<213> ORGANISM: Artificial Sequence
<220> FEATURE:
<223> OTHER INFORMATION: Synthetic construct

<400> SEQUENCE: 11

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
```

```
              195                 200                 205
Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Leu Asp Glu Ala Lys Val Ile Tyr Lys
                325                 330                 335

Lys Tyr Ile Asp Gln Gly Leu Glu Gly Ile Ile Leu Lys Asn Val Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 12
<211> LENGTH: 487
<212> TYPE: PRT
<213> ORGANISM: Artificial Sequence
<220> FEATURE:
<223> OTHER INFORMATION: Synthetic construct

<400> SEQUENCE: 12

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Leu Thr Leu Ala Thr Arg Lys
```

```
                65                  70                  75                  80
Leu Thr Gly Asn Ala Ala Ile Glu Glu Leu Thr Gly Tyr Ile Thr Asp
                    85                  90                  95
Gly Lys Lys Asp Asp Val Glu Val Leu Arg Val Met Met Arg Asp
                100                 105                 110
Leu Glu Cys Gly Ala Ser Val Ser Ile Ala Asn Lys Val Trp Pro Gly
                115                 120                 125
Leu Ile Pro Glu Gln Pro Gln Met Leu Ala Ser Ser Tyr Asp Glu Lys
            130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                    165                 170                 175
Val Arg Leu Leu Ser Arg Ala Gly Asn Glu Tyr Leu Gly Leu Asp Leu
                180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
        210                 215                 220
Lys Lys Glu Pro Glu Gly Leu Asp Phe Leu Phe Asp Ala Tyr Pro Glu
225                 230                 235                 240
Ile Ser Lys Ala Lys Glu Phe Ala Glu Val Ala Glu Ser Arg Thr Ala
                    245                 250                 255
Ser Asn Gly Ile Ala Asn Lys Ser Leu Lys Gly Thr Ile Ser Glu Lys
                260                 265                 270
Glu Ala Gln Cys Met Lys Phe Gln Val Trp Asp Tyr Val Pro Leu Val
            275                 280                 285
Glu Ile Tyr Gly Leu Pro Val Phe Arg Leu Lys Tyr Asp Val Arg Phe
        290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                    325                 330                 335
Lys Tyr Ile Asp Gln Gly Leu Glu Gly Ile Ile Leu Lys Asn Ile Asp
                340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
        370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                    405                 410                 415
Ser His Glu Leu Asp Arg Thr Arg Ile Met Glu Asn Gln Asn Tyr Tyr
                420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
        450                 455                 460
Arg Glu Asp Lys Thr Lys Ala Asn Thr Phe Glu Asp Val Phe Gly Asp
465                 470                 475                 480
Phe His Glu Val Thr Gly Leu
                    485
```

<210> SEQ ID NO 13
<211> LENGTH: 487
<212> TYPE: PRT
<213> ORGANISM: Artificial Sequence
<220> FEATURE:
<223> OTHER INFORMATION: Synthetic construct

<400> SEQUENCE: 13

```
Met Ile Leu Lys Ile Leu Asn Lys Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365
```

```
Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 14
<211> LENGTH: 487
<212> TYPE: PRT
<213> ORGANISM: Artificial Sequence
<220> FEATURE:
<223> OTHER INFORMATION: Synthetic construct

<400> SEQUENCE: 14

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240
```

```
Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 15
<211> LENGTH: 487
<212> TYPE: PRT
<213> ORGANISM: Artificial Sequence
<220> FEATURE:
<223> OTHER INFORMATION: Synthetic construct

<400> SEQUENCE: 15

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Leu Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
                100                 105                 110
```

```
Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 16
<211> LENGTH: 487
<212> TYPE: PRT
<213> ORGANISM: Artificial Sequence
<220> FEATURE:

<223> OTHER INFORMATION: Synthetic construct

<400> SEQUENCE: 16

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala His Pro Glu
225                 230                 235                 240

Asn Ser Lys Val Lys Asp Phe Thr Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Val Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400
```

```
Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 17
<211> LENGTH: 487
<212> TYPE: PRT
<213> ORGANISM: Artificial Sequence
<220> FEATURE:
<223> OTHER INFORMATION: Synthetic construct

<400> SEQUENCE: 17

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270
```

```
Glu Ala Gln Cys Met Lys Phe Gln Val Trp Asp Tyr Val Pro Leu Val
            275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Leu Asp Glu Ala Lys Val Ile Tyr Lys
                325                 330                 335

Lys Tyr Ile Asp Gln Gly Leu Glu Gly Ile Ile Leu Lys Asn Thr Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
    435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 18
<211> LENGTH: 487
<212> TYPE: PRT
<213> ORGANISM: Artificial Sequence
<220> FEATURE:
<223> OTHER INFORMATION: Synthetic construct

<400> SEQUENCE: 18

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
    130                 135                 140
```

```
Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Gly Ile Ile Leu Lys Asn Thr Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 19
<211> LENGTH: 400
<212> TYPE: PRT
<213> ORGANISM: Artificial Sequence
<220> FEATURE:
<223> OTHER INFORMATION: Synthetic construct

<400> SEQUENCE: 19

Met Ile Leu Lys Ile Leu Asn Glu Ile Ala Ser Ile Gly Ser Thr Lys
1               5                   10                  15
```

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Lys Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Ile Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

<210> SEQ ID NO 20
<211> LENGTH: 487
<212> TYPE: PRT
<213> ORGANISM: Artificial Sequence
<220> FEATURE:
<223> OTHER INFORMATION: Synthetic construct

<400> SEQUENCE: 20

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Ile Asp Glu Ala Lys Val Ile Tyr Lys
                325                 330                 335

Lys Tyr Ile Asp Gln Gly Leu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
```

```
                        405                 410                 415
Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 21
<211> LENGTH: 487
<212> TYPE: PRT
<213> ORGANISM: Artificial Sequence
<220> FEATURE:
<223> OTHER INFORMATION: Synthetic construct

<400> SEQUENCE: 21

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
```

```
                275                 280                 285
Glu Ile Tyr Gly Leu Pro Ala Phe Arg Leu Lys Tyr Asp Val Arg Phe
290                 295                 300

Ser Lys Leu Glu Gln Met Thr Ser Gly Cys Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Val Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 22
<211> LENGTH: 487
<212> TYPE: PRT
<213> ORGANISM: Artificial Sequence
<220> FEATURE:
<223> OTHER INFORMATION: Synthetic construct

<400> SEQUENCE: 22

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Phe Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
```

```
                145                 150                 155                 160
Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
                210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Gly Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Ile Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
                450                 455                 460

Arg Glu Asp Lys Thr Lys Ala Asn Thr Phe Glu Asp Val Phe Gly Asn
465                 470                 475                 480

Phe His Glu Val Thr Gly Leu
                485

<210> SEQ ID NO 23
<211> LENGTH: 487
<212> TYPE: PRT
<213> ORGANISM: Artificial Sequence
<220> FEATURE:
<223> OTHER INFORMATION: Synthetic construct

<400> SEQUENCE: 23

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
```

-continued

```
                20                  25                  30
Arg Val Tyr Arg Leu Thr Tyr Ser Arg Gly Leu Gln Tyr Tyr Ile Lys
             35                  40                  45
Lys Trp Pro Lys Pro Gly Ile Ala Thr Gln Ser Phe Gly Met Leu Thr
 50                  55                  60
Leu Ile Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Thr Asp
                 85                  90                  95
Gly Lys Lys Asp Asp Val Glu Val Leu Arg Arg Val Met Met Arg Asp
                100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
            130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
            210                 215                 220
Lys Lys Glu Pro Glu Gly Leu Asp Phe Leu Phe Asp Ala His Pro Glu
225                 230                 235                 240
Asn Ser Lys Val Lys Asp Phe Thr Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
            275                 280                 285
Glu Ile Tyr Gly Leu Pro Ala Phe Arg Leu Lys Tyr Asp Val Arg Phe
            290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Leu Lys Asn Ile Asp
            340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
            370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Glu Cys Asn Gly Trp Leu Lys Ser Asp
            435                 440                 445
```

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 24
<211> LENGTH: 487
<212> TYPE: PRT
<213> ORGANISM: Artificial Sequence
<220> FEATURE:
<223> OTHER INFORMATION: Synthetic construct

<400> SEQUENCE: 24

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

```
Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Thr Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Val Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 25
<211> LENGTH: 487
<212> TYPE: PRT
<213> ORGANISM: Artificial Sequence
<220> FEATURE:
<223> OTHER INFORMATION: Synthetic construct

<400> SEQUENCE: 25

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190
```

```
Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Gly Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Lys Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 26
<211> LENGTH: 487
<212> TYPE: PRT
<213> ORGANISM: Artificial Sequence
<220> FEATURE:
<223> OTHER INFORMATION: Synthetic construct

<400> SEQUENCE: 26

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60
```

```
Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Ala Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
                115                 120                 125

Leu Ile Pro Glu Gln Pro Gln Met Leu Ala Ser Ser Tyr Asp Glu Lys
                130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Gly Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
                450                 455                 460

Arg Glu Asp Lys Thr Lys Ala Asn Thr Phe Glu Asp Val Phe Gly Asp
465                 470                 475                 480
```

Phe His Glu Val Thr Gly Leu
            485

<210> SEQ ID NO 27
<211> LENGTH: 487
<212> TYPE: PRT
<213> ORGANISM: Artificial Sequence
<220> FEATURE:
<223> OTHER INFORMATION: Synthetic construct

<400> SEQUENCE: 27

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Ser Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Ser Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

```
Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 28
<211> LENGTH: 487
<212> TYPE: PRT
<213> ORGANISM: Artificial Sequence
<220> FEATURE:
<223> OTHER INFORMATION: Synthetic construct

<400> SEQUENCE: 28

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Thr Glu Ala Arg Gln Ile His
            195                 200                 205

Pro Glu Gly Val Leu Ile Asp Gly Glu Leu Val Tyr His Glu Gln Val
    210                 215                 220
```

```
Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 29
<211> LENGTH: 487
<212> TYPE: PRT
<213> ORGANISM: Artificial Sequence
<220> FEATURE:
<223> OTHER INFORMATION: Synthetic construct

<400> SEQUENCE: 29

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Ile Lys
            35                  40                  45

Lys Trp Pro Lys Pro Gly Ile Ser Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95
```

```
Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 30
<211> LENGTH: 487
<212> TYPE: PRT
```

<213> ORGANISM: Artificial Sequence
<220> FEATURE:
<223> OTHER INFORMATION: Synthetic construct

<400> SEQUENCE: 30

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
        35                  40                  45

Lys Trp Pro Lys Pro Gly Ile Thr Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Leu Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Thr Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys

```
                385                 390                 395                 400
Ile Lys Val Asn Ala Gly Ser Gly Leu Lys Asp Lys Ala Gly Val Lys
                    405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu
                    485

<210> SEQ ID NO 31
<211> LENGTH: 487
<212> TYPE: PRT
<213> ORGANISM: Artificial Sequence
<220> FEATURE:
<223> OTHER INFORMATION: Synthetic construct

<400> SEQUENCE: 31

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Ile Ala Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
```

```
                260             265                 270
Glu Ala Gln Cys Met Lys Phe Gln Val Trp Asp Tyr Val Pro Leu Val
            275                 280                 285
Glu Ile Tyr Gly Leu Pro Ala Phe Arg Leu Lys Tyr Asp Val Arg Phe
            290                 295                 300
Ser Lys Leu Glu Gln Met Thr Ser Gly Tyr Asp Lys Val Ile Leu Ile
305                 310                 315                 320
Glu Asn Gln Leu Val Asn Asn Leu Asp Glu Ala Lys Val Ile Tyr Lys
                325                 330                 335
Lys Tyr Ile Asp Gln Gly Leu Glu Gly Ile Ile Leu Lys Asn Thr Asp
                340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
            370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
                420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
        450                 455                 460
Arg Glu Asp Lys Thr Lys Ala Asn Thr Phe Glu Asp Val Phe Gly Asp
465                 470                 475                 480
Phe His Glu Val Thr Gly Leu
                485

<210> SEQ ID NO 32
<211> LENGTH: 487
<212> TYPE: PRT
<213> ORGANISM: Artificial Sequence
<220> FEATURE:
<223> OTHER INFORMATION: Synthetic construct

<400> SEQUENCE: 32

Met Ile Leu Lys Ile Leu Asn Glu Ile Ala Ser Ile Gly Ser Thr Lys
1               5                   10                  15
Gln Lys Gln Ala Ile Leu Glu Lys Asn Lys Asp Asn Glu Leu Leu Lys
                20                  25                  30
Arg Val Tyr Arg Leu Thr Tyr Ser Arg Gly Leu Gln Tyr Tyr Ile Lys
            35                  40                  45
Lys Trp Pro Lys Pro Gly Ile Ala Thr Gln Ser Phe Gly Met Leu Thr
        50                  55                  60
Leu Thr Asp Met Leu Asp Phe Ile Glu Phe Thr Leu Ala Thr Arg Lys
65                  70                  75                  80
Leu Thr Gly Asn Ala Ala Ile Glu Glu Leu Thr Gly Tyr Ile Ala Asp
                85                  90                  95
Gly Lys Lys Asp Asp Val Glu Val Leu Arg Arg Val Met Met Arg Asp
                100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
```

```
                130               135               140
Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ser His Pro Glu
225                 230                 235                 240

Asn Ser Lys Val Lys Asp Phe Thr Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Val Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 33
<211> LENGTH: 487
<212> TYPE: PRT
<213> ORGANISM: Artificial Sequence
<220> FEATURE:
<223> OTHER INFORMATION: Synthetic construct

<400> SEQUENCE: 33

Met Ile Leu Lys Ile Leu Asn Glu Ile Ala Ser Ile Gly Ser Thr Lys

```
  1               5                   10                  15
Gln Lys Gln Ala Ile Leu Glu Lys Asn Lys Asp Asn Glu Leu Leu Lys
                20                  25                  30
Arg Val Tyr Arg Leu Thr Tyr Ser Arg Gly Leu Gln Tyr Tyr Ile Lys
                35                  40                  45
Lys Trp Pro Lys Pro Gly Ile Ala Thr Gln Ser Phe Gly Met Leu Thr
                50                  55                  60
Leu Thr Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Ala Asp
                85                  90                  95
Gly Lys Lys Asp Asp Val Glu Val Leu Arg Arg Val Met Met Arg Asp
                100                 105                 110
Leu Glu Cys Gly Ala Ser Val Ser Ile Ala Asn Lys Val Trp Pro Gly
                115                 120                 125
Leu Ile Pro Glu Gln Pro Gln Met Leu Ala Ser Tyr Asp Glu Lys
                130                 135                 140
Gly Ile Ser Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
                180                 185                 190
Leu Lys Glu Glu Leu Ile Lys Met Thr Ala Glu Ala Arg Gln Ile His
                195                 200                 205
Pro Glu Gly Val Leu Ile Asp Gly Glu Leu Val Tyr His Glu Gln Val
                210                 215                 220
Glu Lys Glu Pro Glu Gly Leu Asp Phe Leu Phe Asp Ala Tyr Pro Glu
225                 230                 235                 240
Ile Ser Lys Ala Lys Glu Phe Ala Glu Val Ala Glu Ser Arg Thr Thr
                245                 250                 255
Ser Asn Gly Ile Ala Asn Lys Ser Leu Lys Gly Thr Ile Ser Glu Lys
                260                 265                 270
Glu Ala Gln Cys Met Lys Phe Gln Val Trp Asp Tyr Val Pro Leu Val
                275                 280                 285
Glu Ile Tyr Gly Leu Pro Ala Phe Arg Leu Lys Tyr Asp Val Arg Phe
                290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
                340                 345                 350
Gly Leu Trp Glu Asn Ala Arg Ser Lys Asn Leu Tyr Lys Phe Lys Glu
                355                 360                 365
Val Ile Asp Val Asp Leu Lys Ile Val Gly Ile Tyr Pro His Arg Lys
                370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
                420                 425                 430
```

```
Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 34
<211> LENGTH: 487
<212> TYPE: PRT
<213> ORGANISM: Artificial Sequence
<220> FEATURE:
<223> OTHER INFORMATION: Synthetic construct

<400> SEQUENCE: 34

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Val Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
290                 295                 300
```

```
Ser Lys Leu Glu Gln Met Thr Ser Gly Tyr Asp Lys Val Ile Leu Ile
305                 310                 315                 320

Glu Asn Gln Val Val Asn Asn Leu Asn Glu Ala Lys Val Ile Tyr Lys
            325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
            485

<210> SEQ ID NO 35
<211> LENGTH: 487
<212> TYPE: PRT
<213> ORGANISM: Artificial Sequence
<220> FEATURE:
<223> OTHER INFORMATION: Synthetic construct

<400> SEQUENCE: 35

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
            85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175
```

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Ile Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 36
<211> LENGTH: 487
<212> TYPE: PRT
<213> ORGANISM: Artificial Sequence
<220> FEATURE:
<223> OTHER INFORMATION: Synthetic construct

<400> SEQUENCE: 36

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

-continued

```
Lys Trp Pro Lys Pro Asp Ile Ala Thr Gln Ser Phe Gly Met Leu Thr
 50                  55                  60
Ile Thr Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Thr Asp
                 85                  90                  95
Gly Lys Lys Asp Asp Val Glu Val Leu Arg Arg Val Met Met Arg Asp
                100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
130                 135                 140
Gly Ile Ser Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
                180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
210                 215                 220
Lys Lys Glu Pro Glu Gly Leu Asp Phe Leu Phe Asp Ala Tyr Pro Glu
225                 230                 235                 240
Ile Ser Lys Ala Lys Glu Phe Ala Glu Val Ala Glu Ser Arg Thr Thr
                245                 250                 255
Ser Asn Gly Ile Ala Asn Lys Ser Leu Lys Gly Thr Ile Ser Glu Lys
                260                 265                 270
Glu Ala Gln Cys Met Lys Phe Gln Val Trp Asp Tyr Val Pro Leu Val
            275                 280                 285
Glu Ile Tyr Gly Leu Pro Ala Phe Arg Leu Lys Tyr Asp Val Arg Phe
290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Thr Asp
                340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
                420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
450                 455                 460
```

```
Arg Glu Asp Lys Thr Lys Ala Asn Thr Phe Glu Asp Val Phe Gly Asp
465                 470                 475                 480

Phe His Glu Val Thr Gly Leu
            485
```

<210> SEQ ID NO 37
<211> LENGTH: 487
<212> TYPE: PRT
<213> ORGANISM: Artificial Sequence
<220> FEATURE:
<223> OTHER INFORMATION: Synthetic construct

<400> SEQUENCE: 37

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Ala Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Gly Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335
```

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Ile Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Val Lys Leu Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 38
<211> LENGTH: 487
<212> TYPE: PRT
<213> ORGANISM: Artificial Sequence
<220> FEATURE:
<223> OTHER INFORMATION: Synthetic construct

<400> SEQUENCE: 38

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Thr Glu Ala Arg Gln Ile His
        195                 200                 205

```
Pro Glu Gly Val Leu Ile Asp Gly Glu Leu Val Tyr His Glu Gln Val
210                 215                 220

Glu Lys Glu Pro Glu Gly Leu Asp Phe Leu Phe Asp Ala Tyr Pro Glu
225                 230                 235                 240

Ile Ser Lys Ala Lys Glu Phe Ala Glu Val Ala Glu Ser Arg Thr Thr
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Gly Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Ile Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
370                 375                 380

Asp Pro Thr Lys Ala Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Val Lys Leu Asp
                435                 440                 445

Gly Arg Thr Asp Tyr Val Lys Leu Phe Leu Pro Ile Ala Ile Arg Leu
                450                 455                 460

Arg Glu Asp Lys Thr Lys Ala Asn Thr Phe Glu Asp Leu Phe Gly Asp
465                 470                 475                 480

Phe His Glu Val Thr Gly Leu
                485

<210> SEQ ID NO 39
<211> LENGTH: 488
<212> TYPE: PRT
<213> ORGANISM: Artificial Sequence
<220> FEATURE:
<223> OTHER INFORMATION: Synthetic construct

<400> SEQUENCE: 39

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
                35                  40                  45

Lys Trp Pro Lys Pro Gly Ile Ala Thr Gln Ser Phe Gly Met Leu Thr
            50                  55                  60

Ile Thr Asp Met Leu Asp Phe Ile Glu Phe Thr Leu Ala Thr Arg Lys
65              70                  75                  80
```

```
Leu Thr Gly Asn Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asn Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Val Tyr His Glu Gln
            210                 215                 220

Val Glu Lys Glu Pro Glu Gly Leu Asp Phe Leu Phe Asp Ala Tyr Pro
225                 230                 235                 240

Glu Ile Ser Lys Ala Lys Glu Phe Ala Glu Val Ala Glu Ser Arg Thr
                245                 250                 255

Thr Ser Asn Gly Ile Ala Asn Lys Ser Leu Lys Gly Thr Ile Ser Glu
                260                 265                 270

Lys Glu Ala Gln Cys Met Lys Phe Gln Val Trp Asp Tyr Val Pro Leu
            275                 280                 285

Val Glu Ile Tyr Gly Leu Pro Ala Phe Arg Leu Lys Tyr Asp Val Arg
            290                 295                 300

Phe Ser Lys Leu Glu Gln Met Thr Ser Gly Tyr Asp Lys Val Ile Leu
305                 310                 315                 320

Ile Glu Asn Gln Val Val Asn Asn Leu Asp Glu Ala Lys Val Ile Tyr
                325                 330                 335

Lys Lys Tyr Ile Asp Gln Gly Leu Glu Gly Ile Ile Leu Lys Asn Ile
                340                 345                 350

Asp Gly Leu Trp Glu Asn Ala Arg Ser Lys Asn Leu Tyr Lys Phe Lys
            355                 360                 365

Glu Val Ile Asp Val Asp Leu Lys Ile Val Gly Ile Tyr Pro His Arg
            370                 375                 380

Lys Asp Pro Thr Lys Ala Gly Gly Phe Ile Leu Glu Ser Glu Cys Gly
385                 390                 395                 400

Lys Ile Lys Val Asn Ala Gly Ser Gly Leu Lys Asp Lys Ala Gly Val
                405                 410                 415

Lys Ser His Glu Leu Asp Arg Thr Arg Ile Met Glu Asn Gln Asn Tyr
            420                 425                 430

Tyr Ile Gly Lys Ile Leu Glu Cys Glu Cys Asn Gly Trp Leu Lys Ser
            435                 440                 445

Asp Gly Arg Thr Asp Tyr Val Lys Leu Phe Leu Pro Ile Ala Ile Arg
            450                 455                 460

Leu Arg Glu Asp Lys Thr Lys Ala Asn Thr Phe Glu Asp Val Phe Gly
465                 470                 475                 480

Asp Phe His Glu Val Thr Gly Leu
                485
```

```
<210> SEQ ID NO 40
<211> LENGTH: 486
<212> TYPE: PRT
<213> ORGANISM: Artificial Sequence
<220> FEATURE:
<223> OTHER INFORMATION: Synthetic construct

<400> SEQUENCE: 40

Met Ile Leu Lys Ile Leu Asn Glu Ile Ala Ser Ile Gly Ser Thr Lys
1               5                   10                  15

Gln Lys Gln Ala Ile Leu Glu Lys Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Asp Ala Pro Glu Ile
225                 230                 235                 240

Ser Lys Ala Lys Glu Phe Ala Glu Val Ala Glu Ser Arg Thr Ala Ser
                245                 250                 255

Asn Gly Ile Ala Asn Lys Ser Leu Lys Gly Thr Ile Ser Glu Lys Glu
            260                 265                 270

Ala Gln Cys Met Lys Phe Gln Val Trp Asp Tyr Val Pro Leu Val Glu
        275                 280                 285

Ile Tyr Gly Leu Pro Ala Phe Arg Leu Lys Tyr Asp Val Arg Phe Ser
    290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Ile Asp Gly
            340                 345                 350

Leu Trp Glu Asn Thr Arg Ser Lys Asn Leu Tyr Lys Phe Lys Glu Val
        355                 360                 365

Ile Asp Val Asp Leu Lys Ile Val Gly Ile Tyr Pro His Arg Lys Asp
```

```
                    370                 375                 380
Pro Thr Lys Ala Gly Gly Phe Ile Leu Glu Ser Glu Cys Lys Ile
385                 390                 395                 400

Lys Val Asn Ala Gly Ser Gly Leu Lys Asp Lys Ala Gly Val Lys Ser
                    405                 410                 415

His Glu Leu Asp Arg Thr Arg Ile Met Glu Asn Gln Asn Tyr Tyr Ile
                420                 425                 430

Gly Lys Ile Leu Glu Cys Glu Cys Asn Gly Trp Leu Lys Ser Asp Gly
            435                 440                 445

Arg Thr Asp Tyr Val Lys Leu Phe Leu Pro Ile Ala Ile Arg Leu Arg
        450                 455                 460

Glu Asp Lys Thr Lys Ala Asn Thr Phe Glu Asp Val Phe Gly Asp Phe
465                 470                 475                 480

His Glu Val Thr Gly Leu
                    485

<210> SEQ ID NO 41
<211> LENGTH: 486
<212> TYPE: PRT
<213> ORGANISM: Artificial Sequence
<220> FEATURE:
<223> OTHER INFORMATION: Synthetic construct

<400> SEQUENCE: 41

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Asp Ala Pro Glu Ile
225                 230                 235                 240

Ser Lys Ala Lys Glu Phe Ala Glu Val Ala Glu Ser Arg Thr Ala Ser
```

```
                    245                 250                 255
Asn Gly Ile Ala Asn Lys Ser Leu Lys Gly Thr Ile Ser Glu Lys Glu
            260                 265                 270

Ala Gln Cys Met Lys Phe Gln Val Trp Asp Tyr Val Pro Leu Val Glu
            275                 280                 285

Ile Tyr Gly Leu Pro Ala Phe Arg Leu Lys Tyr Asp Val Arg Phe Ser
            290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Thr Asp Gly
                340                 345                 350

Leu Trp Glu Asn Ala Arg Ser Lys Asn Leu Tyr Lys Phe Lys Glu Val
            355                 360                 365

Ile Asp Val Asp Leu Lys Ile Val Gly Ile Tyr Pro His Arg Lys Asp
            370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                405                 410                 415

His Glu Leu Asp Arg Thr Arg Ile Met Glu Asn Gln Asn Tyr Tyr Ile
            420                 425                 430

Gly Lys Ile Leu Glu Cys Glu Cys Asn Gly Trp Leu Lys Ser Asp Gly
            435                 440                 445

Arg Thr Asp Tyr Val Lys Leu Phe Leu Pro Ile Ala Ile Arg Leu Arg
            450                 455                 460

Glu Asp Lys Thr Lys Ala Asn Thr Phe Glu Asp Val Phe Gly Asp Phe
465                 470                 475                 480

His Glu Val Thr Gly Leu
                485

<210> SEQ ID NO 42
<211> LENGTH: 486
<212> TYPE: PRT
<213> ORGANISM: Artificial Sequence
<220> FEATURE:
<223> OTHER INFORMATION: Synthetic construct

<400> SEQUENCE: 42

Met Ile Leu Lys Ile Leu Asn Glu Ile Ala Ser Ile Gly Ser Thr Lys
1               5                   10                  15

Gln Lys Gln Ala Ile Leu Glu Arg Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
            50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
```

```
                115                 120                 125
Leu Ile Pro Glu Gln Pro Gln Met Leu Ala Ser Ser Tyr Asp Glu Lys
        130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Pro Glu Ile
225                 230                 235                 240

Ser Lys Ala Lys Glu Phe Ala Glu Val Ala Glu Ser Arg Thr Thr Ser
                245                 250                 255

Asn Gly Ile Ala Asn Lys Ser Leu Lys Gly Thr Ile Ser Glu Lys Glu
            260                 265                 270

Ala Gln Cys Met Lys Phe Gln Val Trp Asp Tyr Val Pro Leu Val Glu
        275                 280                 285

Ile Tyr Gly Leu Pro Ala Phe Arg Leu Lys Tyr Asp Val Arg Phe Ser
    290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Thr Asp Gly
            340                 345                 350

Leu Trp Glu Asn Ala Arg Ser Lys Asn Leu Tyr Lys Phe Lys Glu Val
        355                 360                 365

Ile Asp Val Asp Leu Lys Ile Val Gly Ile Tyr Pro His Arg Lys Asp
    370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                405                 410                 415

His Glu Leu Asp Arg Thr Arg Ile Met Glu Asn Gln Asn Tyr Tyr Ile
            420                 425                 430

Gly Lys Ile Leu Glu Cys Glu Cys Asn Gly Trp Leu Lys Ser Asp Gly
        435                 440                 445

Arg Thr Asp Tyr Val Lys Leu Phe Leu Pro Ile Val Ile Arg Leu Arg
    450                 455                 460

Glu Asp Lys Thr Lys Ala Asn Thr Phe Glu Asp Val Phe Gly Asp Phe
465                 470                 475                 480

His Glu Val Thr Gly Leu
                485

<210> SEQ ID NO 43
<211> LENGTH: 486
<212> TYPE: PRT
<213> ORGANISM: Artificial Sequence
<220> FEATURE:
<223> OTHER INFORMATION: Synthetic construct
```

```
<400> SEQUENCE: 43

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Ile Thr Asp Met Leu Asp Phe Ile Glu Phe Thr Leu Ala Thr Arg Lys
65              70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Thr Pro Glu Ile
225                 230                 235                 240

Ser Lys Ala Lys Asp Phe Thr Glu Val Ala Glu Ser Arg Thr Ala Ser
                245                 250                 255

Asn Gly Ile Ala Asn Lys Ser Leu Lys Gly Thr Ile Ser Glu Lys Glu
            260                 265                 270

Ala Gln Cys Met Lys Phe Gln Val Trp Asp Tyr Val Pro Leu Val Glu
        275                 280                 285

Ile Tyr Gly Leu Pro Ala Phe Arg Leu Lys Tyr Asp Val Arg Phe Ser
    290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Thr Asp Gly
            340                 345                 350

Leu Trp Glu Asn Ala Arg Ser Lys Asn Leu Tyr Lys Phe Lys Glu Val
        355                 360                 365

Ile Asp Val Asp Leu Lys Ile Val Gly Ile Tyr Pro His Arg Lys Asp
    370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                405                 410                 415
```

```
His Glu Leu Asp Arg Thr Arg Ile Met Glu Asn Gln Asn Tyr Tyr Ile
            420                 425                 430

Gly Lys Ile Leu Glu Cys Glu Cys Asn Gly Trp Leu Lys Ser Asp Gly
            435                 440                 445

Arg Thr Asp Tyr Val Lys Leu Phe Leu Pro Ile Ala Ile Arg Leu Arg
450                 455                 460

Glu Asp Lys Thr Lys Ala Asn Thr Phe Glu Asp Val Phe Gly Asp Phe
465                 470                 475                 480

His Glu Val Thr Gly Leu
                485

<210> SEQ ID NO 44
<211> LENGTH: 486
<212> TYPE: PRT
<213> ORGANISM: Artificial Sequence
<220> FEATURE:
<223> OTHER INFORMATION: Synthetic construct

<400> SEQUENCE: 44

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
            50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
            210                 215                 220

Glu Lys Glu Pro Glu Gly Leu Asp Phe Leu Phe Asp Ala Pro Glu Ile
225                 230                 235                 240

Ser Lys Ala Lys Glu Phe Ala Glu Val Ala Glu Ser Arg Thr Ala Ser
                245                 250                 255

Asn Gly Ile Ala Asn Lys Ser Leu Lys Gly Thr Ile Ser Glu Lys Glu
            260                 265                 270

Ala Lys Cys Met Lys Phe Gln Val Trp Asp Tyr Val Pro Leu Val Glu
            275                 280                 285
```

Ile Tyr Gly Leu Pro Ala Phe Arg Leu Lys Tyr Asp Val Arg Phe Ser
    290                 295                 300

Lys Leu Glu Gln Met Ala Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Thr Asp Gly
                340                 345                 350

Leu Trp Glu Asn Ala Arg Ser Lys Asn Leu Tyr Lys Phe Lys Glu Val
            355                 360                 365

Ile Asp Val Asp Leu Lys Ile Val Gly Ile Tyr Pro His Arg Lys Asp
        370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                405                 410                 415

His Glu Leu Asp Arg Thr Arg Ile Met Glu Asn Gln Asn Tyr Tyr Ile
                420                 425                 430

Gly Lys Ile Leu Glu Cys Glu Cys Asn Gly Trp Leu Lys Ser Asp Gly
            435                 440                 445

Arg Thr Asp Tyr Val Lys Leu Phe Leu Pro Ile Ala Ile Arg Leu Arg
        450                 455                 460

Glu Asp Lys Thr Lys Ala Asn Thr Phe Glu Asp Val Phe Gly Asp Phe
465                 470                 475                 480

His Glu Val Thr Gly Leu
                485

<210> SEQ ID NO 45
<211> LENGTH: 486
<212> TYPE: PRT
<213> ORGANISM: Artificial Sequence
<220> FEATURE:
<223> OTHER INFORMATION: Synthetic construct

<400> SEQUENCE: 45

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

```
Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Ser Glu Gly Leu Asp Phe Leu Phe Asp Thr Pro Glu Ile
225                 230                 235                 240

Ser Lys Ala Lys Asp Phe Thr Glu Val Ala Glu Ser Arg Thr Ala Ser
            245                 250                 255

Asn Gly Ile Ala Asn Lys Ser Leu Lys Gly Thr Ile Ser Glu Lys Glu
        260                 265                 270

Ala Gln Cys Met Lys Phe Gln Val Trp Asp Tyr Val Pro Leu Val Glu
    275                 280                 285

Val Tyr Gly Leu Pro Ala Phe Arg Leu Lys Tyr Asp Val Arg Phe Ser
290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
            325                 330                 335

Tyr Ile Asp Gln Gly Leu Glu Gly Ile Ile Leu Lys Asn Thr Asp Gly
        340                 345                 350

Leu Trp Glu Asn Ala Arg Ser Lys Asn Leu Tyr Lys Phe Lys Glu Val
    355                 360                 365

Ile Asp Val Asp Leu Lys Ile Val Gly Ile Tyr Pro His Arg Lys Asp
370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
            405                 410                 415

His Glu Leu Asp Arg Thr Arg Ile Met Glu Gln Asn Tyr Tyr Ile
        420                 425                 430

Gly Lys Ile Leu Glu Cys Glu Cys Asn Gly Trp Leu Lys Ser Asp Gly
    435                 440                 445

Arg Thr Asp Tyr Val Lys Leu Phe Leu Pro Ile Ala Ile Arg Leu Arg
450                 455                 460

Glu Asp Lys Thr Lys Ala Asn Thr Phe Glu Asp Val Phe Gly Asp Phe
465                 470                 475                 480

His Glu Val Thr Gly Leu
            485

<210> SEQ ID NO 46
<211> LENGTH: 486
<212> TYPE: PRT
<213> ORGANISM: Artificial Sequence
<220> FEATURE:
<223> OTHER INFORMATION: Synthetic construct

<400> SEQUENCE: 46

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30
```

```
Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
 50                  55                  60

Ile Thr Asp Met Leu Asp Phe Ile Glu Phe Thr Leu Ala Thr Arg Lys
 65              70                  75                      80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
             100                 105                 110

Leu Glu Cys Gly Ala Ser Val Ser Ile Ala Asn Lys Val Trp Pro Gly
         115                 120                 125

Leu Ile Pro Glu Gln Pro Gln Met Leu Ala Ser Ser Tyr Asp Glu Lys
         130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                 165                 170                 175

Val Arg Leu Leu Ser Arg Ala Gly Asn Glu Tyr Leu Gly Leu Asp Leu
             180                 185                 190

Leu Lys Glu Glu Leu Ile Lys Met Thr Ala Glu Ala Arg Gln Ile His
         195                 200                 205

Pro Glu Gly Val Leu Ile Asp Gly Glu Leu Val Tyr His Glu Gln Val
         210                 215                 220

Glu Lys Glu Pro Glu Gly Leu Asp Phe Leu Phe Asp Ala Pro Glu Ile
225                 230                 235                 240

Ser Lys Ala Lys Glu Val Ala Glu Val Ala Glu Ser Arg Thr Ala Ser
                 245                 250                 255

Asn Gly Ile Ala Asn Lys Ser Leu Lys Gly Thr Ile Ser Glu Lys Glu
             260                 265                 270

Ala Lys Cys Met Lys Phe Gln Val Trp Asp Tyr Val Pro Leu Val Glu
         275                 280                 285

Ile Tyr Gly Leu Pro Ala Phe Arg Leu Lys Tyr Asp Val Arg Phe Ser
         290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                 325                 330                 335

Tyr Ile Asp Gln Gly Leu Glu Gly Ile Ile Leu Lys Asn Thr Asp Gly
             340                 345                 350

Leu Trp Glu Asn Ala Arg Ser Lys Asn Leu Tyr Lys Phe Lys Glu Val
         355                 360                 365

Ile Asp Val Asp Leu Lys Ile Val Gly Ile Tyr Pro His Arg Lys Asp
         370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                 405                 410                 415

His Glu Leu Asp Arg Thr Arg Ile Met Glu Asn Gln Asn Tyr Tyr Ile
             420                 425                 430

Gly Lys Ile Leu Glu Cys Glu Cys Asn Gly Trp Leu Lys Ser Asp Gly
         435                 440                 445
```

```
Arg Thr Asp Tyr Val Lys Leu Phe Pro Ile Ala Ile Arg Leu Arg
            450                 455                 460

Glu Asp Lys Thr Lys Ala Asn Thr Phe Glu Asp Val Phe Gly Asp Phe
465                 470                 475                 480

His Glu Val Thr Gly Leu
                485

<210> SEQ ID NO 47
<211> LENGTH: 486
<212> TYPE: PRT
<213> ORGANISM: Artificial Sequence
<220> FEATURE:
<223> OTHER INFORMATION: Synthetic construct

<400> SEQUENCE: 47

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
    50                  55                  60

Ile Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Ser Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Glu Lys Glu Pro Glu Gly Leu Asp Phe Leu Phe Gly Thr Pro Glu Ile
225                 230                 235                 240

Ser Lys Ala Lys Glu Phe Ala Glu Val Ala Glu Ser Arg Thr Ala Ser
                245                 250                 255

Asn Gly Ile Ala Asn Lys Ser Leu Lys Gly Thr Ile Ser Glu Lys Glu
            260                 265                 270

Ala Lys Cys Met Lys Phe Gln Val Trp Asp Tyr Val Pro Leu Val Glu
        275                 280                 285

Ile Tyr Gly Leu Pro Ala Phe Arg Leu Lys Tyr Asp Val Arg Phe Ser
    290                 295                 300

Lys Leu Glu Gln Met Thr Ser Gly Tyr Asp Lys Val Ile Leu Ile Glu
305                 310                 315                 320
```

Asn Gln Val Val Asn Asn Leu Asp Glu Ala Lys Val Ile Tyr Lys Lys
            325                 330                 335

Tyr Ile Asp Gln Gly Leu Glu Gly Ile Ile Leu Lys Asn Thr Asp Gly
        340                 345                 350

Leu Trp Glu Asn Ala Arg Ser Lys Asn Leu Tyr Lys Phe Lys Glu Val
    355                 360                 365

Ile Asp Val Asp Leu Lys Ile Val Gly Ile Tyr Pro His Arg Lys Asp
370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
            405                 410                 415

His Glu Leu Asp Arg Thr Arg Ile Met Glu Asn Gln Asn Tyr Tyr Ile
        420                 425                 430

Gly Lys Ile Leu Glu Cys Glu Cys Asn Gly Trp Leu Lys Ser Asp Gly
    435                 440                 445

Arg Thr Asp Tyr Val Lys Leu Phe Leu Pro Ile Ala Ile Arg Leu Arg
    450                 455                 460

Glu Asp Lys Thr Lys Ala Asn Thr Phe Glu Asp Val Phe Gly Asp Phe
465                 470                 475                 480

His Glu Val Thr Gly Leu
            485

<210> SEQ ID NO 48
<211> LENGTH: 46
<212> TYPE: DNA
<213> ORGANISM: Artificial Sequence
<220> FEATURE:
<223> OTHER INFORMATION: Synthetic construct

<400> SEQUENCE: 48
gatccttaga tagtatactg agttctgtaa acgagctatt gaattc                    46

<210> SEQ ID NO 49
<211> LENGTH: 42
<212> TYPE: DNA
<213> ORGANISM: Artificial Sequence
<220> FEATURE:
<223> OTHER INFORMATION: Synthetic construct

<400> SEQUENCE: 49
gaattcaata gctcgtttac agaactcagt atactatcta ag                        42

<210> SEQ ID NO 50
<211> LENGTH: 37
<212> TYPE: DNA
<213> ORGANISM: Artificial Sequence
<220> FEATURE:
<223> OTHER INFORMATION: Synthetic construct

<400> SEQUENCE: 50
aaatctaagc cacaacgccg aggcaaacgg atggctc                              37

<210> SEQ ID NO 51
<211> LENGTH: 37
<212> TYPE: DNA
<213> ORGANISM: Artificial Sequence
<220> FEATURE:
<223> OTHER INFORMATION: Synthetic construct

<400> SEQUENCE: 51

```
gagccatccg tttgcctcgg cgttgtggct tagattt                                37

<210> SEQ ID NO 52
<211> LENGTH: 29
<212> TYPE: DNA
<213> ORGANISM: Artificial Sequence
<220> FEATURE:
<223> OTHER INFORMATION: Synthetic construct

<400> SEQUENCE: 52
gatgggacct acaatgtacc agaagcgtc                                         29

<210> SEQ ID NO 53
<211> LENGTH: 30
<212> TYPE: DNA
<213> ORGANISM: Artificial Sequence
<220> FEATURE:
<223> OTHER INFORMATION: Synthetic construct

<400> SEQUENCE: 53
gacgcttctg gtacattgta ggtcccatct                                        30
```

DNA LIGASE VARIANTS

CROSS REFERENCE

This application claims right of priority to U.S. provisional application Ser. No. 62/609,577 filed Dec. 22, 2017.

BACKGROUND

DNA ligases facilitate the joining of DNA strands together by catalyzing the formation of a phosphodiester bond between 3' hydroxyl ends of one polynucleotide, and the 5' phosphorylated end of another (1, 2). Ligases play a key role in genome integrity by repairing single-strand breaks in duplex DNA in living organisms. Some ligases, such as T4 DNA ligase, depend on ATP while other ligases, such as E. coli ligase and Taq ligase, utilize NAD as an energy source. Some ligases, notably T4 DNA ligase, can also join multiple dsDNA fragments together at fully base paired (blunt) ends or at ends with short complementary single stranded overhangs (cohesive ends, sticky ends) (1-4). End-joining activity is generally enhanced at high concentrations of ligase or in the presence of molecular crowding agents, most typically PEG-6000 or PEG-8000 (5-7). DNA ligases have found great utility in molecular biology and diagnostic applications, including restriction enzyme cloning (8), adaptor ligation for high-throughput DNA sequencing, and several methods for assembling large DNA fragments from multiple smaller fragments (9-11).

While DNA ligases are most efficient at joining DNA substrates with correct Watson-crick paired overhangs, DNA ligases can also make fidelity errors and join DNA with non-complementary overhangs. Few DNA ligases have been described that can efficiently carry out end-joining in high salt buffers or at elevated temperatures (12). DNA ligases have been isolated from various sources and selected for use according to their naturally occurring properties. Examples of ligases used for different purposes include those isolated from thermostable organisms such as archaea and thermostable bacteria, which can efficiently ligate nicks at elevated temperature (13, 14). Other DNA ligases have been isolated from plant viruses such as PBCV-1 and from bacterial viruses such as T3 and T7 phages, and have substrate specificity and salt tolerance that vary from T4 DNA ligase (12, 15, 16).

The DNA ligase from bacteriophage T4 is the ligase most commonly used in laboratory research. It can ligate cohesive or "sticky" ends of DNA, oligonucleotides, as well as some RNA and RNA-DNA hybrids, but not single-stranded nucleic acids (17-25). It can also ligate blunt-ended DNA with high efficiency (20, 26). Unlike E. coli DNA ligase, T4 DNA ligase cannot utilize NAD and it has an absolute requirement for ATP as a cofactor. T4 DNA ligase is typically active between 4° C. and 37° C. and loses activity rapidly above this temperature. T4 DNA ligase is also sensitive to buffer additives such as monovalent salts, which inhibit activity, especially end-joining activity. For certain applications, it would be useful to have a T4 DNA ligase variant that can carry out the DNA end-joining reaction under non-standard conditions.

SUMMARY

In general, in one embodiment, a variant DNA ligase, is provided where the ligase has (i) an amino acid sequence that has at least 80% sequence identity to SEQ ID NO:1; and (ii) an amino acid substitution at one or more positions corresponding to positions 19, 63, 140, 142, 145, 155, 213, 292, 293, 299, 318, 327, 358, 363, 427, 445, 446, 455, 461, 462 and 466 of SEQ ID NO: 1. Examples of the embodiment include the following: The variant bacteriophage DNA ligase may include an amino acid substitution at two or more positions, for example at five or more positions, or for example at ten or more positions. The ligase may include one or more of the following amino acids substitutions selected from Q19L, L63Q, S140P, D142S, G145K, F155Y, L213M, S292G, L293K, K299P, I318R, N327S, A358G, A358K, L363Q, E427A, L445V, A461I, I462K and E466I wherein the amino acid substitutions are at positions that correspond to positions in SEQ ID NO:1. The ligase may be a fusion protein, or a chimera of two or more ligases.

Other examples include the following:

The variant bacteriophage DNA ligase, as a result of the one or more amino acid substitutions, has increased stability at 45° C., 50° C. and/or 55° C. relative to the T4 DNA ligase of SEQ ID NO:1.

The variant bacteriophage DNA ligase of described above, as a result of the one or more amino acid substitutions, has increased activity in a buffer comprising NaCl or KCl.

The variant bacteriophage DNA ligase has increased activity in a buffer comprising 250 mM salt.

The variant bacteriophage DNA ligase has increased activity in a buffer comprising 300 mM, 400 mM and/or 500 mM relative to the T4 DNA ligase of SEQ ID NO:1.

The variant bacteriophage DNA ligase comprises an amino acid sequence that has at least 90% sequence identity to SEQ ID NO:1.

In general, in one aspect, a composition may include a variant bacteriophage DNA ligase as described above; and a buffering agent.

In general, in one embodiment, a kit is provided that includes a variant bacteriophage DNA ligase as described above; and a reaction buffer.

In general in another aspect, a method is provided for ligating a nucleic acid molecule, that includes: combining variant bacteriophage DNA ligase with a first polynucleotide and a second polynucleotide to produce a reaction mix; and incubating the reaction mix to permit the variant DNA ligase to ligate the 5' end of the first polynucleotide to the 3' end of the second polynucleotide.

In one example, the incubating is done at a temperature of at least 45° C. In another example, the reaction mix includes salt at a concentration of at least 20 mM. In another aspect, the ends of the DNA for ligation are selected from the group consisting of 5' overhangs of any length, 3' overhangs of any length, and blunt ends.

In general, in one aspect, a DNA ligase is provided that includes the following features:
 (i) an amino acid sequence that is at least 80% identical to SEQ ID NO:1; and
 (ii) one or more amino acid substitutions at positions corresponding to positions 142, 145, 155, 292, 318, 327, 358, 363 and 445 in SEQ ID NO:1;
   wherein if the substitution is at a position corresponding to position 292, the amino acid substitution is not Glycine; and
   wherein if the substitution is at a position corresponding to position 358 then the amino acid substitution is not an alanine or threonine.

Various embodiments include one or more of the following additional features:

The ligase may include a substitution at a position corresponding to position 358.

The ligase may include at least one, or at least two, additional substitutions.

The at least one or two additional substitutions may be selected from a position corresponding to 12, 19, 23, 35, 41, 42, 43, 50, 63, 66, 71, 89, 99, 108, 119, 121, 127, 140, 142, 145, 149, 155, 175, 178, 192, 199, 210, 213, 270, 272, 275, 284, 288, 289, 290, 292, 293, 294, 295, 299, 301, 302, 306, 309, 310, 311, 312, 318, 323, 324, 327, 333, 339, 351, 353, 363, 375, 387, 393, 426, 427, 429, 439, 445, 446, 456, 461, 462, 466, 476 in SEQ ID NO:1.

Any of the ligase variants described above may include an amino acid sequence that is at least 90% or 95% identical to SEQ ID NO:1. Any of the ligase variants described above may include one or more, or two or more, or five or more, or ten or more additional amino acid substitutions at positions corresponding to any of the positions listed above or for example corresponding to positions 19, 63, 140, 142, 213, 292, 293, 299, 318, 327, 358, 445, 455, 461, 462 and 466 in SEQ ID NO:1, for example Q19L, L63Q, S140P, D142S, G145K, F155Y, L213M, S292G, L293K, K299P, I318R, N327S A358K, A358G, L363Q L445V, L455V, A461I, I462K, E466I, and E466W, wherein the amino acid substitutions are at positions corresponding to positions in SEQ ID NO:1.

The ligase variants described above may have increased stability at 45° C., 50° C. and/or 55° C. and/or may have increased activity in a buffer comprising NaCl or KCl, these properties being relative to that of the T4 DNA ligase of SEQ ID NO:1.

The ligase variants described above may have increased activity in a buffer comprising 250 mM, 300 mM, 400 mM and/or 500 mM salt relative to the T4 DNA ligase of SEQ ID NO:1.

The features of a ligase variant as described above may additionally include the following:

The ligase variants may be a fusion protein. Examples of fusion partners include maltose binding domain, chitin binding domain or SNAP-Tag® (New England Biolabs, Ipswich, Mass.).

The ligase variant may be immobilized on or in a matrix. Examples of matrices include beads, columns, and plastics.

The ligase variant may be incorporated in a droplet for manipulation in a microfluidic device or on a surface which receives an electrical current that controls the motion of the droplet (Umapathi et al. et al., (2018) MRS Advances, 3(26), 1475-1483. doi:10.1557/adv.2018.331).

The ligase variant may be lyophilized for storage or may be contained in a storage buffer for an extended shelf life.

The ligase variants may be combined with a buffering agent such as a storage buffer or a reaction buffer.

The ligase variants may be combined with a ligation enhancer.

The ligase variants may be combined with a crowding agent such as Ficoll, dextran or Polyethylene glycol (PEG) of varying sizes.

The ligase variants may be purified in a buffer that is DNA free

The ligase variants may be purified in a buffer that is RNA free.

The ligase variants may be combined with a DNA substrate and/or other enzymes.

The ligase variants may have a shelf life in a buffer of at least one year or at least 2 years wherein the activity of the variant is not diminished or is diminished by no more than 10%. The temperature of storage may be at a temperature of at least one of room temperature, 4° C., −20° C. or −70° C.

The ligase variants may be used in a workflow suitable for generating DNA libraries, for example, genomic libraries (see for example New England Biolabs, Ipswich, Mass.).

The ligase variants may be used to prepare a sample for sequencing (see for example NEBNext® (New England Biolabs, Ipswich, Mass.).

The ligase variants may be used in gene assembly or DNA synthesis such as Golden Gate assembly, Gibson assembly and NEBuilder® assembly, for example, as provided by New England Biolabs Ipswich, Mass.

Any of the above ligases or preparations thereof may be contained in a kit with instructions for use.

In general, in one aspect, a method is provided for ligating polynucleotides that includes:
(a) combining any of the DNA ligases or variants thereof exemplified above with a first polynucleotide and a second polynucleotide to produce a reaction mix; and
(b) incubating the reaction mix to permit the DNA ligase to ligate the 5' end of the first polynucleotide to the 3' end of the second polynucleotide.

Various embodiments include one or more of the following additional features:

The incubating may be done at a temperature of at least 45° C.

The reaction mix may include a salt at a concentration of at least 20 mM.

The ends of the DNA in the ligation may be selected from the group consisting of 5' overhangs of any length, 3' overhangs of any length, and blunt ends.

$$norm\, S_{mut} = \frac{avA_{mut} - avA_{WT}}{St Dev_{WT}}$$

where norm $S_{mut}$ is the normalized stability score of the mutant, av $A_{mut}$ is the average fraction of ligation product formed by the mutant av $A_{wt}$ is the average fraction of ligation product formed by wild-type T4 DNA Ligase.

StDev$_{wt}$ is the standard deviation of replicates (>3 independent experiments) for wild-type T4 DNA Ligase.

Figure 2:
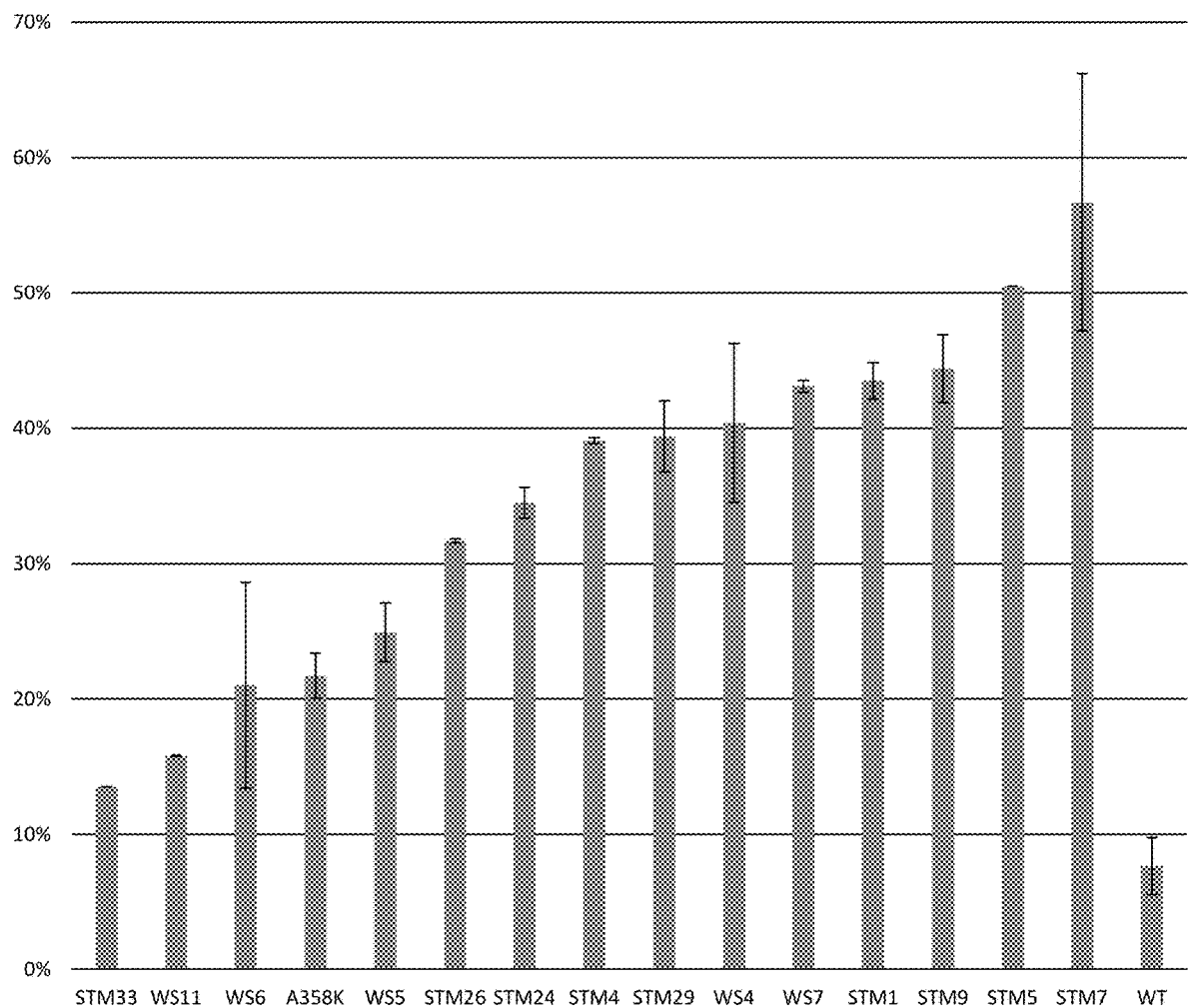

FIG. 2 shows percent (%) ligation product formed from polynucleotides with a 5'GATC overhang when ligation was performed in the presence of 250 mM KCl. 15 different nickel-resin purified his-tagged T4 DNA ligase mutants each having a plurality of mutations (described in Example 2) are shown here to have improved ligation efficiency compared to wild-type T4 DNA ligase (WT).

Figure 3:
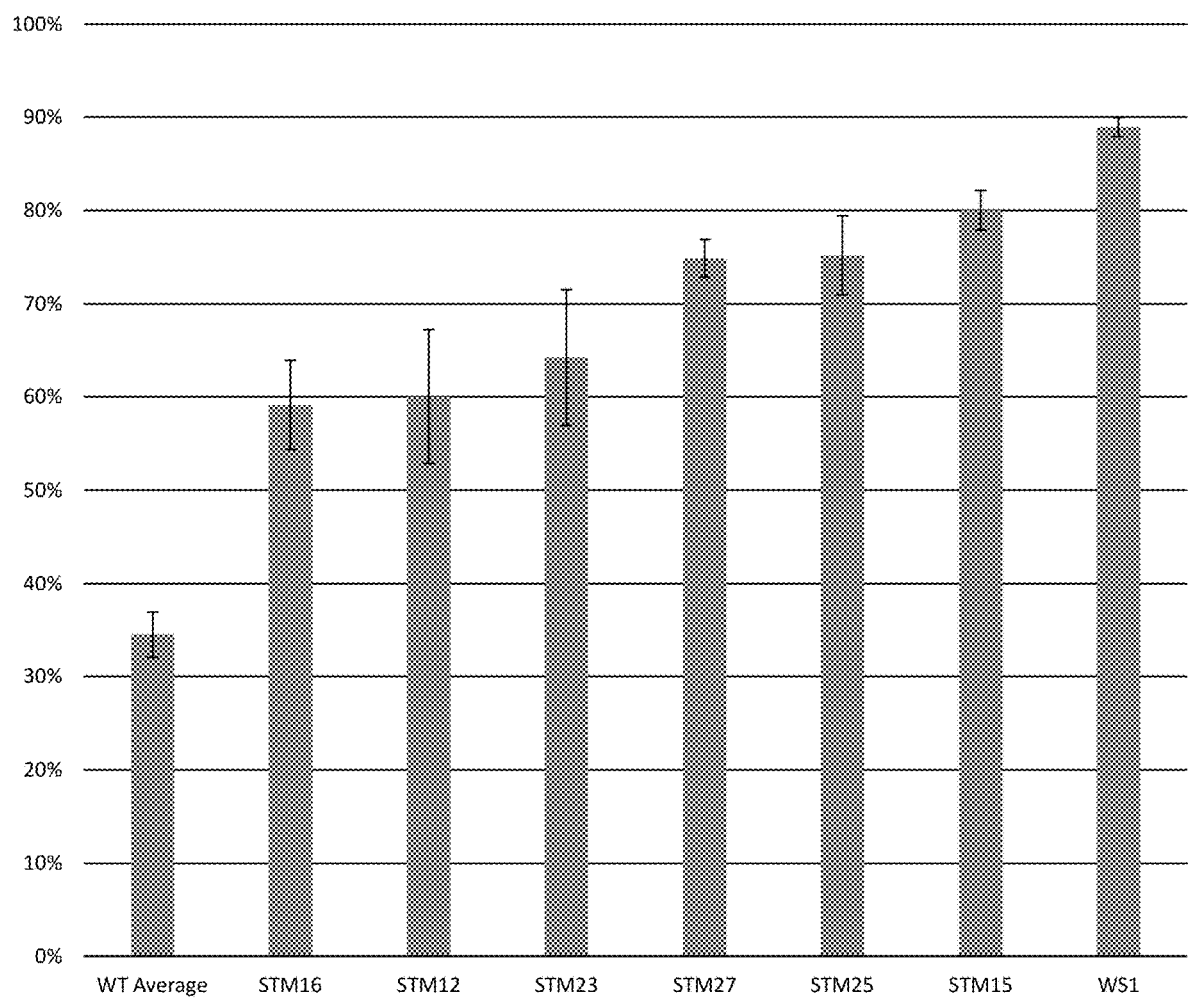

FIG. 3 shows the percent (%) of ligation products formed using purified T4 DNA ligase mutants described in Example 3 in the presence of 250 mM salt. Purified mutants and wild-type (WT) were used to ligate polynucleotides with a 4-base overhang, as described in Example 2.

Figure 4:
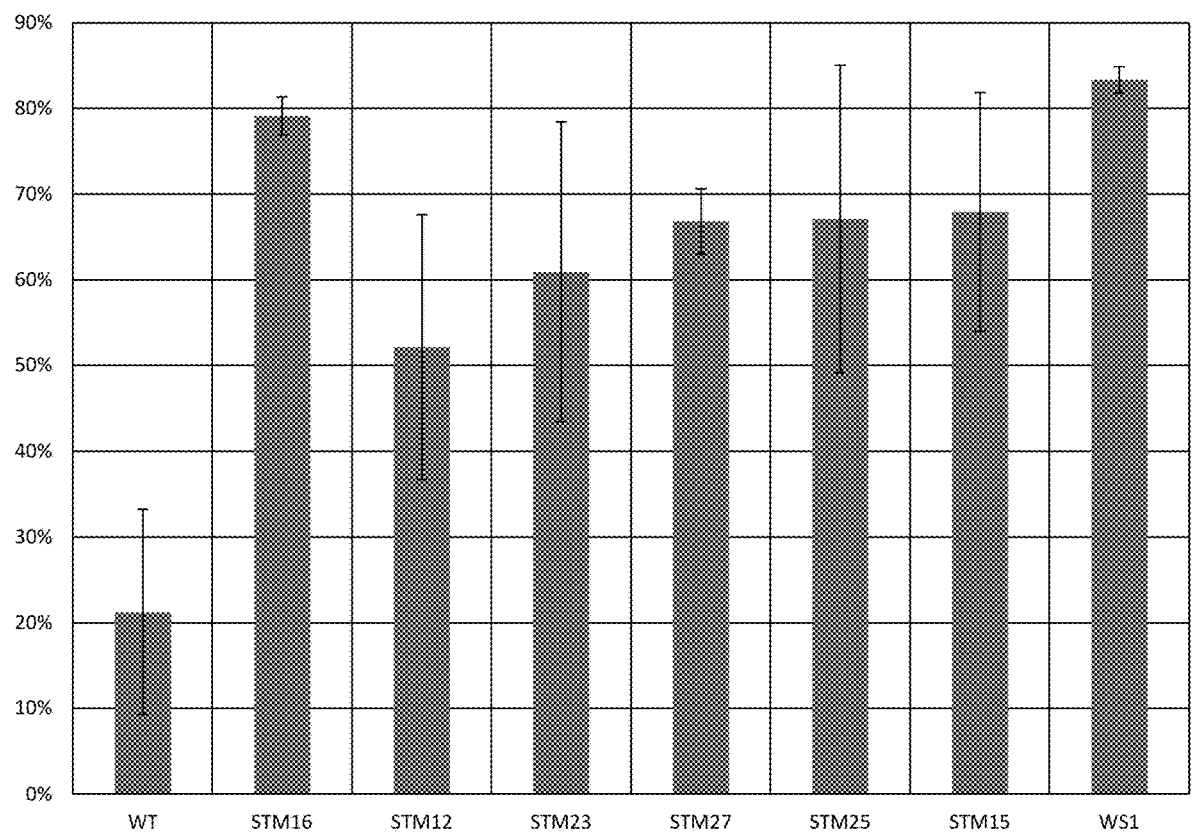

FIG. 4 shows the percent (%) of ligation products of 7 purified mutant and wild-type (WT) T4 DNA ligases (described in Example 2) in 400 mM KCl where the substrate is a double stranded DNA with a single-stranded 5'GATC overhang.

Figure 5:
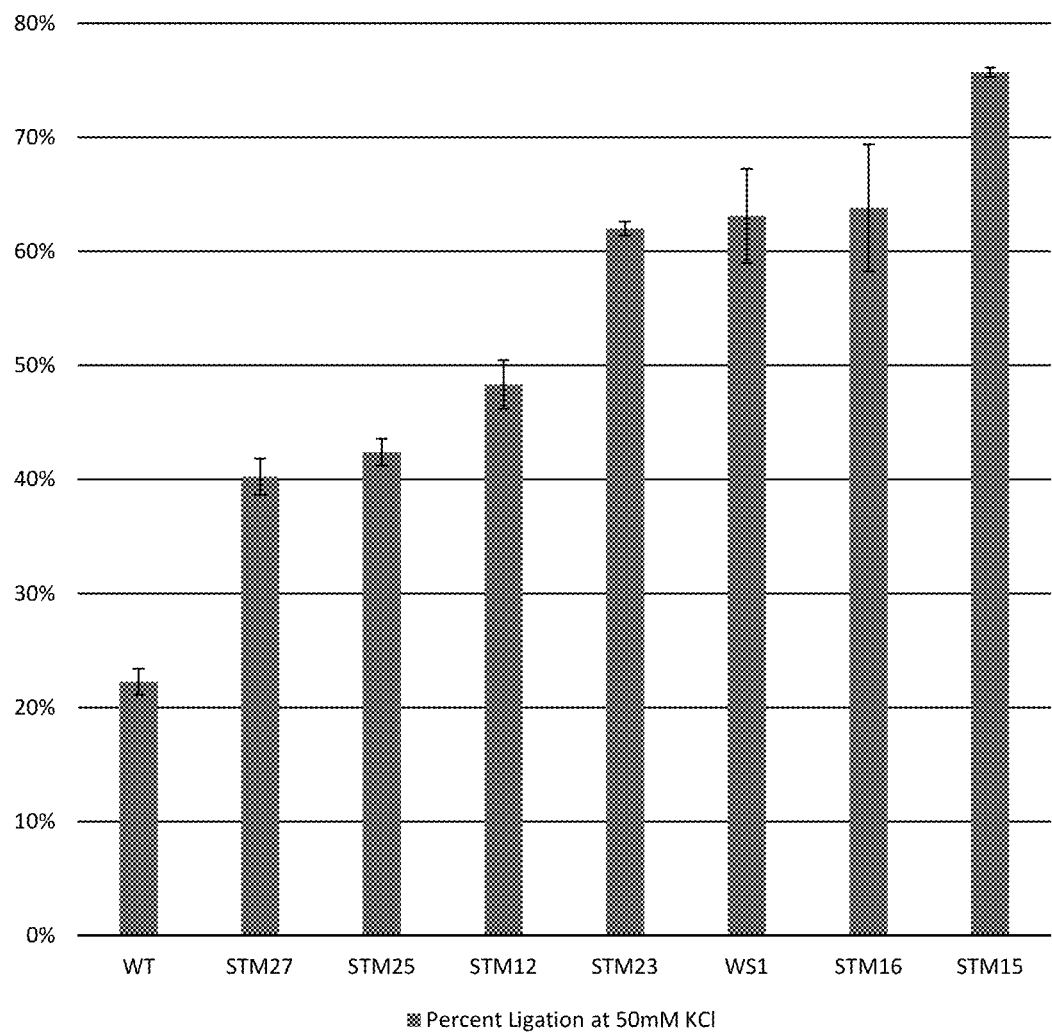

FIG. 5 shows the percent ligation of T/A substrate with 50 mM additional KCl in Ultra II FS buffer, as described in Example 3.

Figure 1:
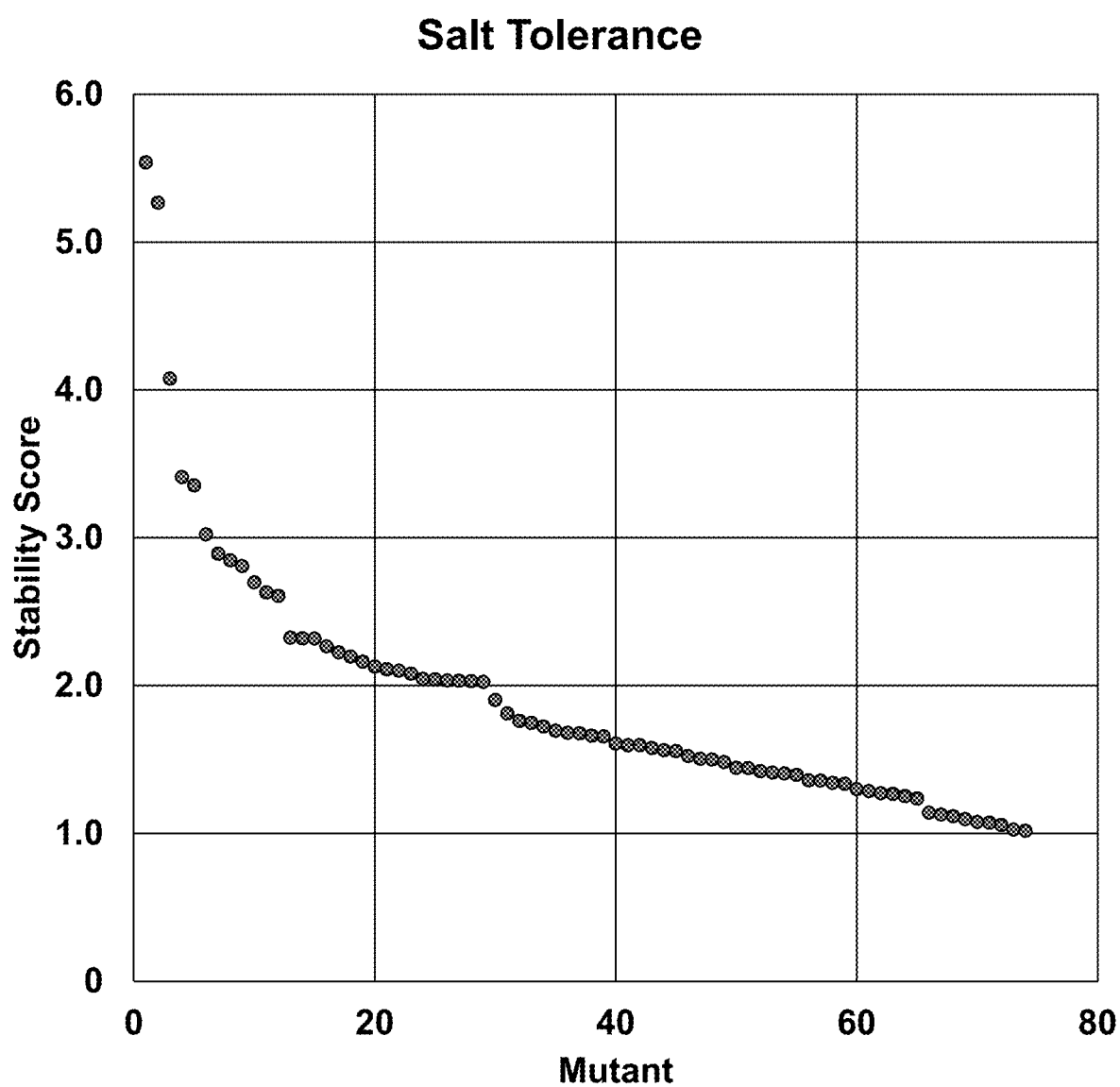
FIG. 1 shows the improvement in salt tolerance for each of 74 different T4 DNA Ligase variants in the presence of 300 mM KCl at 25° C. for a 15 minute incubation compared with wild-type T4 DNA ligase, where each variant (1-74) has one mutation selected from (in order of high activity to lower activity but all activities being greater than wild-type under the same conditions): A358K, G145K, I318R, L363Q, Q19L, G145T, N327S, I462K, D142S, I121T, E466I, G42K, L192K, L445V, N149K, E210N, D175G, K199E, E427A, Q429R, G42Q, I121L, V333D, Q309K, Q429K, F155Y, G145A, I318E, K306V, V108I, G145L, T387K, Y284I, M62S, Q309E, L192D, Q323R, I351P, T387H, E23K, K299P, I393V, F71L, V288N, P127K, V333E, T66Q, A295E, E466W, M310L, V302E, Q275V, V333A, D301K, P294T, K306R, Q309S, Q323T, C439I, E466R, D476E, P294I, V324I, M426W, E289V, P294V, P294D, G42R, Q275S, G353A, K272N, T311A, P294K, Q275R. Each mutant was assayed for ligation activity of a double stranded (ds) DNA with a single strand (ss) 5'GATC overhang created by BamHI cleavage (N4 overhang) in the presence of 300 mM KCl at 25° C. for 15 minutes (as described in Example 1), and a normalized stability score was calculated as follows.
Figure 6:
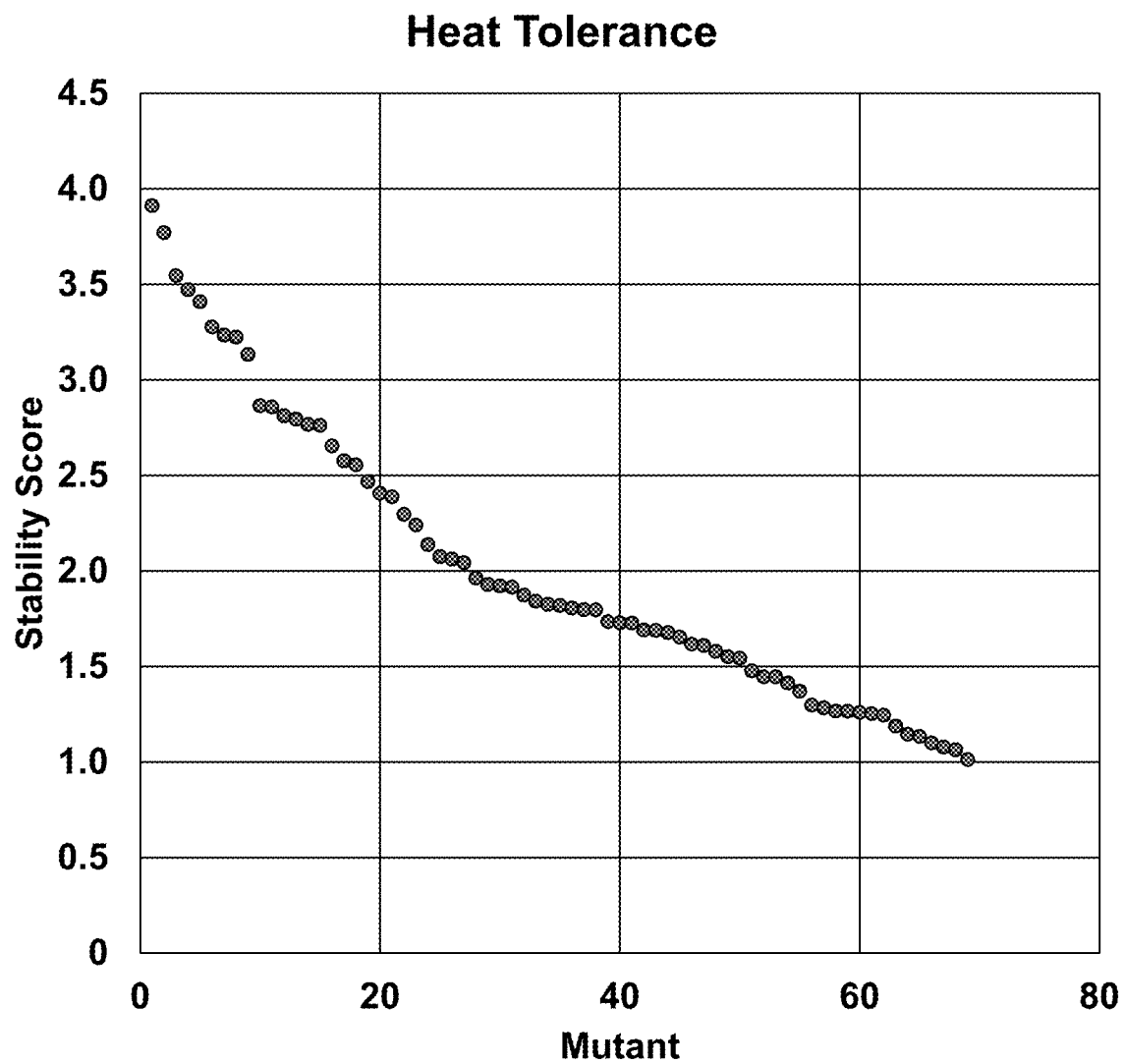

FIG. 6 shows the heat tolerance of each of 69 different T4 DNA Ligase variants (1-69) where each variant had one mutation selected from the group (in order of higher activity to lower activity all of which showed higher activity than wild-type) The ligase variants were incubated at 50° C. for 3.5 minutes and remaining ligase activity on a nucleic acid with a 4-base overhang was measured at 25° C. for 15 minutes, as described in Example 1. A normalized heat stability score was calculated as described in FIG. 1. Mutant set consisted of: A358G, S292G, K299P, L293K, I462K, A461I, L445V, L213M, L293R, L293E, A358K, S140P, L293N, D301K, D476E, R178K, V333K, V302E, Q323T, F155Y, Q19L, E466I, M426W, V324I, E427A, K306Q, K99P, D301E, Q309K, L293D, I12A, T387K, G42K, L192D, T311V, E89A, M62S, K455S, S270T, Q309A, I339R, Q429K, Y35F, R178S, N327S, K306R, W50F, V108I, K306M, C439V, I290V, V119A, A295K, L431, D142S, Q309E, R178N, Q429R, K306I, K375R, A295P, I12T, R41P, C439I, L192K, T66Q, Q275A, S312E, and V333A.

Figure 7:
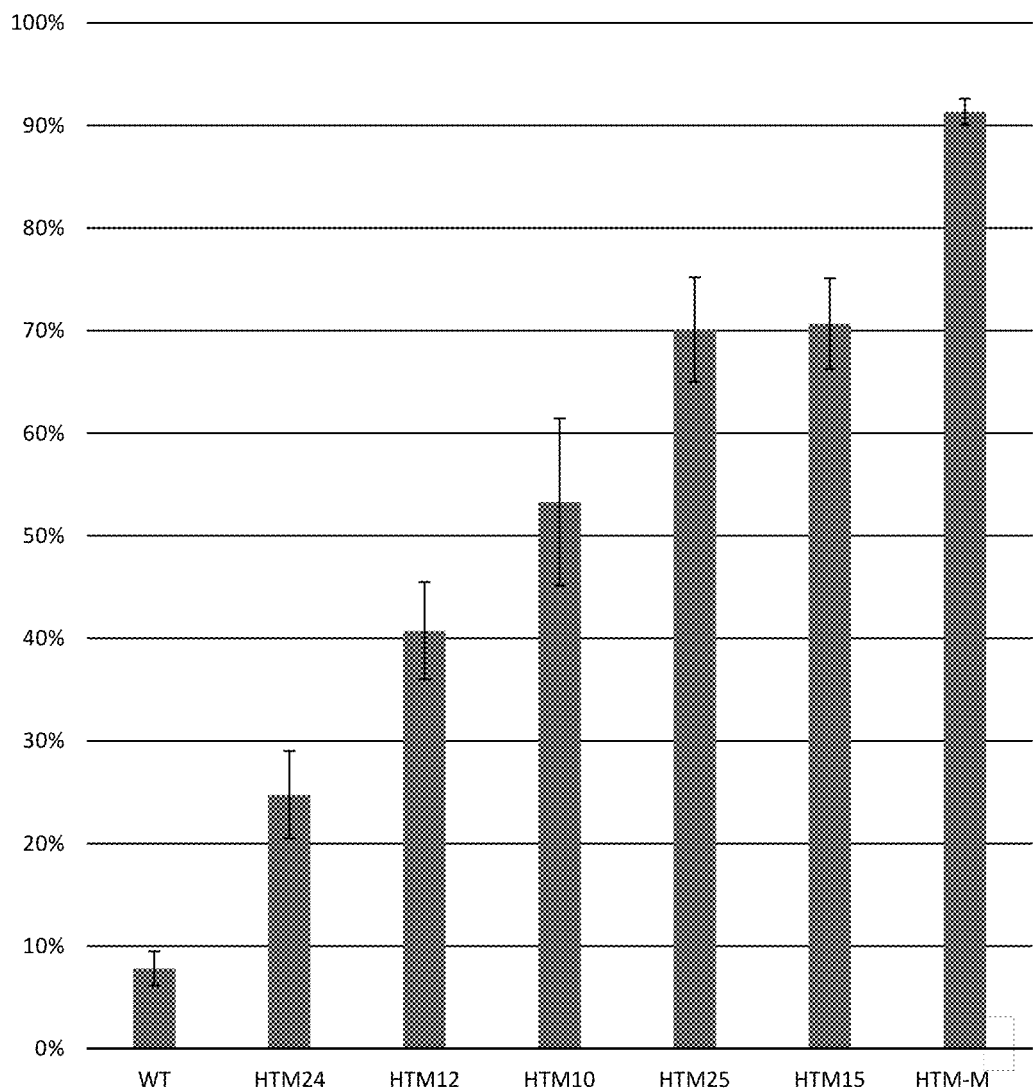

FIG. 7 shows the fraction of ligation product formed between polynucleotides with complementary 4-base overhangs at 52° C. after a 5 minute incubation using wild-type (WT) T4 DNA ligase and mutants, as described Example 4. The remaining ligase activity was measured at 25° C. for 15 minutes.

Figure 8:
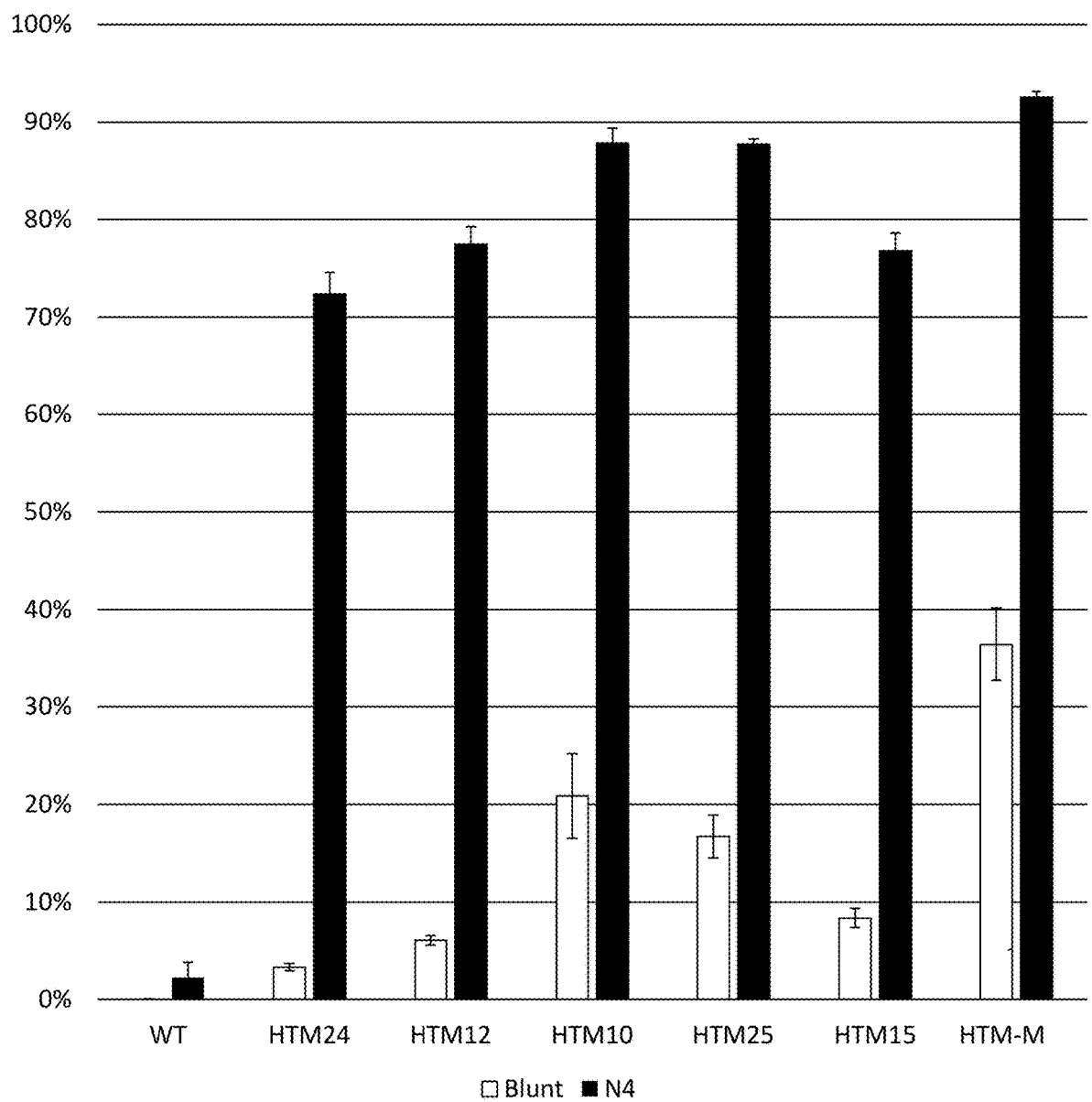

FIG. 8 shows the percentage of ligation product formed between (a) polynucleotides with complementary N4 overhangs at 50° C. for 15 minutes; and (b) polynucleotides with blunt ends; using wild-type T4 DNA ligase and mutants, as described in Example 5.

Figure 9A:
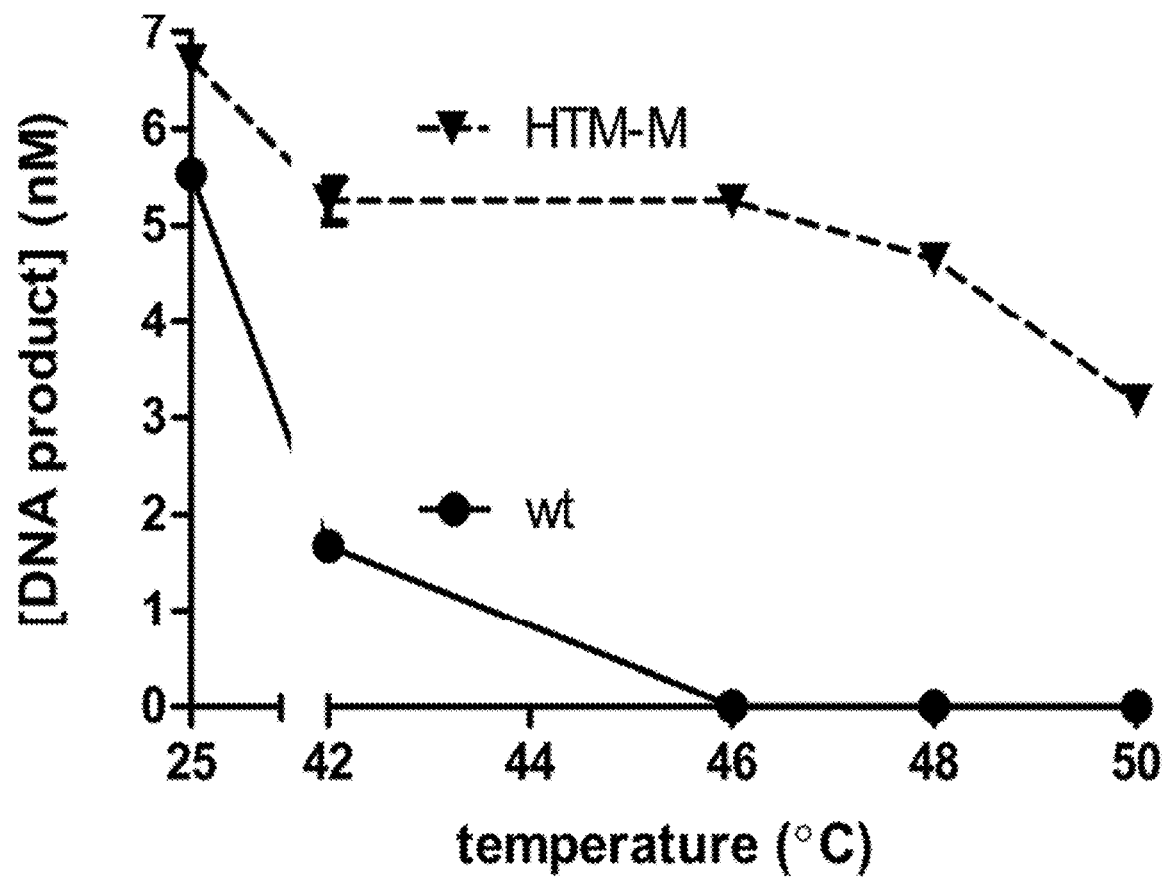
Figure 9B:
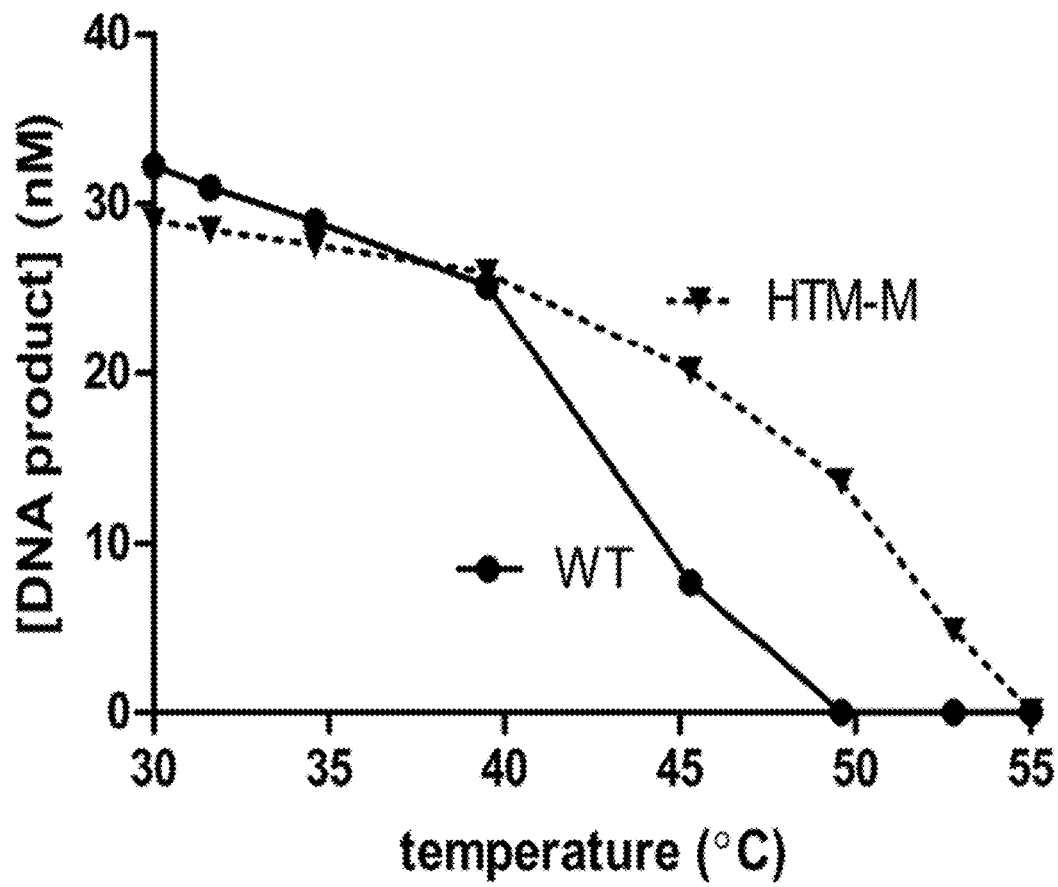

FIG. 9A-9B shows the results of blunt end ligation after heating (FIG. 9A) or at elevated temperatures (FIG. 9B) comparing a T4 DNA ligase variant (HTM-M) with wild-type T4 DNA ligase.

FIG. 9A shows the heat stability of HTM-M up to 50° C. when the ligase is incubated for 60 minutes at the stated temperatures followed by a ligation reaction at 25° C. for 15 minutes. A 60 minute ligation at raised temperatures destroys the activity of wt T4 DNA ligase by 44° C. whereas the activity of the T4 DNA ligase variant is hardly affected.

FIG. 9B shows the efficiency of ligation at raised temperatures of a T4 DNA ligase variant compared to the wt T4 DNA ligase. The activity of the wild-type T4 DNA ligase is completely lost at 50° C. whereas the ligation efficiency of the variant is reduced but remains active. Divergence of efficiency of ligation at raised temperatures is seen from 40° C.

Figure 10:
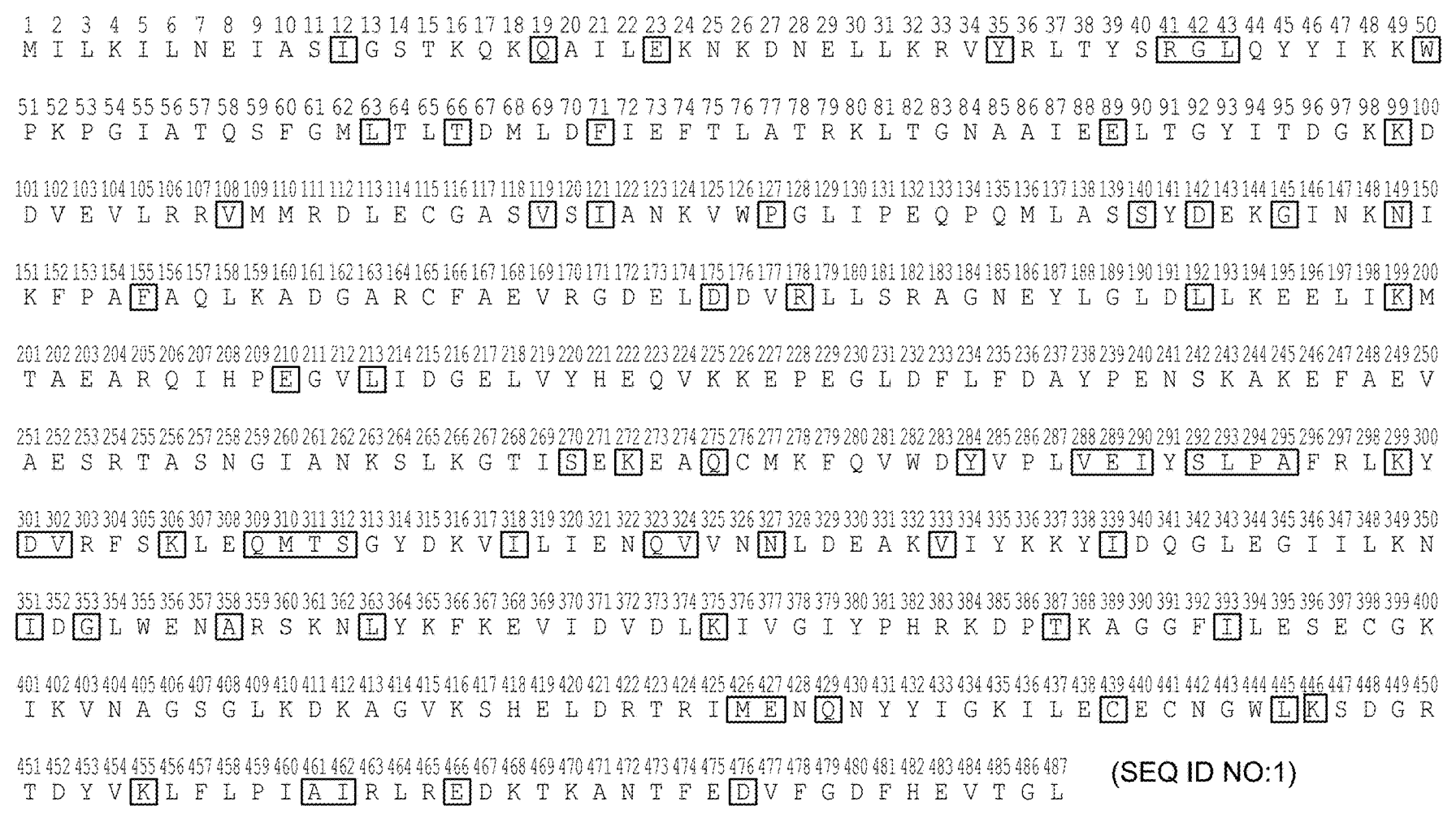

FIG. 10 shows 71 exemplified positions of mutations that were individually tested and tested in various combinations for determining their effect on salt tolerance or thermostability, highlighted in gray boxes and mapped onto the amino acid sequence of SEQ ID NO:1 (wild-type T4 DNA Ligase). These mutants are at positions 12, 19, 23, 35, 41, 42, 43, 50, 63, 66, 71, 89, 99, 108, 119, 121, 127, 140, 142, 145, 149, 155, 175, 178, 192, 199, 210, 213, 270, 272, 275, 284, 288, 289, 290, 292, 293, 294, 295, 299, 301, 302, 306, 309, 310, 311, 312, 318, 323, 324, 327, 333, 339, 351, 353, 358, 363, 375, 387, 393, 426, 427, 429, 439, 445, 446, 455, 461, 462, 466, 476.

FIG. 11 shows an alignment of 11 ligases with greater than 80% sequence identity to wild-type T4 DNA ligase. The sequences are obtained from a Blast search in GenBank and are annotated accordingly (SEQ ID NOs:2-47).

DETAILED DESCRIPTION OF THE EMBODIMENTS

Methods and compositions are provided herein to improve ligation of two polynucleotides having complementary single stranded terminal regions using non-natural ATP-dependent DNA ligase variants.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Certain terms are used herein for which explanations are provided below.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The term "polynucleotide" as used herein denotes a double stranded multimer of nucleotides Polynucleotides may be synthetic or may be made enzymatically and may contain ribonucleotide monomers or deoxyribonucleotide monomers, or both ribonucleotide monomers and deoxyribonucleotide monomers.

The terms "determining," "measuring," "evaluating," "assessing," "assaying," and "analyzing" are used interchangeably herein to refer to any form of measurement and include determining if an element is present or not. These terms include both quantitative and/or qualitative determinations. Assessing may be relative or absolute. "Assessing the presence of" includes determining the amount of something present, as well as determining whether it is present or absent.

The term "non-naturally occurring" refers to a composition that does not exist in nature. In the context of a protein, the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A non-naturally occurring protein may contain an N-terminal methionine or may lack one or more post-translational modifications (e.g., glycosylation, phosphorylation, etc.) if it is produced by a different (e.g., bacterial) cell.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; e) a combination that is in a form that not found in nature, e.g., dried, freeze dried, crystalline, aqueous; and/or d) a combination that contains a component that is not found in nature. For example, a preparation may contain a buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "corresponding to" in the context of corresponding positions, refers to positions that lie across from one another when sequences are aligned, e.g., by the BLAST algorithm.

The term "variant bacteriophage DNA ligase" encompass non-natural bacteriophage DNA ligases that have amino acid sequences that are at least 80% identical to the wild-type T4 DNA ligase of SEQ ID NO:1. Enzymes having a similar architecture can be identified using the Conserved Domain Architecture Retrieval Tool (CDART) program of the National Center for Biotechnology Information (Geer, et al. Genome Research 12:1619-1623 (2002)) or by other predictive programs, based on searches employing the sequence of T4 DNA ligase. Examples of enzymes identified in this manner include: T even bacteriophages or related viruses including *Salmonella* phage STP4-a; *Shigella* phage 5P18; Enterobacteria phage RB69; Bacteriophage T3; *Klebsiella* phage PKO111; *Acinetobacter* phage 221; and *Yersinia* phage phiR1-RT. In addition, other related bacteriophages such as T3, T7, SP6, bacteriophage phiKMV, Enterobacteria bacteriophage K1-5, Vibriophage VpV262, BA14, BA127 and BA156 may encode similar enzymes.

As used herein, the term "incubating", refers to maintaining a reaction under specified conditions. Unless stated otherwise, known reaction conditions suitable for the enzymes and reagents are used in the present method.

As used herein, the term "plurality" refers to a group that contains at least 2 members. For example, a plurality of labeled nucleotides means 2 or more labeled nucleotides. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

As used herein, the term "composition" refers to a combination of reagents that may contain other reagents, e.g., glycerol, salt, dNTPs, ATP etc., in addition to those listed. A composition may be in any form, e.g., aqueous or lyophilized, and may be at any state (e.g., frozen or in liquid form).

Embodiments of the DNA ligase described herein are variants of ATP ligases that are capable of joining two polynucleotides that have compatible single strand ends to form an intact single polynucleotide. These variants have been synthesized de novo and in vitro and are demonstrated to have improved properties compared to naturally occurring ligases.

Provided herein, in various embodiments, are variant bacteriophage DNA ligases belonging to the closely related family of bacteriophage DNA ligases having at least 80% amino acid sequence identity with T4 DNA ligase have been engineered to contain one or more amino acid substitutions corresponding to those identified for T4 DNA ligases described herein. Examples of these variant T4 ligase have activity in high ionic strength environments and/or stability at temperatures >40° C.

Embodiments of the variants include one or more mutations at positions that correspond to certain positions in the amino acid sequence of wild-type T4DNA ligase (SEQ ID NO:1) which is provided by means of reference. It will be readily understood that the sequence of T4 DNA ligase is similar to other T-phage DNA ligases, such as T6, and that it is expected that the amino acid substitutions described herein may be transferred to other, related DNA ligases and their variants with the same effect.

In some embodiments, the variant: (i) may have an amino acid sequence that is at least 80% sequence identity (e.g., at least 90%, at least 90%, at least 95%, at least 97%, at least 98% or at least 99% identity) to SEQ ID NO:1; and (ii) may comprise one or more (e.g., at least two, at least three, at least five, or at least ten) amino acid substitutions at one or more positions corresponding to those specified below with respect to SEQ ID NO:1 and described in FIG. 10:

```
(wild-type T4 DNA ligase)
                                      SEQ ID NO: 1
MILKILNEIASIGSTKQKQAILEKNKDNELLKRVYRLTYSRGLQYYIKK

WPKPGIATQSFGMLTLTDMLDFIEFTLATRKLTGNAAIEELTGYITDGK

MKDDVEVLRRVMMRDLECGASVSIANKVWPGLIPEQPQLASSYDEKGIN

KNIKFPAFAQLKADGARCFAEVRGDELDDVRLLSRAGNEYLGLDLLKEE

LIKMTAEARQIHPEGVLIDGELVYHEQVKKEPEGLDFLFDAYPENSKAK

EFAEVAESRTASNGIANKSLKGTISEKEAQCMKFQVWDYVPLVEIYSLP

AFRLKYDVRFSKLEQMTSGYDKVILIENQVVNNLDEAKVIYKKYIDQGL

EGIILKNIDGLWENARSKNLYKFKEVIDVDLKIVGIYPHRKDPTKAGGF

ILESECGKIKVNAGSGLKDKAGVKSHELDRTRIMENQNYYIGKILECEC

NGWLKSDGRTDYVKLFLPIAIRLREDKTKANTFEDVFGDFHEVTGL
```

Examples of variant bacteriophage DNA ligases found to have significant improvement in salt tolerance (e.g. up to at least 250 mM KCl-500 mM KCl) included those with a mutation at any of the 50 following positions corresponding to SEQ ID NO:1: 358, 145, 318, 363, 19, 327, 462, 142, 121, 42, 192, 445, 149, 210, 175, 199, 427, 429, 42, 121, 333, 309, 429, 155, 145, 318, 306, 108, 145, 387, 284, 62, 309, 192, 323, 351, 387, 23, 299, 393, 71, 288, 127, 333, 66, 295, 310, 302, 275, 333, 301, 294, 306, 309, 323, 439, 466, 476, 294, 324, 426, 289, 294, 42, 275, 353, 272, 311, 294, and 275.

Examples of 74 mutations tested and found to improve ligase activity by greater than 1 Standard deviation (SD) improvement over wild-type T4 DNA ligase activity, include those corresponding to: A358K, G145K, I318R, L363Q, Q19L, G145T, N327S, I462K, D142S, I121T, E466I, G42K, L192K, L445V, N149K, E210N, D175G, K199E, E427A, Q429R, G42Q, I121L, V333D, Q309K, Q429K, F155Y, G145A, I318E, K306V, V108I, G145L, T387K, Y284I, M62S, Q309E, L192D, Q323R, I351P, T387H, E23K, K299P, I393V, F71L, V288N, P127K, V333E, T66Q, A295E, E466W, M310L, V302E, Q275V, V333A, D301K, P294T, K306R, Q309S, Q323T, C439I, E466R, D476E, P294I, V324I, M426W, E289V, P294V, P294D, G42R, Q275S, G353A, K272N, T311A, P294K, and Q275R.

The variant bacteriophage DNA ligases found to have significant increased temperature tolerance (45° C.-55° C.) included those with a mutation at any of the 63 following positions corresponding to SEQ ID NO:1: 358, 299, 293, 462, 461, 445, 213, 358, 140, 301, 476, 178, 333, 302, 323, 155, 19, 466, 426, 324, 427, 306, 99, 301, 309, 29, 12, 387, 42, 192, 311, 89, 62, 270, 309, 339, 429, 35, 178, 327, 306, 50, 108, 306, 439, 290, 119, 295, 43, 142, 309, 429, 306, 375, 295, 12, 41, 439, 192, 66, 275, 312, 333.

Examples of 69 mutations tested and found to improve ligase activity by greater than 1 Standard deviation (SD) improvement over wild-type T4 DNA ligase activity, including those corresponding to: A358G, K299P, L293K, I462K, A461I, L445V, L213M, L293R, L293E, A358K, S140P, L293N, D301K, D476E, R178K, V333K, V302E, Q323T, F155Y, Q19L, E466I, M426W, V324I, E427A, K306Q, K99P, D301E, Q309K, L293D, I12A, T387K, G42K, L192D, T311V, E89A, M62S, K455S, S270T, Q309A, I339R, Q429K, Y35F, R178S, N327S, K306R, W50F, V108I, K306M, C439V, I290V, V119A, A295K, L431, D142S, Q309E, R178N, Q429R, K306I, K375R, A295P, I12T, R41P, C439I, L192K, T66Q, Q275A, S312E, and V333A.

In some embodiments, the variant may comprise substitutions at a plurality of positions described above including at least two, at least three, at least four, at least five, at least ten, at least fifteen, or all twenty positions corresponding to positions 19, 63, 140, 142, 145, 155, 213, 292, 293, 299, 318, 327, 358, 358, 363, 427, 445, 461, 462 and 466 of SEQ ID NO:1, as well as well as optionally one or more (e.g., at least two, at least three, at least five, or at least ten) other substitutions e.g. 12, 23, 35, 41, 42, 43, 50, 66, 71, 89, 99, 108, 119, 121, 127, 142, 149, 175, 178, 192, 199, 210, 270, 272, 275, 284, 288, 289, 290, 293, 294, 295, 301, 302, 306, 309, 310, 311, 312, 318, 323, 324, 333, 339, 351, 353, 375, 387, 393, 426, 429, 439, 446, 455, and 476. One or more of the other substitutions may be at other positions such as those listed in the Examples section below.

In some embodiments, the variant: (i) may has an amino acid sequence is at least 80% sequence identity (e.g., at least 90%, at least 95%, at least 97%, at least 98% or at least 99% identity) to SEQ ID NO:1; and (ii) comprises a plurality (e.g., at least two, at least three, at least five, at least ten, at least fifteen or all twenty) of the following amino acid substitutions: Q19L, L63Q, S140P, D142S, G145K, F155Y, L213M, S292G, L293K, K299P, I318R, N327S, A358G, A358K, L363Q, E427A, L445V, A461I, I462K and E466I, wherein the amino acid substitutions are at positions that correspond to positions in SEQ ID NO:1. The variant may optionally one or more (e.g., at least two, at least three, at least five, or at least ten) other substitutions. One or more of the other substitutions may be at other positions such as those listed in the Examples section below.

In one embodiment, a plurality of mutations in a bacteriophage DNA ligase were introduced and these were all found to enhance salt tolerance of the ligase. The positions correspond to those in SEQ ID NO:1 and examples of mutations include those listed below:

| | Corresponding position | Example of mutation |
|---|---|---|
| (a) | 140, 293, 445 | L293K, L445V |
| (b) | 19, 155, 462 | Q19L, F155Y, I462K |
| (c) | 19, 155, 462 | Q19L, F155Y, I462K |
| (d) | 19, 155, 292, 462 | Q19L, F155Y, S292N, I462K |
| (e) | 19, 427, 445, 462 | Q19L, E427A, L445V, I462K |
| (f) | 19, 327, 363, 462 | Q19L, N327S, L363Q, I462K |
| (g) | 318, 358, 445, 462 | I318R, A358K, L445V, I462K |
| (h) | 155, 427, 462, 466 | F155Y, E427A, I462K, E466I |
| (i) | 19, 155, 445, 462, 466 | Q19L, F155Y, L445V, I462K, E466I |
| (j) | 19, 155, 427, 445, 462, 466 | Q19L, F155Y, E427A, L445V, I462K, E466I |
| (k) | 358, 445, 462 | A358K, L445V, I462K |
| (l) | 327, 358, 445, 462 | N327S, A358K, L445V, I462K |
| (m) | 358, 427, 462 | A358K, E427A, I462K |
| (n) | 358, 427, 445 | A358K, E427A, L445V |

In another embodiment, mutations at positions corresponding to 292, 293, 299, 358, 445 and 462 in SEQ ID NO:1 were found to be preferred for temperature tolerance, for example mutants corresponding to S292G, L293K, K299P, A358G, L445V and I462K.

Analysis of ligation performance of mutants using polynucleotides having 4-bp 5'-overhangs revealed improvements at least in the temperature range of 48° C.-55° C. All mutants described above and in FIG. 7 showed an improvement in heat tolerance compared to wild-type at 48° C., 50° C. and at 55° C.

Although examples of mutations that were tested are given above, equivalent mutations at the identified positions may include other amino acid substitutions. For example, amino acids may be grouped together into small aliphatic, nucleophilic, hydrophobic, aromatic, acidic, basic and amide. Small aliphatic: G, A; Nucleophilic: S, T, C; Hydrophobic: V, L, I, M, P; Aromatic: F, Y, W; Acidic: D, E; Basic: H, K, R; and Amide: N, Q.

Alternative mutations that can be considered to be equivalent by those of ordinary skill in the art are described below:

Q19L, where leucine (L) can be substituted by other hydrophobic amino acids such as valine (V), isoleucine (I), methionine (M) or proline (P).

L63Q, where glutamine (Q) can be substituted by other amide-containing amino acids such as asparagine (N).

S140P, where proline (P) can be substituted by other hydrophobic amino acids, such as valine (V), leucine (L), isoleucine (I) or methionine (M).

D142S, where serine (S) can be substituted by other nucleophilic amino acids such as threonine (T) or cysteine (C).

G145K, where lysine (K) can be substituted by other basic amino acids such arginine (R) or histidine (H).

F155Y, where tyrosine (Y) can be substituted by other aromatic amino acids such as phenylalanine (F) or tryptophan (W).

L213M, where methionine (M) can be substituted by other hydrophobic amino acids such as valine (V), leucine (L), isoleucine (I) and proline (P).

S292G, where glycine (G) can be substituted by other small aliphatic amino acids such as alanine (A).

L293K, where lysine (K) can be substituted by other basic amino acid residues such as arginine (R) and histidine (H).

K299P, where proline (P) can be substituted by other hydrophobic amino acids, such as valine (V), leucine (L), isoleucine (I) or methionine (M).

I318R, where arginine (R) can be substituted by other basic amino acids such as histidine (H) and lysine (K).

N327S, where serine (S) can be substituted by other nucleophilic amino acids such as threonine (T) or cysteine (C).

A358K, where lysine (K) can be substituted by other basic amino acid residues such as arginine (R) and histidine (H).

A358G, where glycine (G) can be substituted by other small aliphatic amino acids such as alanine (A).

L363Q, where glutamine (Q) can be substituted by other amide-containing amino acids such as asparagine (N).

E427A, where alanine (A) can be substituted by other small aliphatic amino acids such as glycine (G).

L445V, where valine (V) can be substituted by other hydrophobic amino acids such as leucine (L), isoleucine (I), methionine (M) and proline (P).

A461I, where isoleucine (I) can be substituted by other hydrophobic amino acids such as valine (V), leucine (L), methionine (M) and proline (P).

I462K, where lysine (K) can be substituted by other basic amino acid residues such as arginine (R) and histidine (H).

E466I, where isoleucine (I) can be substituted by other hydrophobic amino acids such as valine (V), leucine (L), methionine (M) and proline (P).

The sequence of T4 DNA ligase is similar to other Enterobacteria phage DNA ligases, such as T6 (GenBank accession number AAA32562.1) and RB32 (GenBank accession number YP_803139.1), such that mutations that it is expected that the amino acid substitutions described herein may be transferred to other, related DNA ligases and their variants with the same effect. Other DNA ligase that are related, include DNA ligases from Enterobacter phage CC31 (GenBank accession number: YP_004010059.1), Shigella phage SP18 (GenBank accession number: YP_003934836.1) and Klebsiella phage PKO111 (GenBank accession number: YP_009289585.1). In addition to the above, US 2018/0320162 describes a number of ligases from various phage and various mutants thereof. Each and every sequence and variant described in US 2018/0320162 are incorporated herein by reference where the substitutions may be added individually or in combination to mutations at positions 358, 327 and/or 363 corresponding to SEQ ID NO:1.

As such, in certain embodiments, this disclosure provides a non-naturally occurring variant of a naturally occurring bacteriophage DNA ligase, wherein the variant has an amino acid sequence that is at least 90% identical to (e.g., at least 90% or at least 98% identical to) the naturally occurring bacteriophage DNA ligase and comprises one or more amino acid substitutions selected from mutations described above to make the variant more salt- or heat-tolerant than the naturally-occurring parent (i.e., active at a higher salt concentrations or reaction temperatures, e.g., a salt concentration that is at least 10 mM, 20 mM, 50 mM 100 mM, 250 mM, 300 mM, 350 mM, 400 mM, 450 mM or 500 mM) or a temperature that is 5° C., at least 10° C. or a temperature that is at least 15° C. higher than the optimum temperature of the naturally-occurring parent (e.g., at a temperature of 45° C., 50° C. or 55° C.). In some cases, the variant has at least 90% sequence identity to SEQ ID NO:1, although in some embodiments the variant may have at least 90% sequence identity to the T6, T-even or another bacteriophage DNA ligase.

Also provided is a composition, e.g., an aqueous composition comprising: i. an isolated variant DNA ligase as described above and ii. a buffering agent (e.g., Tris). In some embodiments, the composition may optionally contain glycerol, ATP salt (e.g., KCl or NaCl), EDTA, detergent (e.g., Triton X-100) suitable for storage. In other embodiments, the composition may be a reaction mix. In these embodiments, the composition may further comprise ATP, a nucleic acid containing a 5' end and/or a nucleic acid containing a 3' end. In particular embodiments, the reaction mix may contain at least 100 mM salt (e.g., NaCl or KCl).

Kits

Also provided is a kit comprising: i. a variant bacteriophage DNA ligase as described herein; and ii. a reaction buffer. In some embodiments, the reaction buffer may contain up to 100 mM salt, e.g., as much as 250 mM, 300 mM, 400 mM or even 500 mM salt. The components of the kit may be combined in one container, or each component may be in its own container. For example, the components of the kit may be combined in a single reaction tube or in one or more different reaction tubes. Further details of the components of this kit are described above. The kit may also contain other reagents described above and below that may be employed in the method depending on how the method is going to be implemented. In some embodiments, the kit may comprise of a variant as described above and a buffer in which the variant is active, or a concentrated form thereof.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. USB Flash Drive, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods

Also provided is a method for ligating a nucleic acid molecule. In some embodiments, this method may comprise combining a variant bacteriophage DNA ligase as described herein with a 5' end of a nucleic acid and a 3' end of a nucleic acid to produce a reaction mix; and (b) incubating the reaction mix to ligate the 5' end and the 3' end together. The 3' and 5' ends may be on different nucleic acid molecules or the same molecule. The ends may be blunt or complementary single strand overhangs. In some embodiments, the incubating may be done at a temperature of at least 45° C. (e.g., in the range of 45° C. to 60° C., 45° C. to 50° C., 50° C. to 55° C. or 55° C. or 60° C.). In some embodiments, the reaction mix may comprise salt (e.g., NaCl or KCl) at a concentration of as much as 100 mM, 250 mM, 300 mM, 400 mM or 500 mM.

In embodiments of the invention, salt tolerant ligases can be used for master mixes for ligating DNA adaptors for high through put (next-generation) sequencing library preparation, for creating longer DNA fragments from shorter DNA fragments generated by amplification or oligonucleotide assembly, or other reaction conditions where other enzymes are present, and the buffer has been optimized for a combination of all enzymes.

In embodiments, salt tolerant engineered T4 DNA ligase variants that can carry out end-joining under salt conditions specified herein can be applied to applications requiring high fidelity end-joining. Salt or heat tolerant 14 variants can be used in buffers containing simple salts commonly used in Next Generation sequencing formulations and other upstream enzymatic reactions other than ligation; or to permit more flexible temperature cycling protocols in DNA assembly reactions. Heat or salt tolerant end-joining ligases can also be used in combination with enzymes that have buffer or incubation temperature requirements incompatible with wild-type T4 DNA ligase.

In embodiments, temperature tolerant mutant ligases may be used for Golden Gate gene assembly or related DNA cloning and assembly methods. For example, Golden Gate cloning is a one-pot method for the assembly of large DNA fragments from many smaller fragments. Golden Gate assembly uses a Type IIS restriction enzyme and T4 DNA ligase. Golden Gate Assembly exploit the ability of Type IIS restriction endonucleases to cleave DNA outside of the recognition sequence. The inserts and cloning vectors are designed to place the Type IIS recognition site distal to the cleavage site, such that the Type IIS restriction endonuclease can remove the recognition sequence from the assembly. The advantages of Golden Gate assembly are: the overhang sequence created is not dictated by the restriction endonuclease, and therefore no scar sequence is introduced, the fragment-specific sequence of the overhangs allows orderly assembly of multiple fragments simultaneously, and the restriction site is eliminated from the ligated product, so digestion and ligation can be carried out simultaneously. The net result is the ordered and seamless assembly of DNA fragments in one reaction. The typical Type IIS restriction endonuclease used in Golden Gate cloning is BsaI, which has optimal activity at 50° C. Temperature tolerant ligase variants are used here in combination with thermophilic Type IIS restriction enzymes for Golden Gate assembly. Embodiments of the T4 DNA Ligase variants described herein that are resistant to thermal denaturation at above 50° C. or is active at temperatures above 50° C. provide for an improved streamlined Golden Gate Assembly method.

EXAMPLES

Example 1: Survey of Ligation Efficiency of Mutant Ligases with Point Mutations in High Salt or at Increased Temperatures Point mutations were introduced in the T4 DNA ligase using high throughput oligo-directed PCR-based mutagenesis methods (Jin, P., et al. ACS Synthetic Biology, 5(3), 259-268.). The resultant mutant double-stranded DNA products contained a variant T4 DNA ligase gene under the control of a T7 promoter and were used as templates for gene expression by PURExpress® (New England Biolabs, Ipswich, Mass.), and in vitro transcription and translation system. T4 DNA ligase variant proteins were expressed by PURExpress using standard protocols (PURExpress In Vitro Protein Synthesis Instruction Manual, NEB catalog #E6800). Expressed proteins were added to a standard ligation reaction containing standard ligase reaction buffer (1×T4 DNA Ligase Reaction Buffer: 50 mM Tris-HCl, pH 7.5 @ 25° C., 10 mM $MgCl_2$, 1 mM ATP, 10 mM DTT), 300 mM KCl and double-stranded DNA substrates with a 4 base 5' single-stranded overhang (5'GATC). The substrates were created by annealing two oligonucleotides, 5'-/5Phos/ GATCCTTAGATAGTATACTGAGTTCTGTAAAC- GAGCTATTGAATTC (SEQ ID NO:48)/36-FAM/-3' and 5'-GAATTCAATAGCTCGTTTACAGAACTCAGTATAC-TATCTAAG (SEQ ID NO:49)-3', where /5Phos/ is a 5'-phosphate group and /36-FAM/ is a 3' fluorescein label. Reactions were incubated for 15 minutes at 25° C. Ligation product formation was determined by capillary electrophoresis, as described in Greenough, L., et al. (2016). *Nucleic Acids Research,* 44(2), e15.). The point mutations are provided for those mutants that generated at least 1 standard deviation improvement over wild-type (see FIG. 1 and FIG. 6).

Example 2: Enhanced Ligation Efficiency of Polynucleotides with N4 Overhang in a Buffer Containing KCl The mutant ligases were obtained using by cloning mutagenic PCR products (as described in Example 1) into a bacterial expression vector. Bacteria harboring a single mutant ligase was induced for protein expression, and ligase variants were purified by high throughput immobilized metal affinity chromatography (IMAC), using a KingFisher Flex Purification System (Thermo Fisher Scientific). IMAC purified ligase variants were added to a ligation reaction as described below.

Ligation was performed as follows: an enzyme mix (10 µl), containing 7.5 ng of ligase (wild-type or variant), 1×T4 DNA Ligase Reaction Buffer, 250 mM KCl, and water, was added to a 2× substrate mix (10 µl), such that the final reaction contained 1×T4 DNA Ligase Reaction Buffer, 250 mM KCl, 10 nM substrate. The substrate was double-stranded DNA containing a 4 base 5'GATC overhang (N4) as described in Example 1. The reaction was incubated for 15 minutes at 25° C. and stopped with an equal volume (20 µl) of solution containing 50 mM EDTA/0.1% Triton X-100. The reaction was further diluted 1/100 in water and analyzed by capillary electrophoresis, as described in Greenough, et al. (2016). *Nucleic Acids Research,* 44(2), e15. Reactions were performed in triplicate.

The graphs in the figures provide the fractional or percentage improvement in ligation efficiency under the specified conditions. The results are shown in FIG. 2 for 15 different mutants: STM33 (S140P, L293K, L445V), WS11 (Q19L, F155Y, I462K), WS6 (Q19L, F155Y, I462K), A358K (A358K), WS5 (Q19L, F155Y, S292N, I462K), STM26 (Q19L, E427A, L445V, I462K), STM24 (Q19L, N327S, L363Q, I462K), STM4 (I318R, A358K, L445V, I462K), STM29 (F155Y, E427A, I462K, E466I), WS4 (Q19L, F155Y, L445V, I462K, E466I), WS7 (Q19L, F155Y, E427A, L445V, I462K, E466I), STM1 (A358K, L445V, I462K), STM9 (N327S, A358K, L445V, I462K), STM5 (A358K, E427A, I462K), STM7 (A358K, E427A, L445V). Error bars represent the standard deviation of three independent replicates. In all cases, the ligation efficiency was enhanced in the presence of KCl compared with wild-type T4DNA ligase.

The results in FIG. 3 and FIG. 4 show the results of ligation in 250 mM KCl and 400 mM KCl using AKTA purified T4 DNA ligase variants as described in FIG. 3 all of which showed significant ligation enhancement in KCl. Briefly, ligase variants were purified by affinity chromatography using an AKTA FPLC Protein Purification System (GE Healthcare Life Sciences, Marlborough, Mass.). Ligase variants were purified by passing over a DEAE 16/10 column, then affinity purification by binding, washing and eluting with a salt gradient from 0-1M NaCl with the following columns: His-Prep FF 16/10, HiPrep Heparin FF 16/10, HiPrep Q FF 16/10 (all from GE Healthcare Life Sciences, Marlborough, Mass.). Finally, variants were further purified using a HiPrep 26/60 Sephacryl S-100 HR sizing column (GE Healthcare Life Sciences, Marlborough, Mass.).

Purified ligase variants (7.5 ng) were added to a reaction as described above, except the final reaction contained variable 250 mM KCl (FIG. 3) or 400 mM KCl (FIG. 4). The ligase variants correspond to STM12 (A358K, E427A, L445V, I462K), STM15 (A358K, E427A, E446I, I462K), STM16 (N327S, A358K, L363Q, I462K), STM23 (D142S, N327S, L363Q, I462K), STM25 (E427A, L445V, I462K), STM27 (Q19L, D142S, N327S, L363Q, I462K) and WS1 (G145K, A358K, I462K).

Error bars represent the standard deviation of three independent replicates.

Example 3: Enhanced Ligation of Single Base T/a Overhangs by Ligase Variants

To determine ligation activity on single base T/A overhangs, reactions were assembled as follows: 30 µl Blunt TA Ligation Master Mix (either commercial T4 DNA Ligase version (NEB #M0367L, or equivalent prepared version with each ligase variant), was added to 1 µl Ligation Enhancer (NEB E7805), 7 µl Ultra II Fragmentation Buffer (NEB7805), 6.85 µl 100 nM T/A substrate, 1.7 µl 2M KCl, and 15.1 µl water for a total reaction volume of 68.5 µl. The reactions were transferred to a PCR plate at 25° C. and incubated for 15 minutes. Reactions were stopped with 68.5 µl Ligase Stop Solution (0.1% Triton X-100, 50 mM EDTA). Ligation products were diluted and analyzed by capillary electrophoresis as described in Example 1). The T/A substrate was formed by annealing two oligos: /5Phos/GATGGGACCTACAATGTACCAGAAGCGTC (SEQ ID NO:52)/36-FAM/ and 5'-GACGCTTCTGGTACATTG-TAGGTCCCATCT (SEQ ID NO:53)-3' where /5Phos/ is a 5' phosphate group and /36-FAM/ is a 3' fluorescein label. Error bars represent the standard deviation of three independent replicates. The results are reported in FIG. 5. The ligase variants correspond to STM27 (Q19L, D142S, N327S, L363Q, I462K), STM25 (E427A, L445V, I462K), STM12 (A358K, E427A, L445V, I462K), STM23 (D142S, N327S, L363Q, I462K), WS1 (G145K, A358K, I462K), STM16 (N327S, A358K, L363Q, I462K), STM15 (A358K, E427A, E446I, I462K).

Example 4: Ligase Variants with Enhanced Resistance to Thermal Denaturation after Subjection to Increased Temperatures T4 DNA Ligase variants were constructed and expressed as described in Example 1. In vitro expressed ligase variants were added to a reaction containing standard ligase reaction buffer (1×T4 DNA Ligase Reaction Buffer: 50 mM Tris-HCl, pH 7.5 @ 25° C., 10 mM MgCl$_2$, 1 mM ATP, 10 mM DTT) and incubated for 2 minutes at 52° C. After heat treatment, double-stranded DNA substrates with a 4 base 5' single-stranded 5'GATC overhang (N4), were added. The substrates were created by annealing two oligonucleotides, 5'75Phos/GATCCTTAGATAGTATACTGAGTTCTG-TAAACGAGCTATTGAATTC (SEQ ID NO:48)/36-FAM/-3' and 5'-GAATTCAATAGCTCGTTTACAGAACTCAG-TATACTATCTAAG (SEQ ID N0:49)-3', where /5Phos/ is a 5'-phosphate group and /36-FAM/ is a 3' fluorescein label. Reactions were incubated for 15 minutes at 25° C. to assay ligase activity remaining after heat treatment. Ligation product formation was determined by capillary electrophoresis, as described in Greenough, L., Schermerhorn, K. M., Mazzola, L., Bybee, J., Rivizzigno, D., Cantin, E., et al. (2016). Adapting capillary gel electrophoresis as a sensitive, high-throughput method to accelerate characterization of nucleic acid metabolic enzymes. *Nucleic Acids Research*, 44(2), e15. http://doi.org/10.1093/nar/gkv899). Error bars represent the standard deviation of three independent replicates. The results are reported in FIG. 6.

Variant ligases having mutations specified in FIG. 7 were purified by affinity chromatography using an AKTA FPLC Protein Purification System. Briefly, ligase variants were purified by affinity chromatography using an AKTA FPLC Protein Purification System. Ligase variants were purified by passing over a DEAE 16/10 column, then affinity purification by binding, washing and eluting with a salt gradient from 0-1M NaCl with the following columns: His-Prep FF 16/10, HiPrep Heparin FF 16/10, HiPrep Q FF 16/10. Finally, variants were further purified using a HiPrep 26/60 Sephacryl S-100 HR sizing column. Ligase variants were subjected to incubation at an elevated temperature (52° C.), and remaining ligase activity after heat treatment was measured at 25° C. Variant ligases correspond to: HTM10 (L293K, K299P, A358G, L445V), HTM12 (L293K, A358G, L445V, I462K), HTM15 (K299P, A358G, I462K), HTM25 (S292G, A358G, L445V, I462K), HDM24 (A358G, I462K) and HTM-M (S292G, L293K, K299P, A358G, L445V, I462K).

Ligation was performed as follows: an enzyme mix (10 µl), containing 9 ng of ligase (wild-type or variant) and 1×T4 DNA Ligase Reaction Buffer was heated to 52° C. for 5 minutes, then the temperature was reduced to 25° C. and a 2× substrate mix (10 µl) was added, such that the final reaction contained 1×T4 DNA Ligase Reaction Buffer and 10 nM substrate. The N4 substrate was double-stranded DNA containing a 4 base 5'GATC overhang as described in Example 1. The reaction was incubated for 15 minutes at 25° C. to assay remaining ligase activity after heat treatment. Reactions were stopped with an equal volume (20 µl) of solution containing 50 mM EDTA/0.1% Triton X-100). The reaction was further diluted 1/100 in water and analyzed by capillary electrophoresis, as described in Greenough, L., Schermerhorn, K. M., Mazzola, L., Bybee, J., Rivizzigno, D., Cantin, E., et al. (2016). Adapting capillary gel electrophoresis as a sensitive, high-throughput method to accelerate characterization of nucleic acid metabolic enzymes. *Nucleic Acids Research*, 44(2), e15. http://doi.org/10.1093/nar/gkv899). Reactions were performed in triplicate. The results are shown in FIG. 7.

Example 5: Enhanced Ligation Efficiency of Polynucleotides with N4 and Blunt Overhangs at Increased Temperatures Ligation was performed using the variant ligases described in FIG. 7 as follows: and enzyme mix (10 µl) containing 120 ng of ligase variant in 1×T4 DNA Ligase Reaction Buffer was preheated for 5 minutes at 50° C. After the three minutes, and 10 µl of 2× substrate mixture was added to the enzyme mixtures and allowed to react at 50° C. for 15 minutes. The final reaction contained 1×T4 DNA Ligase Reaction Buffer and 10 nM N4 and blunt substrates were added, (N4 substrates were as described in Example 1. Blunt DNA substrates were made by annealing two oligonucleotides, /5Phos/AAATCTAAGCCACAACGCCGAG-GCAAACGGATGGCTC (SEQ ID NO:50)/36-FAM/ and 5'-GAGCCATCCGTTTGCCTCGGCGTTGTGGCTTA- GATTT (SEQ ID NO:51)-3' where /5Phos/ is a 5' phosphate group and /36-FAM/ is a 3' fluorescein label. Ligation products were analyzed as described in Example 1, and the results are shown FIG. 8. Variant ligases correspond to: HTM10 (L293K, K299P, A358G, L445V), HTM12 (L293K, A358G, L445V, I462K), HTM15 (K299P, A358G, I462K), HTM25 (S292G, A358G, L445V, I462K), HDM24 (A358G, I462K) and HTM-M (S292G, L293K, K299P, A358G, L445V, I462K). The results are shown in FIG. 8.

Example 6: Determining Fidelity and Efficiency of Ligation

The mutants described in FIG. 3 were used to ligate substrate in 250 mM KCL and also separately in T4 DNA ligase buffer containing no salt. The ligated polynucleotides with a 4 base overhang were sequenced using a PacBio SMRT ligation fidelity assay. The mean value for fidelity and efficiency was calculated from the sequence data. The variation around the mean was also determined.

It was observed that in high salt, mean fidelity was consistently higher than in no salt buffers for all mutants and the wild-type control and T3/T7 ligase controls. However, the efficiency of ligation of the WT T4 DNA ligase in high salt was substantially more variable than observed for the mutants. The efficiency of ligation of the mutants were similar to wild-type phage DNA ligases tested but substantially less variable than wild-type T4 DNA Ligase in both high salt and no salt buffers.

Example 7: Enhanced Tolerance to Elevated Temperatures Ligation of Blunt Substrates at Elevated Temperatures by Ligase Variants Ligation reactions (20 µL) were carried out in T4 DNA ligase reaction buffer with 1 µg of T4 ligase (either wild-type or HTM-M) and a DNA substrate with blunt ends (100 nM). The substrate was made by annealing two oligonucleotides, /5Phos/AAATCTAAGCCACAACGCCGAGGCAAACG-GATGGCTC (SEQ ID NO:50)/36-FAM/ and 5'-GAGC-CATCCGTTTGCCTCGGCGTTGTGGCTTAGATTT (SEQ ID NO:51)-3' where /5Phos/ is a 5' phosphate group and /36-FAM/ is a 3' fluorescein label. Reactions were incubated for 15 minutes at the indicated temperatures (30° C.-55° C.) and stopped with a chelating quench solution (20 µL) containing 50 mM EDTA and 0.1% Triton X-100. The reactions were further diluted 1/100 in water and analyzed by capillary electrophoresis, as described in Greenough et al. (2016) and Example 1. Error bars represent the standard deviation of three independent replicates. The variant corresponds to HTM-M (S292G, L293K, K299P, A358G, L445V, I462K). The results are reported in FIG. 9A.

Example 8: Enhanced Ligation at Elevated Temperatures for Ligation of Blunt DNA Substrates The HTM-M ligase variant retains high activity after incubation at high temperatures. Enzyme solutions (10 µL) containing 100 ng of either wild-type or HTM-M mutant ligase protein in T4 DNA ligase buffer were incubated for 1 hour at the indicated temperatures (25-50° C.). After the initial incubation, a DNA substrate with blunt ends (as described in Example 7) was added to a final concentration of 100 nM. Ligation reactions were carried out for 15 minutes at 25° C. as described in FIG. 11. Error bars represent the standard deviations of at least three independent replicates. The variant corresponds to HTM-M (S292G, L293K, K299P, A358G, L445V, I462K). The results are reported in FIG. 9B.

REFERENCES

1. Lehman I R. DNA ligase: structure, mechanism, and function. Science. 1974; 186(4166):790-7. pmid:4377758
2. Shuman S. DNA ligases: progress and prospects. J Biol Chem. 2009; 284(26):17365-9. pmid:19329793
3. Cherepanov A V, de Vries S. Kinetics and thermodynamics of nick sealing by T4 DNA ligase. Eur J Biochem. 2003; 270(21):4315-25. pmid:14622296
4. Kukshal V, Kim I K, Hura G L, Tomkinson A E, Tainer J A, Ellenberger T. Human DNA ligase III bridges two DNA ends to promote specific intermolecular DNA end joining. Nucleic Acids Res. 2015; 43(14):7021-31. pmid:26130724
5. Pheiffer B H, Zimmerman S B. Polymer-stimulated ligation: enhanced blunt- or cohesive-end ligation of DNA or deoxyribooligonucleotides by T4 DNA ligase in polymer solutions. Nucleic Acids Res. 1983; 11(22):7853-71. pmid:6359064
6. Teraoka H, Tsukada K. Influence of polyethylene glycol on the ligation reaction with calf thymus DNA ligases I and I I. J Biochem. 1987; 101(1):225-31. pmid:3571204
7. Shuman S, Ru X M. Mutational analysis of vaccinia DNA ligase defines residues essential for covalent catalysis. Virology. 1995; 211(1):73-83. pmid:7645238
8. Lohman G J, Tabor S, Nichols N M. DNA ligases. Curr Protoc Mol Biol. 2011; Chapter 3: Unit 3.14. pmid:21472697
9. Engler C, Gruetzner R, Kandzia R, Marillonnet S. Golden gate shuffling: a one-pot DNA shuffling method based on type IIs restriction enzymes. PloS one. 2009; 4(5):e5553. pmid:19436741
10. Werner S, Engler C, Weber E, Gruetzner R, Marillonnet S. Fast track assembly of multigene constructs using Golden Gate cloning and the MoClo system. Bioeng Bugs. 2012; 3(1):38-43. pmid:22126803
11. Gibson D G, Young L, Chuang R Y, Venter J C, Hutchison C A, 3rd, Smith H O. Enzymatic assembly of DNA molecules up to several hundred kilobases. Nat Methods. 2009; 6(5):343-5. pmid:19363495
12. Cai L, Hu C, Shen S, Wang W, Huang W. Characterization of bacteriophage T3 DNA ligase. J Biochem. 2004; 135(3):397-403. pmid:15113838
13. Lauer G, Rudd E A, McKay D L, Ally A, Ally D, Backman K C. Cloning, nucleotide sequence, and engineered expression of *Thermus thermophilus* DNA ligase, a homolog of *Escherichia coli* DNA ligase. J Bacteriol. 1991; 173(16):5047-53. pmid:1840584
14. Tong J, Cao W, Barany F. Biochemical properties of a high fidelity DNA ligase from *Thermus* species AK16D. Nucleic Acids Res. 1999; 27(3):788-94. pmid:9889274
15. Doherty A J, Ashford S R, Subramanya H S, Wigley D B. Bacteriophage T7 DNA ligase. Overexpression, purification, crystallization, and characterization. J Biol Chem. 1996; 271(19):11083-9. pmid:8626651
16. Ho C K, Van Etten J L, Shuman S. Characterization of an ATP-dependent DNA ligase encoded by *Chlorella* virus PBCV-1. J Virol. 1997; 71(3):1931-7. pmid:9032324
17. Richardson C C, Masamune Y, Live T R, Jacquemin-Sablon A, Weiss B, Fareed G C. Studies on the joining of DNA by polynucleotide ligase of phage T4. Cold Spring Harb Symp Quant Biol. 1968; 33:151-64. pmid:4891960

18. Weiss B, Jacquemin-Sablon A, Live T R, Fareed G C, Richardson C C. Enzymatic breakage and joining of deoxyribonucleic acid. V I. Further purification and properties of polynucleotide ligase from *Escherichia coli* infected with bacteriophage T4. J Biol Chem. 1968; 243(17):4543-55. pmid:4879167
19. Fareed G C, Wilt E M, Richardson C C. Enzymatic breakage and joining of deoxyribonucleic acid. 8. Hybrids of ribo- and deoxyribonucleotide homopolymers as substrates for polynucleotide ligase of bacteriophage T4. J Biol Chem. 1971; 246(4):925-32. pmid:5543691
20. Sogaramella V, Khorana H G. Studies on polynucleotides. CXVI. A further study of the T4 ligase-catalyzed joining of DNA at base-paired ends. J Mol Biol. 1972; 72(3):493-502. pmid:4349756
21. Raae A J, Kleppe R K, Kleppe K. Kinetics and effect of salts and polyamines on T4 polynucleotide ligase. Eur J Biochem. 1975; 60(2):437-43. pmid:173544
22. Sgaramella V, Ehrlich S D. Use of the T4 polynucleotide ligase in the joining of flush-ended DNA segments generated by restriction endonucleases. Eur J Biochem. 1978; 86(2):531-7. pmid:350585
23. Ferretti L, Sgaramella V. Temperature dependence of the joining by T4 DNA ligase of termini produced by type I I restriction endonucleases. Nucleic Acids Res. 1981; 9(1):85-93. pmid:6259621
24. Wilson, et al (July 2013). "Engineered DNA ligases with improved activities in vitro". Protein Engineering, Design & Selection. 26 (7): 471-8. doi:10. 1093/protein/gzt024. PMID 23754529
24. Hayashi K, Nakazawa M, Ishizaki Y, Obayashi A. Influence of monovalent cations on the activity of T4 DNA ligase in the presence of polyethylene glycol. Nucleic Acids Res. 1985; 13(9):3261-71. pmid:2987879
25. Wu D Y, Wallace R B. Specificity of the nick-closing activity of bacteriophage T4 DNA ligase. Gene. 1989; 76(2):245-54. pmid:2753355
26. Sugino A, Goodman H M, Heyneker H L, Shine J, Boyer H W, Cozzarelli N R. Interaction of bacteriophage T4 RNA and DNA ligases in joining of duplex DNA at base-paired ends. J Biol Chem. 1977; 252(11):3987-94. pmid:863910

---

What is claimed is:

1. A DNA ligase, wherein the DNA ligase:
   (i) has at least 90% sequence identity to SEQ ID NO:1; and
   (ii) comprises one or more amino acid substitutions at the position corresponding to positions 142, 145, 155, 292, 318, 327, 358, 363 and 445 in SEQ ID NO:1;
   wherein if the substitution is at a position corresponding to position 292, the amino acid substitution is not glycine and
   wherein if the substitution is at a position corresponding to position 358, the amino acid substitution is not alanine or threonine.

2. The DNA ligase of claim 1, wherein the ligase comprises a substitution at the position corresponding to position 358.

3. The DNA ligase of claim 2, wherein the ligase comprises at least one additional substitution.

4. The DNA ligase of claim 2, wherein the ligase comprises at least two additional substitutions.

5. The DNA ligase of claim 2, wherein the at least one additional substitution is selected from a position corresponding positions to 12, 19, 23, 35, 41, 42, 43, 50, 63, 66, 71, 89, 99, 108, 119, 121, 127, 140, 142, 145, 149, 155, 175, 178, 192, 199, 210, 213, 270, 272, 275, 284, 288, 289, 290, 292, 293, 294, 295, 299, 301, 302, 306, 309, 310, 311, 312, 318, 323, 324, 327, 333, 339, 351, 353, 363, 375, 387, 393, 426, 427, 429, 439, 445, 446, 456, 461, 462, 466 and 476 in SEQ ID NO:1.

6. The DNA ligase of claim 1, that has at least 95% sequence identity to SEQ ID NO:1.

7. The DNA ligase of claim 1, further comprising one or more additional amino acid substitutions at a positions corresponding to positions 19, 63, 140, 142, 213, 292, 293, 299, 318, 327, 358, 445, 455, 461, 462 and 466 in SEQ ID NO:1.

8. The DNA ligase of claim 1, further comprising one or more additional substitutions selected from Q19L, L63Q, S140P, D142S, G145K, F155Y, L213M, S292G, L293K, K299P, I318R, N327S A358K, A358G, L363Q L445V, L455V, A461I, I462K, E466I, and E466W, wherein the amino acid substitutions are at a positions corresponding to positions in SEQ ID NO:1.

9. The DNA ligase of claim 1, wherein the ligase comprises two or more amino acid substitutions relative to SEQ ID NO: 1.

10. The DNA ligase of claim 8, wherein the ligase comprises five or more amino acid substitutions relative to SEQ ID NO: 1.

11. The DNA ligase of claim 8, wherein the ligase comprises ten or more amino acid substitutions relative to SEQ ID NO:1.

12. The DNA ligase of claim 1, wherein the ligase is a fusion protein.

13. The DNA ligase of claim 1, wherein, as a result of the one or more amino acid substitutions, the ligase has increased stability at 45° C., 50° C. and/or 55° C. relative to the T4 DNA ligase of SEQ ID NO:1.

14. The DNA ligase of claim 1, wherein, as a result of the one or more amino acid substitutions, the ligase has increased activity in a buffer comprising NaCl or KCl relative to the T4 DNA ligase of SEQ ID NO:1.

15. The DNA ligase of claim 1, wherein the ligase has increased activity in a buffer comprising 250 mM salt relative to the T4 DNA ligase of SEQ ID NO:1.

16. The DNA ligase of claim 1, wherein the ligase has increased activity in a buffer comprising 300 mM, 400 mM and/or 500 mM salt relative to the T4 DNA ligase of SEQ ID NO:1.

17. A composition comprising:
   a. the DNA ligase of claim 1; and
   b. a buffering agent.

18. A kit comprising:
   a. the DNA ligase of claim 1; and
   b. a reaction buffer.

19. A method for ligating polynucleotides, comprising:
   a. combining the DNA ligase of claim 1 with a first polynucleotide and a second polynucleotide to produce a reaction mix; and
   b. incubating the reaction mix to permit the DNA ligase to ligate the 5' end of the first polynucleotide to the 3' end of the second polynucleotide.

20. The method of claim 19, wherein the incubating is done at a temperature of at least 45° C.

21. The method of claim 19, wherein the reaction mix comprises salt at a concentration of at least 20 mM.

22. The method of claim 19, wherein the ends of the DNA in the ligation are selected from the group consisting of 5' overhangs of any length, 3' overhangs of any length, and blunt ends.

* * * * *